(12) United States Patent
Cox, III et al.

(10) Patent No.: US 7,754,855 B1
(45) Date of Patent: Jul. 13, 2010

(54) IMMUNOGLOBULIN FUSION PROTEINS

(75) Inventors: George N. Cox, III, Louisville, CO (US); Daniel H. Doherty, Boulder, CO (US)

(73) Assignee: Bolder Biotechnology, Inc., Boulder, CO (US)

( * ) Notice: Subject to any disclaimer, the term of this patent is extended or adjusted under 35 U.S.C. 154(b) by 1103 days.

(21) Appl. No.: 10/031,154

(22) PCT Filed: Jul. 13, 2000

(86) PCT No.: PCT/US00/19336

§ 371 (c)(1),
(2), (4) Date: Apr. 24, 2002

(87) PCT Pub. No.: WO01/03737

PCT Pub. Date: Jan. 18, 2001

Related U.S. Application Data

(60) Provisional application No. 60/143,458, filed on Jul. 13, 1999.

(51) Int. Cl.
C07K 14/00 (2006.01)
C12N 15/00 (2006.01)
A61K 38/00 (2006.01)
A61K 38/19 (2006.01)

(52) U.S. Cl. .......... 530/350; 530/351; 435/69.7; 514/2; 424/85.1

(58) Field of Classification Search .......... 536/23.5; 530/351, 350, 324
See application file for complete search history.

(56) References Cited

U.S. PATENT DOCUMENTS

| | | | |
|---|---|---|---|
| 5,073,627 A * | 12/1991 | Curtis et al. | 530/351 |
| 5,519,115 A * | 5/1996 | Mapelli et al. | 530/324 |
| 5,576,191 A * | 11/1996 | Gayle et al. | 435/69.1 |
| 5,580,853 A * | 12/1996 | Sytkowski | 514/8 |
| 5,650,150 A | 7/1997 | Gillies | 424/134.1 |
| 5,723,125 A | 3/1998 | Chang et al. | 424/134.1 |
| 6,165,476 A * | 12/2000 | Strom et al. | 424/195.11 |
| 6,242,570 B1 * | 6/2001 | Sytkowski | 530/350 |
| 6,485,726 B1 * | 11/2002 | Blumberg et al. | 424/178.1 |
| 2001/0053539 A1 * | 12/2001 | Lauffer et al. | 435/69.7 |

FOREIGN PATENT DOCUMENTS

| | | |
|---|---|---|
| EP | 1088888 A1 | 4/2001 |
| WO | WO 98/38212 | 9/1998 |
| WO | WO 9902709 A1 * | 1/1999 |
| WO | WO 9902711 A2 * | 1/1999 |

OTHER PUBLICATIONS

Amoresano, et al Glycobiology 8:779-790, 1998 'Structural characterization and independent folding of a chimeric glycoprotein comprising granulocyte-macrophage colony stimulating factor and erythropoietin sequences'.*
Qiu et al., J. Biol Chem., 1998, May 1,273(18):11173-11176.*
Eck, S. L. and Wilson, J. M.,1996, in: Goodman & Gilman's The Pharmacological Basis of Therapeutics, Ninth Edition, McGraw-Hill, New York.*
Egrie et al., *Blood*, 90(10):56A-57A (1997) Abstract.
Eppard et al., *J. Endocrinol.*, 139:441-450 (1993).
Flores-Villanueva et al., *J. Immunol.*, 156:3315-3320 (1996).
Junghans, *TIBTECH*, 15(5):155 (1997).
Kürschner et al., *J. Immunol.*, 149(12):4096-4100 (1992).
LaRochelle et al., *J. Cell Biol.*, 129(2):357-366 (1995).
Ohno et al., *Blood*, 92:174B-175B (1999) Abstract #3736.
Shin et al., *J. Biol. Chem.*, 269(7):4979-4985 (1994).
Souillard et al., *Br. J. Clin. Pharmacol.* 42:355-364 (1996).
Steele, "Structure and function in vitro and in vivo of a family of murine interleukin-2/Fc and interleukin-10/Fc" Journal of the American Society of Nephrology, Williams and Wilkins, Baltimore, MD, vol. 4. No. 3, p. 636 (1993).
Watanabe et al., *Biol. Pharm. Bull*, 19(8):1059-1063 (1996).
Fanslow, et al., "Soluble Forms of CD40 Inhibit Biologic Responses of Human B Cells", The Journal of Immunology, Jul. 15, 1992, vol. 149, pp. 655-660.
Gayle, et al., "Cloning of a Putative Ligand for the T1/ST2 Receptor", The Journal of Biological Chemistry, Mar. 8, 1996, vol. 271, No. 10, pp. 5784-5789.
Steurer, et al., "Ex Vivo Coating of Islet Cell Allografts with Murine CTLA4/Fc Promotes Graft Tolerance", The Journal of Immunology, Aug. 1, 1995, vol. 155, No. 3, pp. 1165-1174.
International Search Report for International (PCT) Patent Application No. PCT/US00/19336, mailed Nov. 14, 2000.
Written Opinion for International (PCT) Patent Application No. PCT/US00/19336, mailed Jun. 15, 2001.
International Preliminary Examination Report for International (PCT) Patent Application No. PCT/US00/19336, mailed Dec. 19, 2001.
Curtis et al., *Proc. Natl. Acad. Sci. USA*, 68:5809-5813 (1991).
Robinson et al., *Proc. Natl. Acad Sci USA*, 95:5929-5934 (1998).
Shu et al., *Immunotechnology*, 1:231-241 (1995).

* cited by examiner

*Primary Examiner*—Gary B Nickol
*Assistant Examiner*—Xiaozhen Xie
(74) *Attorney, Agent, or Firm*—Sheridan Ross PC

(57) ABSTRACT

The present invention relates to novel methods for making fusion proteins comprising a cytokine or growth factor fused to an immunoglobulin domain. The growth factor/cytokine can be fused directly to an immunoglobulin domain or through a peptide linker. The purified growth factor/cytokine-IgG fusion proteins produced by the novel methods are biologically active and can be used to treat diseases for which the non-fused growth factor/cytokine are useful.

15 Claims, 1 Drawing Sheet

IMMUNOGLOBULIN FUSION PROTEINS

CROSS-REFERENCE TO RELATED APPLICATIONS

This application is a national stage application under 35 U.S.C. §371 of PCT Application No. PCT/US00/19336, filed 13 Jul. 2000, which was published in English and which claims the benefit of priority under 35 U.S.C. §119(e) to U.S. Provisional Application Ser. No. 60/143,458, filed Jul. 13, 1999.

FIELD OF THE INVENTION

This invention relates generally to methods for constructing chimeric proteins and more specifically to methods for constructing recombinant immunoglobulin fusion proteins.

BACKGROUND OF THE INVENTION

Prolonging the circulating half-lives of protein pharmaceuticals is of interest to patients and healthcare providers. Long acting protein therapeutics should require less frequent injections and can be effective at lower doses than proteins with shorter circulating half-lives. It is known that increasing the effective size of a protein can increase its circulating half-life by preventing removal of the protein by the kidney (Knauf et al., 1988; Mahmood, 1998). One method that can be used to increase the effective size of a protein is to use recombinant DNA technology to covalently fuse the protein of interest to a second protein. The larger fusion protein often has a longer circulating half-life than the non-fused protein (Capon et al., 1989; Zeng et al., 1995). One class of proteins that has been used frequently to create fusion proteins is immunoglobulins (Ig), which are major components of blood. Immunoglobulins occur in various classes known as IgG, IgM, IgA, IgD, and IgE (Roitt et al., 1989). Human IgGs can be further divided into various types known as IgG1, IgG2, IgG3 and IgG4, which are products of distinct genes. IgG1 is the most common immunoglobulin in serum (70% of total IgG) and has a serum half-life of 21 days (Capon et al., 1989; Roitt et al., 1989). Although less abundant, IgG4 also has a long circulating half-life of 21 days (Roitt et al., 1989)

Human IgGs have a multidomain structure, comprising two light chains disulfide-bonded to two heavy chains (referred to herein as a "tetramer"; reviewed in Roitt et al., 1989). Each light chain and each heavy chain contains a variable region joined to a constant region. The variable regions are located at the N-terminal ends of the light and heavy chains. The heavy chain constant region is further divided into CH1, Hinge, CH2 and CH3 domains. The CH1, CH2 and CH3 domains are discreet domains that fold into a characteristic structure. The Hinge region is a region of considerable flexibility. Flexibility of the hinge can vary depending upon the IgG isotype (Oi et al., 1984; Dangl et al., 1988). IgG heavy chains normally form disulfide-linked dimers through cysteine residues located in the Hinge region. The various heavy chain domains are encoded by different exons in the IgG genes (Ellison et al., 1981; 1982).

Proteins have been fused to the heavy chain constant region of IgGs at the junction of the variable and constant regions (thus containing the CH1-Hinge-CH2-CH3 domains—referred to herein as the IgG-$C_H$ fusions) at the junction of the CH1 and Hinge domains (thus containing the Hinge-CH2-CH3 domains—referred to herein as IgG-Fc fusions), and at the C-terminus of the IgG heavy chain (referred to herein as IgG-C-terminal fusions).

IgG fusion proteins have been created most often with the extracellular domains of cell surface receptors (reviewed in Chamow and Ashkenaki, 1996). Examples of extracellular domains of cell surface receptors that have been joined using recombinant DNA technology to the $C_H$ or Fc domains of human or mouse IgGs include CD4 (Capon et al., 1989), tumor necrosis factor receptors (Mohler et al., 1993), CTLA4 (Linsley et al., 1991a), CD80 (Linsley et al., 1991b), and CD86 (Morton et al., 1996). Extracellular domains of receptors evolved to function when fused to other amino acids, i.e., the transmembrane and intracellular domains of the receptor, therefore it is not surprising that extracellular domains retain their ligand binding properties when fused to other protein domains such as IgG domains. Despite this, differences in ligand binding properties have been noted for certain extracellular domains. For example, a fusion protein comprised of the extracellular domain of CD4 to human IgG1-$C_H$ had 2-fold reduced affinity for the CD4 ligand gp120 than non-fused CD4 (Capon et al., 1989).

There are far fewer examples of proteins that are normally soluble, e.g., growth factors, cytokines and the like, which have been fused to IgG domains and retained full biological activity. Soluble proteins did not evolve to function when fused to other proteins and there is no reason to expect them to retain biological activity when fused to other proteins. In fact, in the majority of the published examples, biological activity of the fused cytokine/growth factor was significantly reduced relative to the non-fused cytokine/growth factor. Whether or not the cytokine/growth factor will function properly when fused to another protein will depend upon many factors, including whether the amino-terminus or carboxy-terminus of the cytokine/growth factor is exposed on the surface of the protein, whether these regions are important for biological activity of the cytokine/growth factor and whether the cytokine/growth factor is able to fold properly when fused to another protein. By their very nature, such factors will be highly protein-specific and unpredictable. Results with the few growth factor/cytokine fusion proteins that have been studied have shown how protein-specific biological activity of the fusion protein can be. In the majority of cases, biological activity of the fused growth factor/cytokine is severely reduced, whereas, in the minority of cases full biological activity of the growth factor/cytokine is retained. In one case where biological activity of the fusion protein was significantly reduced, modifying the amino acids at the junction between the cytokine/growth factor and the IgG domain resulted in a fusion protein with improved biological activity (Chen et al., 1994) This same modification did not improve biological activity of a second cytokine fused to the same IgG domain. [(Chen et al., 1994)

Growth factors that have been fused to IgGs include keratinocyte growth factor (KGF), fibroblast growth factor (FGF) and insulin-like growth factor (IGF-I). A KGF-mouse IgG1-Fc fusion protein was created by LaRochelle et al. (1995). On a molar basis, the fusion protein was 4-5-fold less active than KGF in stimulating proliferation of Balb/MK cells in an in vitro bioassay. The KGF-IgG-Fc fusion also had approximately 10-fold lower affinity for the KGF receptor on cells than did KGF. A fibroblast growth factor-human IgG-Fc fusion was constructed by Dikov et al. (1998). On a molar basis the FGF-IgG1-Fc fusion protein was approximately 3-fold less active than FGF in in vitro assays in stimulating DNA synthesis in NIH 3T3 cells. Shin and Morrison (1990) fused IGF-I to the C-terminus of IgG and found that the IGF-I-IgG C-terminal fusion protein had less than 1% of the in vitro biological activity IGF-I.

Examples of cytokines that have been fused to IgG domains include IL-2, IL-4, IL-10 and GM-CSF. Landolphi (1991; 1994) described an IL-2-IgG1-$C_H$ fusion protein, which included an extra serine between the C-terminus of IL-2 and the N-terminus of the IgG-$C_H$ domain. The IL-2-IgG1-$C_H$ fusion protein was purported to be as active, on a molar basis, in in vitro bioassays as IL-2, but no details were provided as to how protein concentrations were quantitated (Landolphi, 1991; 1994). Zeng et al. (1995) fused mouse IL-10 directly to the Fc region of mouse IgG2a; however the first amino acid of the Fc hinge region was changed from Glu to Asp. Zeng et al (1995) reported that the IL-10-IgG2a fusion protein was fully active in in vitro bioassays; however, only two concentrations of the fusion protein were studied, both of which were saturating. Given these high protein concentrations, only major differences (e.g., 100-fold) in bioactivities between the IL-10-mouse IgG2a fusion protein and IL-10 could have been detected. To detect smaller differences in bioactivities, one needs to analyze serial dilutions of the proteins in in vitro bioassays and calculate $EC_{50}$s (the concentration of protein required for half-maximal stimulation) or $IC_{50}$s (the concentration of protein required for half-maximal inhibition). $EC_{50}$s of the IL-10-IgG2a and IL-10 were not reported by Meng et al. (1995). Chen et al. (1994) also constructed an IL-2-IgG fusion protein and reported that this fusion protein was fully active. Gillies et al. (1993) also reported creating a fully active IL-2 fusion protein comprising IL-2 fused to the C-terminus of an antiganglioside IgG antibody. Unexpectedly, Gillies et al. (1993) found that a fusion between the same antibody and GM-CSF displayed only 20% of wild type GM-CSF bioactivity. Chen et al. (1994) were able to create a fully active IgG-C-terminal-GM-CSF fusion protein by inserting four amino acids between the antibody molecule and GM-CSF. Unexpectedly, they reported that fusion of IL-4 to the same antibody using the same four amino acid linker resulted in an IL-4 protein with 25-fold reduced biological activity (Chen et al., 1994).

Qiu et al. (1998) described homodimeric erythropoietin (EPO) proteins in which two EPO proteins were fused together using flexible peptide linkers of 3-7 glycine residues. The peptide linker joined the C-terminus of one EPO protein to the N-terminus of the second EPO protein. In vitro bioactivities of the fusion proteins were significantly reduced (at least 4- to 10-fold) relative to wild type EPO (Qiu et al., 1998).

Thus, the literature indicates that the amino acids at the junction between the growth factor/cytokine domain and the IgG domain can have a profound influence on the biological activity of the fused growth factor/cytokine.

For use as human therapeutics, it is desirable that bioactivity of a growth factor/cytokine-IgG fusion protein be as close to wild type, i.e., the non-fused protein, as possible. Fusion proteins with high activity can produce greater therapeutic benefits at lower doses than fusion proteins with lower specific activities. This will reduce the cost of medicines and provide patients with greater therapeutic benefits. For use as a human therapeutic it also is advantageous that the protein be as homogeneous and pure as possible. Ig fusion proteins are synthesized as monomers, which can assemble to form disulfide-linked dimers and tetramers, depending upon the type of fusion protein. The relative proportions of monomers, dimers and tetramers can vary from lot to lot, depending upon manufacturing conditions. Lot to lot variability can result in heterogeneous product mixtures with varying activities. Because of their larger size, tetramers are expected to have longer circulating half-lives in the body than dimers or monomers, and dimers are expected to have longer circulating half-lives than monomers. For this reason, tetramers, dimers and monomers may produce different therapeutic effects in vivo. Purified, homogeneous preparations of tetramers, dimers or monomers are preferred as therapeutics because they will have defined specific activities. For use as human therapeutics it also may be beneficial to keep the length of any linker sequence joining the growth factor/cytokine domain to the Ig domain to a minimum to reduce the possibility of developing an immune response to the non-natural amino acids in the linker sequence. Joining the two proteins without an intervening linker sequence, referred to herein as a "direct fusion", eliminates the possibility of developing an immune response to a non-natural linker and thus is one preferred form of an Ig fusion protein.

The literature on Ig fusion proteins merely provides examples for making "non-direct" cytokine/growth factor-Ig fusion protein, i.e., fusion proteins in which the growth factor/cytokine is joined to an Ig domain through a peptide linker. WO 99/02709 provides examples for joining EPO to an Ig domain by using a Bam HI restriction enzyme site to join DNA sequences encoding the proteins. This method can be used to create EPO-Ig fusion proteins containing linkers. Because Ban; HI has a specific DNA recognition sequence, GGATCC, which is not present at the junctions of the EPO or Ig-Fc, Ig-$C_H$ or light chain constant regions, this method is not useful for constructing EPO-Ig direct fusions.

EP 0464533A provides examples for making Ig fusion proteins that contain the specific three amino acid linker, AspProGlu, between the cytokine and Ig domains. The methods described in EP 0464533A rely on RNA splicing of separate exons encoding the cytokine and the Ig domain to create the fusion protein. The AspProGlu linker was required at the end of the cytokine/growth factor coding region because the RNA splicing reaction has specific sequence requirements at the splice site; the AspProGlu linker is encoded by nucleotides that may allow RNA splicing to occur. EP 0464533A provides an example for making an EPO-Ig fusion protein containing an AspProGlu linker using this method. The EPO coding region was modified to delete Arg 166 and add the amino acid linker, ProGlu, immediately following Asp165 of the EPO coding sequence. This resulted in the creation of an EPO-Ig fusion protein containing an AspProGlu linker (Asp165 of the EPO coding sequence provided the Asp of the linker sequence). The methods described by EP 0464533A are, therefore, not useful for creating Ig direct fusions or Ig fusions that do not contain AspProGlu or ProGlu linkers.

U.S. Pat. No. 5,349,053 describes methods for creating an IL-2-IgG-$C_H$ fusion protein that contains a Ser linker between the IL-2 and Ig domains. The methods described in U.S. Pat. No. 5,349,053 rely on RNA splicing of separate exons encoding the IL-2 and the IgG-$C_H$ domain. Because the RNA splicing reaction has specific sequence requirements at the splice site, the IL-2 coding region needed to be modified to add a TCA codon encoding serine to the carboxy terminus of the IL-2 coding region. The TCA codon was engineered to be followed by an intron splice junction sequence. This resulted in the creation of an IL-2-IgG-$C_H$ fusion protein containing a Ser linker. The methods described in U.S. Pat. No. 5,349,053 are not useful for creating cytokine/growth factor-Ig direct fusions, or cytokine/growth factor-Ig fusions that do not contain a Ser linker.

Growth factor/cytokine-IgG fusion proteins, including EPO-IgG and G-CSF-IgG fusion proteins, are contemplated in EP 0 464 533 A, WO99/02709 and Landolphi (1991; 1994). None of these references present any data regarding expression, purification and bioactivities of the contemplated EPO-IgG and G-CSF-IgG fusion proteins. Landolphi (1991;

1994) present bioactivity data for an IL-2-IgG1-$C_H$ fusion protein, but not for any other IgG fusion protein. The EPO-IgG1-Fc fusion protein contemplated by EP 0 464 533 A contains the two amino acid linker, ProGlu, between Asp 165 of the EPO coding sequence and the beginning of the IgG1-Fc hinge region. The carboxy-terminal amino acid in EN), Arg166 would be deleted. EP 0 464 533 A does not provide any information as to how the G-CSF coding region would be joined to the IgG1-Fc hinge region. Bioactivity data for neither protein is provided in EP 0 464 533. WO 99/02709 describes an EPO-mouse IgG2a-Fc fusion protein, but not an EPO-human IgG fusion protein. Bioactivity data for the EPO-mouse IgG2a-Fc fusion protein are not presented. WO 99/02709 also does not provide details as to the source of the EPO cDNA or human IgG genes used to construct the contemplated fusion proteins or the precise amino acids used to join EPO to the IgG domain. The reference cited in WO 99/02709 (Steurer et al., 1995) also does not provide this information.

WO 99/02709 postulates that a flexible peptide linker of 1-20 amino acids can be used to join EPO to an Ig domain; however the amino acids to be used to create the flexible linkers are not specified in WO 99/02709. Qiu et al. (1998) reported that EPO fusion proteins joined by flexible linkers of 3-7 glycine residues have significantly reduced biological activities (4-10-fold) relative to wild type EPO.

WO 99/02709 provides methods for using conditioned media from COS cells transfected with plasmids encoding hypothetical EPO-IgG fusion proteins to increase the hematocrit of a mouse. Such conditioned media will contain mixtures of monomeric and dimeric EPO-IgG fusion proteins as well as many other proteins. WO 99/02709 does not provide any evidence demonstrating that the methods taught are effective.

Thus, despite considerable effort, a need still exists for improved methods for creating growth factor/cytokine-Ig fusion proteins directly or with a variety of different linker types that preserve biological activity of the growth factor/cytokine domain of the Ig fusion protein. The present invention satisfies this need and provides related advantages.

SUMMARY OF THE INVENTION

Figure 1:
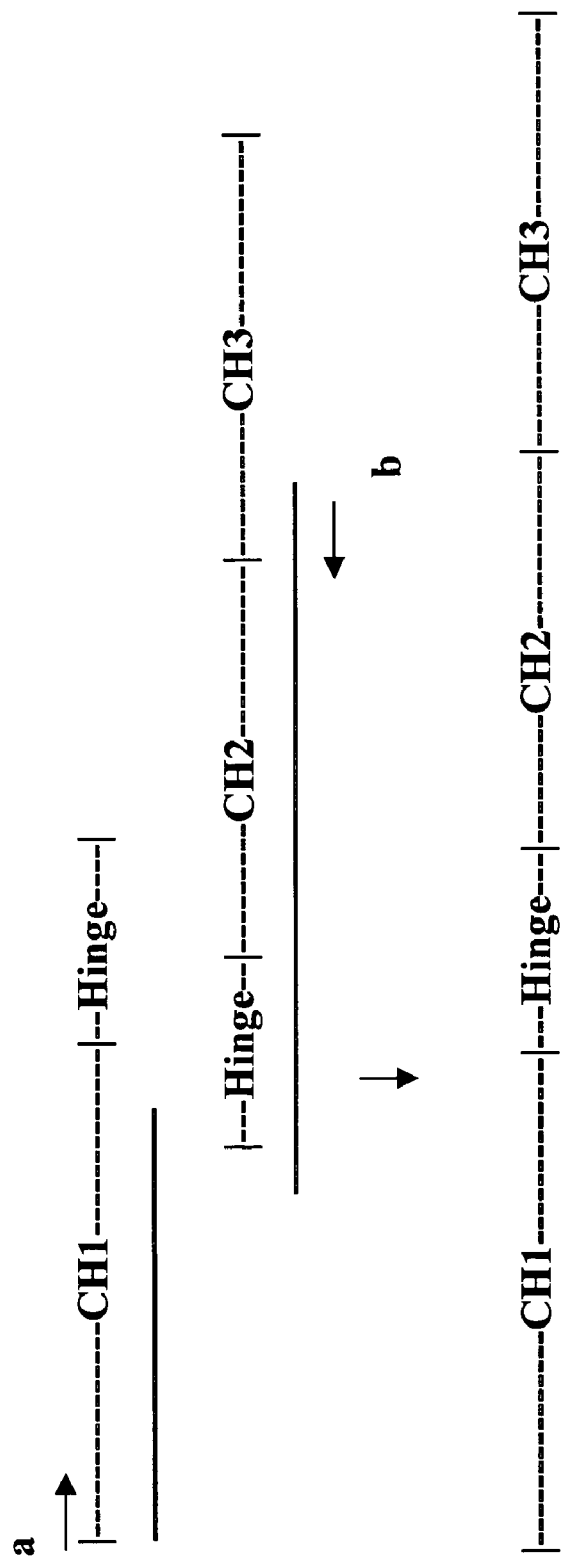
FIG. 1 is a diagram showing the amplification of two DNA fragments (CH1-Hinge and Hinge-CH2-CH3) that share a region of partial overlap (a portion of the Hinge region) using PCR and oligonucleotide primers a and b to generate a larger DNA fragment that includes CH1-Hinge-CH2-CH3.

The present invention discloses novel Ig fusion proteins in which a soluble protein is j fined directly to an Ig domain or by an amino acid linker that is not AspProGlu or Ser. The soluble protein is a growth factor, a cytokine or an active variant of a growth factor or cytokine. Useful linkers include a mixture of Glycine and Serine residues, preferably SerGly and Ser(G-lyGlySer)(SEQ.ID.NO.1), where n can be 1-7. The Ig domain preferably includes the constant region and is preferably selected from IgG-Fc, IgG-$C_H$ or $C_L$. Examples of growth factors and cytokines and their active fragments that substantially retain biological activity of the non-fused proteins when joined to Ig domains as direct fusions or through these linker sequences include members of the growth hormone (GH) supergene family such as, for example, G-CSF, EPO, GH, alpha interferon, beta interferon, gamma interferon, GM-CSF, IL-11, TPO, SCF and Flt3 ligand.

For example, EPO-IgG-Fc fusion proteins and G-CSF-IgG-Fc fusion proteins have biological activities, on a molar basis, equivalent to non-fused EPO and G-CSF. IgG-$C_H$ fusions of EPO and G-CSF surprisingly have in vitro biological activities within 2-4-fold of non-fused EPO and G-CSF. Growth Hormone-IgG-Fc and Growth Hormone-IgG-$C_H$ fusion proteins unexpectedly have biological activities within 4- to 17-fold of non-fused Growth Hormone. Similarly, biologically active IgG-Fc, IgG-$C_H$, and Ig-$C_L$ fusion constructs using IFN-α2 and IFN-β are also provided.

IgG-Fc fusions of EPO, G-CSF and Growth Hormone are more active than identical IgG-$C_H$ fusions of these growth factors/cytokines. Ig-$C_L$ fusions of IFN-α are more active than identical IgG-Fc or IgG-$C_H$ fusions of IFN-α. The bioactivity differences between IgG-Fc, IgG-$C_H$ and Ig-$C_L$ fusion proteins were also unexpected. In addition, preferred sites for constructing EPO-IgG, G-CSF-IgG, Growth Hormone-IgG, and IFN-α-Ig fusion proteins that Maximize bioactivity of the fused EPO, G-CSF, Growth Hormone and IFN-α domains have now been identified.

The invention further provides novel growth factor/cytokine-Ig fusion proteins comprising multimers of heavy and light chain fusion proteins as well as methods for preparing preparations of dimeric growth factor/cytokine-Ig fusion proteins that are essentially free of monomeric fusion proteins, aggregates and contaminating proteins. "Essentially free" is used herein to mean at least 90% pure. The invention also provides novel multimeric growth factors/cytokines where two or more cytokines/growth factors are joined as direct fusions or by using an amino acid linker.

Methods of treating various conditions are also provided in which an effective amount of an Ig fusion protein of the present invention are administered to a patient in need of such therapy.

DETAILED DESCRIPTION OF THE INVENTION

In work described herein, it has now been discovered that bioactivities of growth factor/cytokine-Ig fusion proteins can vary depending upon the isotype of the IgG domain, where the growth factor/cytokine is attached to the IgG domain, and whether the protein is attached to the constant region of an Ig light chain or an Ig heavy chain. These results were not predicted from the literature. Although not wishing to be bound by any particular theory, the inventors postulate that the bioactivity variability they observed may relate to the flexibility and other physical properties of the region in the Ig domain used to join to the fusion proteins. Based upon these findings, it is believed that bioactivity of an Ig fusion proteins created using mouse Ig domains cannot be used to predict bioactivity of a Ig fusion proteins created human Ig domains.

Accordingly, the invention generally relates to novel methods for constructing Ig fusion proteins comprising a soluble protein joined to an Ig domain and to the novel Ig fusion proteins obtained by the methods. The methods involve the joining of a soluble protein to an Ig domain as a direct fusion or with an intervening amino acid linker.

The methods of the present invention are useful for constructing Ig fusion proteins containing one or more growth factors and/or cytokines, including, without limitation, EPO, Growth Hormone (GH), G-CSF, IL-11, thrombopoietin (TPO), Stem Cell Factor, Flt3 Ligand, GM-CSF and interferon, especially alpha, beta and gamma interferon. Other proteins for which the methods are useful include other members of the GH supergene family. Members of the GH supergene family include GH, prolactin, placental lactogen, erythropoietin (EPO), thrombopoietin (TPO), interleukin-2 (IL-2), IL-3, IL-4, IL-5, IL-6, IL-7, IL-9, IL-10, IL-12 (p35 subunit), IL-13, IL-15, oncostatin M, ciliary neurotrophic factor, leukemia inhibitory factor, alpha interferon, beta interferon, gamma interferon, omega interferon, tau interferon, granulocyte-colony stimulating factor (G-CSF), granulocyte-macrophage colony stimulating factor (GM-CSF), macrophage colony stimulating factor (M-CSF), cardiotrophin-1 (CT-1), Stem Cell Factor and the flt3/flk2 ligand (Bazan (1990; 1991; 1992; Mott and Campbell (1995); Silvennoinen and Ihle (1996); Martin et al., 1990; Hannum et al., 1994). It is anticipated that additional members of this gene family will be identified in the future through gene cloning and sequencing. Members of the GH supergene family have similar secondary and tertiary structures, despite the fact that they generally have limited amino acid or DNA sequence identity. The shared structural features of members of the GH supergene family, which are described in Bazan (1990; 1991; 1992), Mott and Campbell (1995) and Silvennoinen and Ihle (1996), allow new members of the gene family to be readily identified. The methods described herein also are useful for creating Ig fusion proteins with proteins that are normally soluble and are not members of the GH supergene family. Active variants of these proteins can also be used in constructing the Ig fusion proteins of the present invention. The term "active variant" means a fragment of a soluble protein that substantially retains the biological activity of the full length protein and is described in more detail below.

The methods disclosed herein also can be used to join a growth factor/cytokine to an Ig domain using a linker of any amino acid sequence and of any length as long as the linkers are not AspProGlu or Ser. Preferred linkers are 1-50 amino acids in length, and more preferably 1-22 amino acids in length. Preferably the linker will not adversely affect bioactivity of the growth factor/cytokine or Ig domain. Preferred linkers contain mixtures of glycine and serine residues. Other amino acids that could be incorporated into useful linkers include threonine and alanine residues. One preferred linker disclosed herein is the two amino acid linker SerGly. Other preferred linkers disclosed herein are linkers of the motif Ser(GlyGlySer)$_n$(SEQ.ID.NO.1) where n can be 1-7.

The Ig domains of the present invention include the constant region such as, for example, an IgG-Fc, IgG-C$_H$, an Fc or C$_H$ domain from another Ig class, i.e., IgM, IgA, IgE, IgD or a light chain constant domain. Truncations and amino acid variants or substitutions of these domains also are included in this invention.

In another aspect of the invention, IgG-Fc and IgG-C$_H$ fusion proteins, for example, are synthesized as monomers that can assemble to form dimers. Typically, the dimers are joined by disulfide bonds in the IgG Hinge region. Conditioned media from cells secreting the IgG fusion proteins can contain mixtures of IgG fusion protein monomers and dimers. For use as human therapeutics it will be desirable to use homogeneous populations of either IgG fusion protein monomers or dimers, but not mixtures of the two forms. Methods for obtaining essentially pure preparations of dimeric growth factor/cytokine-IgG fusion proteins are also provided. The methods are generally accomplished by obtaining a host cell capable of expressing the IgG fusion protein, collecting the conditioned media, and purifying the dimeric fusion protein from monomeric fusion protein, aggregates and contaminating proteins by column chromatography procedures. Suitable host cells for expressing the IgG fusion proteins include yeast, insect, mammalian or other eukaryotic cells. Preferably, the host cell is a mammalian cell, particularly COS or CHO cells.

In one embodiment, EPO is joined directly to an Ig-Fc domain, for example an IgG-Fc domain, and has an EC$_{50}$ less than 1,000 ng/ml, preferably less than 100 ng/ml, more preferably less than 10 ng/ml and most preferably less than 4 ng/ml. In another embodiment EPO is preferably joined to an IgG-Fc or IgG-C$_H$ domain through a peptide linker of 2 to 7 amino acids and has an EC$_{50}$ less than 1,000 ng/ml, preferably less than 100 ng/ml, more preferably less than 10 ng/ml and most preferably less than 4 ng/ml.

In another embodiment, G-CSF is joined directly to an Ig-Fc domain, for example an IgG-Fc domain, and has an EC$_{50}$ less than 300 ng/ml, preferably less than 30 ng/ml, more preferably less than 3 ng/ml and most preferably less than 300 pg/ml. In another embodiment G-CSF is preferably joined to an IgG-Fc or IgG-C$_H$ domain through a peptide linker of 2 to 7 amino acids and has an EC$_{50}$ less than 300 ng/ml, preferably less than 30 ng/ml, more preferably less than 3 ng/ml and most preferably less than 300 pg/ml.

In another embodiment, GH is joined to an Ig-Fc or Ig-C$_H$ domain, for example an IgG-Fc or IgG-C$_H$ domain, through a peptide linker of 2 to 7 amino acids and has an EC$_{50}$ less than 1,000 ng/ml, preferably less than 100 ng/ml, and most preferably less than 10 ng/ml.

In another embodiment, IFN-α is joined to an Ig-Fc or Ig-C$_H$ domain, for example an IgG-Fc or IgG-C$_H$ domain, through a peptide linker of 2 to 7 amino acids and has an IC$_{50}$ less than 1,000 ng/ml, preferably less than 100 ng/ml, more preferably less than 40 ng/ml and most preferably less than 10 ng/ml. In another embodiment IFN-α is joined to a light chain constant region though a peptide linker of 2 to 7 amino acids and the fusion protein has an IC$_{50}$ less than 100 ng/ml, preferably less than 10 ng/ml, more preferably less than 1 ng/ml and most preferably less than 100 pg/ml.

In another embodiment, IFN-β is joined to an IgG-Fc or IgG-C$_H$ domain through a peptide linker of 2 to 7 amino acids and has an IC$_{50}$ less than 10,000 ng/ml, preferably less than 1,000 ng/ml, more preferably less than 100 ng/ml and most preferably less than 30 ng/ml.

It has now been discovered that purified GH-, EPO- and G-CSF-IgG-C$_H$ fusion proteins have reduced specific activities in in vitro biological assays compared to the non-fused proteins and IgG-Fc fusion proteins. The invention further provides novel, multimeric IgG-C$_H$/Ig light chain constant domain fusion proteins with improved biological activities. The invention also relates to growth factor/cytokine-IgG fusion proteins in which the IgG domain has been altered to reduce its ability to activate complement and bind Fc receptors. The alteration of the IgG domain for this purpose is described in Example 6 below.

Novel multimeric growth factor and/or cytokine fusion proteins are also provided. In one embodiment two or more growth factors and/or cytokines are joined directly to each other without an intervening peptide linker. In another embodiment two or more growth factors and/or cytokines are joined to each other through a peptide linker of 1 to 50 amino acids, and more preferably through a peptide linker of 1 to 7 amino acids. Particularly useful linkers for this purpose include SerGly and Ser(GlyGlySer)$_n$(SEQ.ID.NO.1), where n can be 1-7.

This invention includes active variants of the proteins and immunoglobulin domains that possess some or all of the biological properties of the corresponding full length or wild-type proteins or immunoglobulin domains. Such variants include, but are not limited to, amino acid variants, amino acid substitutions, truncations, additions, changes in carbohydrate, phosphorylation or other attached groups found on natural proteins, and any other variants disclosed herein. In some cases the variants may possess additional properties, e.g., improved stability or bioactivity, not shared by the original protein. For example, Mark et al. (1984) disclose an IFN-β mutein in which cysteine at position 17 is replaced by serine. IFN-β (Ser-17) displays improved stability relative to wild type IFN-β. Similarly, replacing cysteine-125 of IL-2 yields a more stable IL-2 protein (Landolphi, 1991; 1994). Lu et al. (1992) disclose a G-CSF mutein in which cysteine at position 17 is replaced by serine. Kuga et al. (1989), Hanazono et al. (1990) and Okabe et al. (1990) describe additional G-CSF muteins with enhanced biological properties. Elliot and Byrne (1995) have described mutants of EPO with enhanced biological activities.

Methods of producing and purifying the Ig fusion proteins are also provided. Such methods are generally accomplished by obtaining a transformed or transfected host cell with at least one nucleic acid encoding a growth factor or a cytokine that is not IL-10 and an Ig domain. The host cell is cultured until the desired fusion protein is expressed, followed by the purification or isolation of the Ig fusion protein by any means known in the art or as described in the Examples below. In one embodiment, methods of purifying the fusion proteins include obtaining a composition containing recombinantly produced Ig fusion proteins and isolating the desired Ig fusion proteins from various contaminants using column chromatography procedures, for example, a sizing column with a desired molecular weight cutoff. The host cell can be any suitable prokaryotic or eukaryotic cell line known to those skilled in the art, including without limitation, bacterial, insect or mammalian cells. Particularly useful cells are eukaryotic cells, preferably mammalian cells, and more preferably COS or CHO cells.

The Ig fusion proteins produced by the present methods can be used for a variety of in vitro and in vivo uses. The proteins of the present invention can be used for research, diagnostic or therapeutic purposes that are known for their wildtype, natural, or previously known modified counterparts.

In vitro uses include, for example, the use of the protein for screening, detecting and/or purifying other proteins. The Ig fusion proteins described herein also are useful as diagnostic reagents for identifying cells expressing receptors for EPO, G-CSF and GH, GM-CSF, IL-11, TPO, SCF, Flt3 ligand and alpha, beta and gamma interferon. The Ig fusion proteins also are useful as in vitro reagents for studying cell proliferation and differentiation.

The Ig fusion proteins described herein can be used to treat the same human conditions as the non-fused proteins. For example, the EPO-IgG fusion proteins can be used to treat anemia resulting from kidney failure, chemotherapy, radiation and drug complications. The EPO-IgG fusion proteins also can be used to stimulate red blood cell formation in normal individuals who wish to enhance their red blood cell count or hematocrit prior to surgery. The G-CSF-IgG fusion proteins can be used to treat neutropenia resulting from chemotherapy, radiation and drug complications, for mobilization of progenitor cells for collection in peripheral blood progenitor cell transplants and for treatment of severe chronic neutropenia. The GH-IgG fusion proteins can be used to treat short stature and cachexia. The IFN-α-IgG fusion proteins can be used to treat viral diseases and cancer. The IFN-β-IgG fusion protein can be used to treat multiple sclerosis, viral diseases and cancer. The GM-CSF-IgG fusion proteins can be used to treat neutropenia resulting from chemotherapy, radiation and drug complications, for mobilization of progenitor cells for collection in peripheral blood progenitor cell transplants, for treatment of severe chronic neutropenia and as an adjuvant for cancer vaccines. The SCF-IgG and Flt3 ligand-IgG fusion proteins can be used to mobilize hematopoietic progenitor cells for collection in peripheral blood progenitor cell transplants. The IL-11-IgG and TPO-IgG fusion proteins can be used for treating thrombocytopenia.

The Ig fusion proteins described herein will possess longer circulating half-lives in patients, which will allow the fusion proteins to be administered less frequently and/or in effective lower doses than the non-fused proteins. Typically, GH and G-CSF are administered by daily injections and EPO is administered by thrice weekly injections. One skilled in the art can readily determine the appropriate dose, frequency of dosing and route of administration. Factors in making such determinations include, without limitation, the nature and specific activity of the protein to be administered, the condition to be treated, potential patient compliance, the age and weight of the patient, and the like. The compounds of the present invention can also be used as delivery vehicles for enhancement of the circulating half-life of the therapeutics that are attached or for directing delivery to a specific target within the body.

Pharmaceutical compositions containing the Ig fusion proteins of the present invention in a pharmaceutically acceptable carrier are also provided. Those skilled in the art can readily identify such pharmaceutically acceptable carriers, which include without limitation physiological saline, Ringer's solution and the like. Other agents can also be included in the pharmaceutical compositions, including drugs, reagents, and therapeutic agents.

Detailed methods for constructing the Ig fusion proteins of the present invention are provided in the following examples, which are intended to illustrate without limiting the present invention.

Example 1

Construction of Growth Factor/Cytokine-IgG Gene Fusions

A. General Strategy.

Growth factor/cytokine (GF)-IgG gene fusions were constructed as described below. The general strategy employed for these constructions is outlined here and the specifics of individual cloning steps are detailed below. Cloning of the IgG4-$C_H$ coding sequence involved additional variations to the general strategy and these variations are described below. The human growth factor genes (GH, EPO and G-CSF) were cloned as cDNAs from various RNA sources detailed below. PCR primers used in these clonings added an optimized Kozak sequence (GCCACC; Kozak, 1991) and a Hind III restriction site to the 5' end of each these clones and a portion of a peptide linker (ser-gly-gly-ser) (SEQ.ID.NO.1) terminating in a Bam HI restriction site, to the 3' end of each of these clones. The growth factor genes were cloned as Hind III-Bam HI fragments into the mammalian cell expression vector pcDNA3.1 (+) (Invitrogen, Inc., San Diego, Calif.) and sequenced. In parallel, IgG coding sequences (IgG1-Fc, IgG1-$C_H$, IgG4-Fc, IgG4-$C_H$) were cloned from cDNAs generated from human leukocyte RNA. PCR forward primers used in these clonings incorporated a portion of a peptide linker (gly-ser-gly-gly-ser)(SEQ.ID.NO.2) containing a Bam HI restriction site at the 5' end of each of these clones. The reverse PCR primers were designed to anneal to the 3' untranslated regions of the IgG1 and IgG4 mRNAs (about 40 by downstream of the translational stop codon) and included an Xba I restriction site. The IgG coding sequences were cloned into pcDNA3.1(+) as Bam HI-Xba I fragments and confirmed by DNA sequencing. The fusion genes were then constructed by excising the IgG coding sequences as Bam HI-Xba I fragments and cloning these fragments into the pcDNA::GF recombinant plasmids that had been cut with Bam HI and Xba I. In the resulting pcDNA3.1 constructs the fusion genes are transcribed by the strong cytomeglovirus immediate early promoter present in pcDNA3.1(+) upstream of the cloned fusion gene. Ligation of the two fragments through the Bam HI site within the linker sequence results in a seven amino acid linker (ser-gly-gly-ser-gly-gly-ser)(SEQ.ID.NO.3) at the fusion junction.

B. Cloning of Growth Hormone, EPO and G-CSF

1. Cloning of human Growth Hormone: A cDNA encoding human Growth Hormone (GH) was amplified from human pituitary single-stranded cDNA (CLONTECH, Inc., Palo Alto, Calif.), using the polymerase chain reaction (PCR) technique and primers BB87 (5>GCAAGCTTGCCACCATGGCTACAGGCTCCCGGACG 3)(SEQ.ID.NO.4) and BB88 (5>CGCGGATCCTCCGGAGAA GCCACAGCTGCCCTCCAC>3)(SEQ.ID.NO.5). Primer BB87 anneals to the 5' end of the coding sequence for the hGH secretion signal, whereas the reverse primer, BB88, anneals to the 3' end of the GH coding sequence. The resulting ~680 by PCR product was digested with Hind III and Bam HI, gel purified and cloned into pcDNA3.1(+) vector (Invitrogen, Inc., Carlsbad, Calif.) that had been digested with Hind III and Bam HI, alkaline phosphatase treated, and gel purified. A clone with the correct DNA sequence (Martial et al., 1979; Roskam and Rougeon, 1979; Seeburg, 1982; DeNot et al., 1981) was designated pcDNA3.1(+)::GHfus or pBBT159.

2. Cloning of human Erythropoietin. A cDNA encoding human erythropoietin (EPO) was cloned by PCR using forward primer BB45 (5>CCCGGAT CCATGGGGGTGCACGAATGTCCTG>3) (SEQ.ID.NO.6) and reverse primer BB47 (5>CCCGAAITCTATGCCCAGGT GGACACACCTG>3) (SEQ.ID.NO.7). BB45 anneals to the DNA sequence encoding the initiator methionine and amino terminal portion of the EPO signal sequence and contains a Bam HI site for cloning purposes. BB47 anneals to the 3' untranslated region of the EPO mRNA immediately downstream of the translational stop signal and contains an Eco RI restriction site for cloning purposes. Total RNA isolated from the human liver cell line Hep3B was used in first strand synthesis of single-stranded cDNA for PCR. For preparation of total cellular RNA, Hep3B cells (available from the American Type Culture Collection, Rockville, Md.) were grown in Delbecco's Modified Eagle's media (DMEM) supplemented with 10% fetal bovine serum (FBS). EPO expression was induced by treating the cells for 18 h with 130 µM Deferoxamine or 100 µM cobalt chloride (Wang and Semenza, 1993). RNA was isolated from the cells using an RNeasy Mini kit (Qiagen, Santa Clarita, Calif.), following the manufacturer's directions. Approximately 320 µg of total RNA was isolated from $1.4 \times 10^7$ cells treated with cobalt chloride and 270 µg of total RNA isolated from $1.4 \times 10^7$ cells treated with Deferoxamine.

First strand synthesis of single-stranded cDNA was accomplished using a 1st Strand cDNA Synthesis Kit for RT-PCR (AMV) from Boehringer Mannheim Corporation (Indianapolis, Ind.) and random hexamers were used as the primer. Subsequent PCR reactions using the products of the first strand syntheses as templates were carried out with primers BB45 and BB47. The expected approximately (~) 600 by PCR product was observed when reaction products were run out on an agarose gel. Both RNA preparations yielded an EPO PCR product. The PCR product was digested with Bam HI and Eco RI and cloned into vector pUC19 that had been cut with Bam HI and Eco RI and treated with alkaline phosphatase. DNA sequencing identified a clone containing the correct coding sequence for the EPO gene. This plasmid was designated pBBT131.

Plasmid pBBT131 was used as template in a PCR reaction with primers BB89 (5>CGCAAGC7TGCCACCATGGGGGTGC ACGAATGTCCT>3) (SEQ.ID.NO.8) and BB90 (5>CGCGGATCCTCCGGATCTGTCCCCTGTCCTGCAGGC>3)(SEQ.ID.NO.9) to construct a modified EPO cDNA suitable for fusion with IgG genes. Primer BB89 anneals to the 5' end of the coding sequence for the EPO secretion signal and the reverse primer, BB90, anneals to the 3' end of the EPO coding sequence. The resulting ~610 by PCR product was digested with Hind III and Bam HI, gel purified and cloned into pcDNA3.1(+) vector that had been digested with Hind III and Bam HI, alkaline phosphatase treated, and gel purified. A clone with the correct DNA sequence (Lin et al., 1985) was designated pcDNA3.1(+)::EPOfus or pBBT176.

Similar procedures can be used to create modified EPO cDNAs in which Arg166 is deleted. In this case a primer with the sequence (5>CGCGGATCCTCCGGATCTGTCCCCTGTCCTG CAGGCCTC>3)(SEQ.ID.NO.10) can be used in place of primer BB90.

3. Cloning of human Granulocyte Colony-Stimulating Factor. A cDNA encoding human Granulocyte Colony Stimulating Factor (G-CSF) was amplified by PCR from total RNA isolated from the human bladder carcinoma cell line 5637 (available from the American Type Culture Collection, Rockville, Md.). The cells were grown in Roswell Park Memorial Institute (RPMI) 1640 media supplemented with 10% FBS, 50 units/ml penicillin and 50 µg/ml streptomycin. RNA was isolated from the cells using an RNeasy Mini RNA isolation kit purchased from Qiagen, Inc. (Santa Clarita, Calif.) following the manufacturer's directions. Approximately 560 µg of total RNA was isolated from $4.5 \times 10^7$ cells. First strand synthesis of single-stranded cDNA was accomplished using a 1st Strand cDNA Synthesis Kit for RT-PCR (AMV) from Boehringer Mannheim Corp (Indianapolis, Ind.) and random hexamers were used as the primer. Subsequent PCR reactions using the products of the first strand synthesis as template were carried out with forward primer BB91 (5>CGCAAGCTTGCCACCATGGCTGGACC TGCCACCCAG>3) (SEQ.ID.NO.11) and reverse primer BB92 (5>CGCGGATCCTCCGGAGGGCTGGGCAAGGTGGCGTAG>3)(SEQ.ID.NO.12). Primer BB91 anneals to the 5' end of the coding sequence for the G-CSF secretion signal and the reverse primer, BB92, anneals to the 3' end of the G-CSF coding sequence. The resulting ~640 bp PCR product was digested with Hind III and Bam HI, gel purified and cloned into pcDNA3.1(+) vector that had been digested with Hind III and Bam HI, alkaline phosphatase treated, and gel purified. A clone with the correct DNA sequence (Souza et al., 1986; Nagata et al., 1986a,b) was designated pcDNA3.1(+)::G-CSFfus or pBBT165.

C. Cloning of IgG Coding Sequences.

1. Cloning of IgG1-Fc coding sequences. A cDNA encoding IgG1-Fc (hinge-CH2-CH3 domains) was amplified from human leukocyte single-stranded cDNA (CLONTECH, Inc., Palo Alto, Calif.) by PCR using primers BB83 (5>CGCGGATCCG GTGGCTCAGAGCCCAAATCTTGTGACAAAACT>3)(SEQ.ID.NO.13) and BB82 (5>CGCTCTAG AGGTACGTGCCAAGCA TCCTCG>3) (SEQ.ID.NO.14).

Forward primer BB83 anneals to the 5' end of the coding sequence of the hinge domain of IgG1, whereas the reverse primer BB82 anneals to the 3' untranslated region of IgG1 and IgG4 mRNA 45 by downstream of the translational stop codon. The IgG1 and IgG4 sequences are identical over the 21 by segment to which BB82 anneals. The 790 by PCR product was digested with Bam HI and Xba I, gel purified and cloned into pcDNA3.1(+) vector that had been digested with Bam HI and Xba I, alkaline phosphatase treated, and gel purified. Two clones were sequenced but each contained a single base pair substitution that resulted in an amino acid substitution mutation. Otherwise the sequences matched the published human IgG1 genomic DNA sequence (Ellison et al., 1982). The relative positions of the mutations in the two clones allowed us to use convenient unique restriction sites (Sac II in the CH2 domain of IgG1 and Bgl II in the pcDNA3.1(+) vector) to construct a full length IgG1-Fc clone in pcDNA3.1(+) via in vitro recombination. The resulting clone, which had the correct IgG1-Fc sequence, was designated pcDNA3.1(+)::fusIgG1-Fc or pBBT167.

2. Cloning fIgG4-Fc coding sequences. A cDNA encoding IgG4-Fc (hinge-CH2-CH3 domains) was amplified from human leukocyte single-stranded cDNA (CLONTECH) by PCR using primers BB84 (5>CGCGGATCCGG TGGCT-CAGAGTCCAAATATGGTCCCCCATGC>3) (SEQ.ID.NO.15) and BB82 (5>CGCTCTAG AGGTACGTGC-CAAGCA TCCTCG>3) (SEQ.ID.NO.14). Forward primer BB84 anneals to the 5' end of the coding sequence of the hinge domain of IgG4. The reverse primer BB82 is described above. The ~790 by PCR product was digested with Bam HI and Xba I and cloned into pcDNA3.1(+) that had been similarly digested. A clone with the correct DNA sequence (Ellison et al., 1981) was designated pcDNA3.1(+)::fusIgG4-Fc or pBBT158.

3. Cloning of IgG1-$C_H$ coding sequences. A cDNA encoding IgG1-$C_H$ (CH1-hinge-CH2-CH3 domains) was amplified from human leukocyte single-stranded cDNA (CLONTECH) by PCR using BB81 (5>CGCGGATCC GGTGGCTCAGC-CTCCACCAAGGGCCCATC>3)(SEQ.ID.NO.16) and BB82(5>CGCTCTAGAGGTACGTGCCAAGC ATC-CTCG>3) (SEQ.ID.NO.14). Forward primer BB81 anneals to the 5' end of the coding sequence of the CH1 domain of IgG1 and IgG4. The sequences at the 5' end of the CH1 domains of these two exons are almost identical: 19/20 nucleotides match. The reverse primer, BB82, is described above. The ~1080 by PCR product was digested with Bam HI and Xba I, gel purified and cloned into pcDNA3.1(+) that had been digested similarly. These primers in principle could amplify both IgG1 and IgG4 sequences. Since IgG1 is much more abundant in serum than IgG4 (Roitt et al., 1989) we expected that most clones would encode IgG1. The first two clones sequenced were IgG1 but each contained a single base pair substitution that resulted in an amino acid substitution mutation. Otherwise the sequences obtained matched the published human IgG1 genomic DNA sequence (Ellison et al., 1982). The relative positions of the mutations in the two clones allowed us to use convenient unique restriction sites (Age I in the CH1 domain of IgG1 and Bst BI in the pcDNA3.1(+) vector) to construct a full length IgG1-$C_H$ clone in pcDNA3.1(+) via in vitro recombination. A clone with the correct IgG1-$C_H$ sequence was designated pcDNA3.1(+)::fusIgG1-$C_H$ or pBBT166.

4. Cloning of IgG4-$C_H$ coding sequences. The near identity of the DNA sequences encoding the 5' ends of the IgG1 and IgG4 CH1 domains and the relatively low abundance of the IgG4 mRNA led to an alternative strategy for cloning the IgG4-$C_H$ coding sequences. PCR-based site directed mutagenesis was used to change the DNA sequence of the cloned IgG1 CH1 domain to match the amino acid sequence of the IgG4 CH1 domain. The CH1 domains differ at only 8 of 98 amino acids and these positions are clustered, so that one round of PCR using two mutagenic oligos can convert the IgG1 CH1 sequence into the IgG4 CH1 sequence. A second round of PCR added the Bam HI site and linker sequence to the 5' end of the IgG4 CH1 and 21 by of sequence from the IgG4 Hinge domain to the 3' end. The technique of "gene splicing by overlap extension" (Horton et al., 1993; Innis et al., 1990) was then employed to recombine the engineered IgG4 CH1 domain with the IgG4 Fc (Hinge-CH2-CH$_3$) sequence. In this technique two separate fragments sharing a segment of identical sequence, the "overlap", at one end are extended through the annealed overlap regions in a PCR reaction as diagrammed in FIG. 1.

To construct the IgG4 CH1 sequence, mutagenic primers BB119 (5>TCCACCAAG GGCCCATCCGT CTTC-CCCCTGGCGCCCTGCTCCAGGAGCAC-CTCCGAGAGC ACAGCC>3)(SEQ.ID.NO.17) and BB120 (5>TCTCTTG TCCACCTTGGTGTTGCTGGGCTTGT-GATC TACG'TTGCAGGTGTAGGTCTTCGTGCCCAA>3)(SEQ.ID.NO.18) were used in PCR reactions with pBBT166, which carries the cloned IgG1-$C_H$ sequence as described above. Forward primer BB119 anneals to the sequence encoding amino acids 2 through 23 of the CH1 domain and encodes 4 amino acid substitutions: S14C, K16R, G20E and G21S. Reverse primer BB120 anneals to the sequence encoding amino acids 76 through 97 of the CH1 domain and encodes 4 additional amino acid substitutions: Q79K, 182T, N86D and K97R. The ~290 by product of this PCR reaction was gel purified and used as template in a PCR reaction with primers BB81(see above; Example 1, C.3) and BB121 (5>TGGGGGACCATATTTG GACTCAACTCTCTTGTC-CACCTT>3) (SEQ.ID.NO.19). Reverse primer BB121 anneals to the 3' end of the CH1 domain of IgG4, adds amino acid 98 of the CH1 domain and 21 by extending into the Hinge domain of IgG4. The ~330 by product of this reaction was gel purified and used as one of the template molecules in the PCR splicing reaction. The other template for the splicing reaction was generated by PCR of the cloned IgG4-Fc sequence of pBBT158 (described above, Example 1, C.2.) with primers BB84 and BB82 which amplify the IgG4 Fc domain as described above. The resulting ~790 by product consists of the IgG4 hinge-CH2-CH3 sequence. This fragment was gel purified and used as one of the template molecules in the PCR splicing reaction. This reaction employed the primers BB81 and BB82 and generated a full-length "spliced" product of 1075 bp. To minimize the DNA sequencing required to confirm this product, the PCR fragment was digested with Bam HI and Sac II and the ~530 by fragment (containing the complete CH1 and hinge domains and a portion of the CH2 domain) was cloned into pBC-SK+ (Stratagene) for sequencing. The sequence of the Bam HI-Sac II fragment was confirmed for one clone which was the designated pBBT182. The Bam HI-Sac II fragment of pBBT182 was then used convert the GFIgG4-Fc clones to full length GFIgG4-$C_H$ clones as detailed below.

D. Construction of Growth Hormone-, EPO- and G-CSFIgG Fusions.

Most (9/12) of the EPO-, G-CSF- and GH-IgG gene fusions were generated by excising the IgG coding sequences cloned in pcDNA3.1(+) as Bam HI-Xba I fragments and cloning these fragments into the pcDNA::[GF] recombinant plasmids which had been cut with Bam HI and Xba I. The fusions of the three growth factor genes to IgG4-$C_H$ were constructed by excising the ~530 bp Bam HI-Sac II fragment of pBBTI 82 and replacing the ~240 by Bam HI-Sac II fragments of the three pcDNA::[GF]-IgG4-Fc clones with this ~530 by Bam HI-Sac II fragment. The resulting plasmids and the GF-IgG fusion proteins they encode are listed in Table 1.

E. G-CSF (C17S)-IgG Fusion Proteins

G-CSF-IgG fusions in which cysteine-17 f G-CSF is replaced by serine [G-CSF (MS)] can be constructed by PCR mutagenesis using the following two oligonucleotide primers: C17S-F (5'TTCCTGCTCAAGTCCTTAGAG-CAAGTG-3')(SEQ.ID.No.20) and C17S-R (5'CACT-TGTCTAAGGACTTGAGCAGGAA-3')(SEQ.ID.NO.21). For example, a G-CSF (C17S)-IgG1-Fc fusion can be constructed by performing two separate PCR reactions using pBBT174 as template. One reaction can use oligo C17S-F in combination with BB82. The second PCR reaction can use oligo C17S-R in combination with BB91. The PCR products of these reactions can be gel-purified, mixed and reamplified with BB82 and BB91. The ~1300 by product can be digested with HindIII and PflMI, the HindIII/PflMI band gel-purified, and cloned into similarly cut plasmid pBBT174. After transformation of E. coli DH5α, a plasmid clone containing the C17S mutation can be identified by DNA sequencing. Similar mutagenesis procedures can be used to change cysteine-17 to another amino acid by substituting the appropriate nucleotides (sense and antisense nucleotides encoding the desired amino acid) for the underlined nucleotides in oligos C17S-F and C17S-R.

Example 2

Expression and Purification of GF-IgG Fusion Proteins

A. Small Scale Transfection of COS Cells

Expression and bioactivity of the GF-IgG fusion proteins were assessed initially by small-scale transfection of COS cells. Endotoxin-free plasmid DNAs were prepared using an "Endo-Free Plasmid Purification Kit" (Qiagen, Inc.) according to the vendor protocol and used to transfect COS-1 cells (available from the American Type Culture Collection, Rockville, Md.). The COS-1 cells were grown in Delbecco's Modified Eagle's Media supplemented with 10% FBS, 50 units/ml penicillin, 50 µg/ml streptomycin and 2 mM glutamine (COS cell growth media). Initial transfection experiments were carried out in Costar 6 well tissue culture plates (VWR Scientific) using the following protocol. Briefly, 2-3×10$^5$ cells were seeded into each well in 2 ml of COS cell growth media and allowed to incubate overnight at 37° C. and 5% $CO_2$ by which time the cells had reached 50-60% confluency. For each well, 0.8 µg of plasmid DNA was complexed with 6 µl of LipofectAMINE reagent (Gibco BRL, Gaithersburg, Md.) in 186 µl of OPTI-MEM I Reduced Serum Medium (Gibco BRL, Gaithersburg, Md.) for 30-45 minutes at room temperature. COS-1 cells were washed one time with 2 ml of OPTI-MEM I per well and then 1.8 ml of OPTI-MEM I was added to each well. The complex mixture was then added to the well and left at 37° C., 5% $CO_2$ for approximately 4-5 hours. After the incubation period, the mixture was replaced with 2 ml of COS cell growth media per well and left overnight at 37° C., 5% $CO_2$. The next day the cells were washed twice with 2 ml of DMEM (no additives) per well. Following the wash steps, 2 ml of serum-free COS cell growth media was added to each well and the cells left at 37° C., 5% $CO_2$. Conditioned media containing the GF-IgG-fusion proteins were harvested after 72 hours and analyzed by SDS-PAGE and Western blot to confirm expression of the GF-IgG-fusion proteins. The parent plasmid, pcDNA 3.1(+) (Invitrogen) was used as a negative control. Transfection efficiency was estimated to be ~15%, using pCMV3 (Clontech), which expresses E. coli β-galactosidase. Transfected cells expressing β-galactosidase were identified using a β-Gal Staining Set (Boehringer Mannheim, Indianapolis, Ind.).

Samples of the conditioned media were prepared in SDS-PAGE sample buffer with the addition of 1% β-mercaptoethanol (BME) when desirable and electrophoresed on precast 14% Tris-glycine polyacrylamide gels (Novex). Western blots using appropriate antisera demonstrated expression of all of the GF-IgG fusion proteins. The GH-IgG fusion proteins were detected using a polyclonal rabbit anti-synthetic-hGH antiserum (kindly provided by Dr. A. F. Parlow and the National Hormone and Pituitary Program). The EPO- and G-CSF-IgG fusion proteins were detected using polyclonal antisera purchased from R&D Systems (Minneapolis, Minn.). Serial dilutions of the conditioned media were analyzed in the appropriate in vitro bioassays described later. These assays demonstrated significant activity in the conditioned media.

B. Large Scale Transfection of COS-1 Cells

Large scale transfections were carried out using Corning 100 mm tissue culture dishes or Corning T-75 tissue culture flasks (VWR Scientific). For 100 mm dishes, 1.6×10$^6$ cells were plated in 10 ml of COS cell growth media per dish and incubated at 37° C., 5% $CO_2$ overnight. For each 100 mm dish, 6.7 µg of endotoxin-free plasmid DNA was complexed with 50 µl of LipofecAMINE reagent in 1.5 ml of OPTI-MEM I for 30-45 minutes at room temperature. The COS-1 cells were washed one time with 10 ml OPTI-MEM per dish and then replaced with 6.6 ml of OPTI-MEM I. Following complex formation, 1.67 ml of the complex was added to each dish and left at 37° C., 5% $CO_2$ for 45 hours. After the incubation period, the reaction mixture was replaced with 10 ml of serum containing COS cell growth media per dish and left at 37° C., 5% $CO_2$ overnight. The next day the cells were washed twice with 10 ml of DMEM (no additives) per dish. Following the wash steps, 10 ml of serum-free COS cell growth media was added to each dish and incubated at 37° C., 5% $CO_2$. Conditioned media were harvested routinely every three days (on days 3, 6, 9 and 12) and fresh serum-free COS cell growth media added to the cells. Transfections in T-75 culture flasks were identical to the 100 mm dish protocol with the following exceptions: Cells were plated at 2×10$^6$ cells per flask and 935 µg of endotoxin-free plasmid DNA was complexed with 70 µl of LipofectAMINE reagent in 2.1 ml of OPTI-MEM I for each T-75 flask. Following complex formation, 2.3 ml of the complex was added to each flask containing 7.7 ml of OPTI-MEM I. Transfection efficiency was determined to be ~15% using pCMVβ and staining for β-galactosidase expression as described earlier. The 12 plasmids listed in Table 1 were transfected into COS-1 cells using the large-scale format to generate protein for purification. The conditioned media were clarified by centrifugation and stored at −80° C. for later purification. Western blots were used to confirm expression of the IgG-fusion proteins.

C. Purification of GF-IgG-Fusion Proteins

Approximately 300 ml of transfected COS-1 cell conditioned media for each IgG-fusion protein was pooled and concentrated using an Ultrafiltration cell and either a YM3 or YM30 DIAFLO Ultrafiltration membrane (Amicon, Beverly, Mass.). Concentrated pools were then loaded into a 1 ml Pharmacia HiTrap recombinant Protein A column previously equilibrated with 20 mM NaPhosphate pH 7.0. The column was washed with 20 mM NaPhosphate until the $A_{280}$ had reached baseline. Bound protein was eluted with 100 mM NaCitrate pH 3.0 and collected into sufficient 1M Tris pH 9.0 to achieve a final pH of approximately 7.0. Each fusion protein was purified using a dedicated column to avoid any possibility of cross-contamination. All of the IgG fusion proteins chromatographed similarly, yielding a single peak in the elution step. Column fractions were analyzed using 8-16% precast Tris-glycine SDS-PAGE and fractions enriched for the IgG-fusion protein were pooled. Protein concentrations of the pooled fractions were determined by Bradford assay (Bio-Rad Laboratories, Richmond, Calif.) using bovine serum albumin (BSA) as the standard.

The purified GF-IgG fusion proteins were analyzed by SDS-PAGE under reducing and non-reducing conditions and stained with Coomassie blue. All of the GF-IgG fusion proteins were recovered principally as disulfide-linked dimers (typically, >90% of the recovered IgG fusion proteins were dimeric). The apparent molecular weights of the proteins ranged from 115-190 kDa kDa under non-reducing conditions (disulfide-linked dimers) and 50-75 kDa under reducing conditions (monomers), and were largely consistent with the molecular weights predicted in Table 1. The size differences between monomers and dimers allowed monomers and dimers to be easily distinguished by SDS-PAGE. The apparent molecular weights of the monomeric and dimericGH-IgG-Fc fusion proteins were approximately 50 kDa and 115 kDa, respectively. The apparent molecular weights of the monomeric and dimericG-CSF-IgG-Fc fusion proteins also were approximately 50 kDa and 115 kDa, respectively. The apparent molecular weights of the dimeric IgG-$C_H$ fusions were larger than expected: approximately 160 kDa for the GH-IgG-$C_H$ and G-CSF-IgG-$C_H$ fusions and approximately 180 kDa for the EPO-IgG-$C_H$ fusions. The EPO-IgG-$C_H$ fusion monomer also was larger than expected, possessing an apparent molecule weight of approximately 74 kDa. The molecular weights of the EPO-IgG-Fc fusion proteins also were larger than predicted (apparent monomer and dimer molecular weights of 62 kDa and 130 kDa, respectively). The larger than expected sizes of the EPO-Ig fusion proteins presumably are due to extensive glycosylation of the EPO domain. Monomeric fusion proteins were present in all of the purified protein samples, but were more abundant with the IgG4 fusion proteins. The sizes of the major IgG fusion protein bands were different from the molecular weights of bovine IgG, indicating that the proteins purified were not contaminating bovine IgGs from serum used in the experiments. The major IgG fusion protein bands also reacted with antisera specific for GH, EPO and G-CSF in Western blots of the samples. Purity of the IgG fusion proteins was estimated to be at least 90% from Coomassie blue staining of the gels.

All of the GF-IgG-$C_H$ fusions contained a large aggregate that migrated at the top of the gel when the samples were analyzed under non-reducing conditions. This aggregate disappeared when the samples were analyzed under reducing conditions and the amount of protein at the molecular weight of the major GF-IgG-$C_H$ bands seemed to increase proportionately. The aggregates also reacted with antisera specific for the various growth factors. These data suggest the aggregates are disulfide-linked multimers of the GF-IgG-$C_H$ fusion proteins. Under reducing SDS-PAGE conditions, all of the GF-IgG-$C_H$ fusions show a diffuse band approximately 20 kDa larger than the main GF-IgG-$C_H$ band. This band reacted with antisera against the growth factors and may be related to the aggregates.

TABLE 1

Predicted M lecular Weights and Recoveries of GF-IgG Fusion Proteins

| Expression Plasmid | IgG-Fusion Protein | Predicted Molecular Weight (kDa)[1] | |
|---|---|---|---|
| | | Monomer | Dimer |
| PBBT 171 | GH-IgG1-$C_H$ | 58,706 | 117,412 |
| PBBT 172 | GH-IgG1-Fc | 48,693 | 97,386 |
| PBBT 183 | GH-IgG4-$C_H$ | 58,541 | 117,082 |
| PBBT 163 | GH-IgG4-Fc | 48,365 | 96,730 |
| PBBT 173 | G-CSF-IgG1-$C_H$ | 55,564 | 111,128 |
| PBBT 174 | G-CSF-IgG1-Fc | 45,551 | 91,102 |
| PBBT 184 | G-CSF-IgG4-$C_H$ | 55,399 | 110,798 |
| PBBT 175 | G-CSF-IgG4-Fc | 45,222 | 90,444 |
| PBBT 179 | EPO-IgG1-$C_H$ | 54,972 | 109,944 |
| PBBT 180 | EPO-IgG1-Fc | 44,960 | 89,920 |
| PBBT 185 | EPO-IgG4-$C_H$ | 54,808 | 109,616 |
| PBBT 181 | EPO-IgG4-Fc | 44,632 | 89,264 |

[1]Does not include molecular weight contributions due to of glycosylation.

Example 3

In Vitro Bioactivities of Purified GF-IgG Fusion Proteins

A. General Strategy

Cell proliferation assays were developed to measure in vitro bioactivities of the IgG fusion proteins. The assays measure uptake and bioreduction of the tetrazolium salt MTS [3-(4,5-dimethylthiazol-2-yl)-5-3-carboxyphenyl)-2-(4-sulphenyl)-2H-tetrazolium]. In the presence of an electron coupler such as phenazine methosulfate (PMS), MTS is converted to a formazan product that is soluble in tissue culture media and can be measured directly at 490 nm. Cell number is linear with absorbance values up to about 2. For EPO and G-CSF we were able to use existing cell lines to develop the bioassays. For GH, we needed to create a cell line that proliferates in response to GH. Such a cell line was created by stably transforming a murine leukemia cell line with a rabbit GH receptor.

In general, the bioassays were set up by washing the appropriate cells three times with media (no additives) and resuspending the cells at a concentration of $0.7-1 \times 10^5$/ml in media with additives (media used for each cell line is given below). Fifty µl ($3.5-5 \times 10^3$ cells) of the cell suspension was aliquoted per test well of a flat bottom 96 well tissue culture plate. Serial dilutions of the protein samples to be tested were prepared in serum-containing media. Fifty µl of the diluted protein samples were added to the test wells and the plates incubated at 37° C. in a humidified 5% $CO_2$ tissue culture incubator. Protein samples were assayed in triplicate wells. After 60-72 h, 20 µl of an MTS/PMS mixture (CellTiter 96 AQueous One Solution, Promega Corporation, Madison, Wis.) was added to each well and the plates incubate at 37° C. in the tissue culture incubator for 1-4 h. Absorbance of the wells was read at 490 nm using a microplate reader. Control wells contained media but no cells. Mean absorbance values for the triplicate control wells were subtracted from mean values obtained for the test wells. $EC_{50}$s, the amount of protein required for half maximal stimulation, was calculated for each sample and used to compare bioactivities of the proteins. Non-glycosylated molecular weights were used in the molar ratio calculations for consistency. Non-glycosylated molecular weights of 18,936, 18,987 and 22,129 were assumed for EPO, G-CSF and GH, respectively. Monomer molecular weights were used in the calculations for the IgG fusion proteins. Using molecular weights of the monomer fusion proteins estimated from SDS gels (50-70 kDa) and glycosylated molecular weights of 35 kDa for EPO and 19.7 kDa for G-CSF (GH is not glycosylated) gave similar activity ratios.

B. Bioactivities of EPO-IgG Fusion Proteins

The human UT7/epo cell line was obtained from Dr. F. Bunn of Harvard Medical School, Boston, Mass. This cell line proliferates in response to EPO and is dependent upon EPO for cell survival (Boissel et al., 1993). The cells were maintained in Iscove's Modified Delbecco's Media (IMDM) supplemented with 10% FBS, 50 units/ml penicillin, 50 μg/ml streptomycin and 1 unit/ml recombinant human EPO (CHO cell-expressed; R&D Systems). Bioassays were performed in cell maintenance media using the procedures described above. Serial dilutions of recombinant CHO cell-expressed human rEPO(R&D Systems) were analyzed in parallel.

The UT7/epo cell line shows a strong proliferative response to rEPO, as evidenced by a dose-dependent increase in cell number and absorbance values. In the absence of rEPO, the majority of UT7/epo cells die, giving absorbance values less than 0.1. Commercial CHO cell-expressed rEPO had a mean $EC_{50}$ of approximately 0.6 ng/ml in the bioassay (Table 2). This value agrees with $EC_{50}$ values reported in the R&D Systems specifications (0.05-0.1 unit/ml or approximately 0.4-0.8 ng/ml). The EPO-IgG1-Fc and IgG4-Fc fusion proteins had identical $EC_{50}$'s of approximately 1.3 ng/ml in the bioassay (Table 2). On a molar basis, the $EC_{50}$s of CHO-cell expressed rEPO and the EPO-IgG-Fc fusions were indistinguishable (approximately 30 pM; Table 2). The EPO-IgG1-$C_H$ fusion protein had an $EC_{50}$ of 3.1 ng/ml or 60 pM (Table 2), which represents an approximate 2-fold reduction in specific activity relative to the EPO-IgG-Fc fusion proteins and non-fused rEPO. The EPO-IgG4-$C_H$ fusion protein had a mean $EC_{50}$ of 2.05 ng/ml.

TABLE 2

Bioactivities of EPO-IgG Fusion Proteins

| Clone | Protein | $EC_{50}$ Range (ng/ml)[1] | Mean $EC_{50}$ ng/ml | pM |
|---|---|---|---|---|
| — | RhEPO (CHO) | 0.52, 0.55, 0.60 | 0.56 | 30 |
| pBBT180 | EPO-IgG1-Fc | 1.1, 1.2, 1.5 | 1.27 | 28 |
| pBBT181 | EPO-IgG4-Fc | 1.1, 1.2, 1.5 | 1.27 | 29 |
| pBBT179 | EPO-IgG1-$C_H$ | 2.9, 3.0, 3.5 | 3.13 | 57 |
| pBBT185 | EPO-IgG4-$C_H$ | 2.0, 2.1 | 2.05 | 37 |

[1]Data from individual experiments

C. Bioactivities of G-CSF-IgG Fusion Proteins

The murine NFS60 cell line was obtained from Dr. J. Ihle of the University of Tennessee Medical School, Memphis Term. This cell line proliferates in response to human or mouse G-CSF or IL-3 (Weinstein et al., 1986). The cells were maintained in RPMI 1640 media supplemented with 10% FBS, 50 units/ml penicillin, 50 μg/ml streptomycin and 17-170 units/ml mouse IL-3 (R&D Systems). Assays were performed in RPMI 1640 media supplemented with 10% FBS, 50 units/ml penicillin and 50 μg/ml streptomycin using the procedures described above. Serial dilutions of recombinant human G-CSF (*E. coli*-expressed; R&D Systems) were analyzed in parallel.

The NFS60 cell line shows a strong proliferative response to rhG-CSF, as evidenced by a dose-dependent increase in cell number and absorbance values. rhG-CSF had a mean $EC_{50}$ of 18 pg/ml in the bioassay (Table 3). This value agrees with the $EC_{50}$ value reported in the R&D Systems specifications (10-30 pg/ml). The G-CSF-IgG1-Fc and G-CSF-IgG4-Fc fusion proteins had mean $EC_{50}$'s of 38 and 57 pg/ml, respectively, in the bioassay (Table 3). On a molar basis, the $EC_{50}$s of rhG-CSF and the G-CSF-IgG1-Fc fusions were similar (approximately 0.9 pM; Table 3), whereas the $EC_{50}$ of the G-CSF-IgG4-Fc fusion protein was reduced slightly (1.25 pM). The G-CSF-IgG1-$C_H$ fusion protein had a mean $EC_{50}$ of 182 pg/ml or 3.2 pM (Table 3), which represents an approximate 3-fold reduction in specific activity relative to G-CSF-IgG1-Fc fusion protein and non-fused rhG-CSF. The G-CSF-IgG4-$C_H$ fusion protein had a mean $EC_S$ of 182 pg/ml or 3.9 pM (Table 3)

TABLE 3

| Bioactivities of G-CSF-IgG Fusion Proteins Clone | Protein | $EC_{50}$ Range (pg/ml)[1] | Mean $EC_{50}$ pg/ml | pM |
|---|---|---|---|---|
| — | rhG-CSF | 17, 18, 18 | 17.7 | 0.93 |
| PBBT174 | G-CSF-IgG1-Fc | 34, 39, 42 | 38.3 | 0.84 |
| PBBT175 | G-CSF-IgG4-Fc | 50, 59, 61 | 56.7 | 1.25 |
| PBBT173 | G-CSF-IgG1-$C_H$ | 160, 190, 195 | 182 | 3.2 |
| PBBT184 | G-CSF-IgG4-$C_H$ | 200, 230 | 215 | 3.9 |

[1]Data from individual experiments

D. Bioactivities of GH-IgG Fusion Proteins:

The GH-R4 cell line is described in PCT/US98/14497 and PCT/US00/00931. This cell line is a derivative of the murine FDC-P1 cell line that is stably transformed with the rabbit GH receptor. This cell line proliferates in response to hGH. The cell line is maintained in RPMI 1640 media containing 10% horse serum, 50 units/ml penicillin, 50 μg/ml streptomycin, 2 mM glutamine, 400 μg/ml G418 and 2-5 nM pituitary hGH. GH-IgG fusion protein samples were assayed as described in PCT/US98/14497 and PCT/US00/00931, incorporated herein by reference, using RPMI media supplemented with 10% horse serum, 50 units/ml penicillin, 50 μg/ml streptomycin and 400 μg/ml G418. All assays included a human pituitary GH standard. Pituitary GH stimulates proliferation of GH-R4 c Hs, with an $EC_{50}$ of 0.75-0.85 ng/ml (0.03-0.04 nM), similar to what has been reported in the literature (Rowlinson et al., 1995).

All of the GH-IgG fusion proteins tested stimulated proliferation of GH-R4 cells (Table 4). The GH-IgG1-Fc fusion protein was the most active, possessing an $EC_{50}$ of 7-8 ng/ml (~0.16 nM). The GH-IgG4-Fc fusion protein was about twofold less active than the IgG1 fusion protein, with a mean $EC_{50}$ of 17 ng/ml (0.35 nM). The GH-IgG1-$C_H$ fusion protein had the lowest activity, with an $EC_{50}$ of 35 ng/ml (0.6 nM). On a molar basis, bioactivities of the fusion proteins were reduced 4-fold (GH-IgG1-Fc), 10-fold (GH-IgG4-Fc) and 17-fold (GH-IgG1-$C_H$) relative to pituitary hGH.

TABLE 4

| Bioactivities of GH-IgG Fusion Proteins Clone | Protein | $EC_{50}$ Range (ng/ml)[1] | Mean $EC_{50}$ ng/ml | nM |
|---|---|---|---|---|
| — | Pituitary hGH | 0.75, 0.75, 0.85, 0.85 | 0.8 | 0.036 |

TABLE 4-continued

Bioactivities of GH-IgG Fusion Proteins

| Clone | Protein | EC$_{50}$ Range (ng/ml)[1] | Mean EC$_{50}$ ng/ml | nM |
|---|---|---|---|---|
| PBBT172 | GH-IgG1-Fc | 6.5, 7.0, 7.8, 9 | 7.6 | 0.160 |
| PBBT163 | GH-IgG4-Fc | 15, 16, 18, 18 | 17 | 0.350 |
| PBBT171 | GH-IgG1-C$_H$ | 28, 32, 40, 40 | 35 | 0.600 |

[1]Data from individual experiments

Example 4

Eliminate or Minimize the Linker in the GF-IgG Fusion Proteins

GF-IgG fusion proteins in which the 7 amino acid linker [ser-gly-gly-ser-gly-gly-ser] (SEQ ID NO:3) that fuses the GF to the IgG domain is eliminated (direct fusions) or reduced to 2 to 4 amino acids can be constructed as described below. Similar methods can be used to create linkers shorter than 7 amino acids, to create linkers longer than 7 amino acids and to create linkers containing other amino acid sequences. The experiments described below use IgG1-Fc and EPO and G-CSF as examples, however, similar procedures can be used for other GF or IgG domains, and domains for other IgG subtypes and domains from IgM, IgA, IgD and IgE antibodies. The modified fusion proteins can be expressed, purified and their specific activities determined in in vitro bioassays as described in the Examples.

1. Direct Fusions: GF-IgG fusions without a linker can be created using PCR based "gene splicing by overlap extension" as described in Example 1 (Horton et al., 1993). One can generate PCR products consisting of the IgG1-Fc coding sequence with a short 5' extension, consisting of the 3' terminal ~15 by of coding sequence of EPO or G-CSF fused directly to the hinge coding sequence. At the same time one can generate PCR products consisting of the EPO or G-CSF coding sequences with a short 3' extension consisting of the first 15 by of the hinge coding sequence fused directly to the EPO or G-CSF coding sequence. The growth factor fragments and the IgG1-Fc fragments can then be spliced together via PCR "Sewing" (Horton et al., 1993) to generate direct fusions. These PCR products can be digested with appropriate restriction enzymes to generate relatively small DNA segments that span the fusion point and which can be readily cloned into similarly cut vectors pGDN3.1(+)::EPO-IgG1-Fc and pcDNA3.1(+)::G-CSF-IgG1-Fc for sequence confirmation and COS cell expression. Cloning these smaller DNA fragments will minimize the sequencing that will need to be done to confirm the sequences of the direct fusions.

1. A. EPO-IgG Direct Fusions

An EPO-IgG1-Fc direct fusion was created by PCR using plasmid pBBT180 as the DNA template. One PCR reaction used oligos BB198 (5'-AGGACAGGGGACAGAGAGC-CAAA TCTIGTGACAAA-3') (SEQ.ID.NO.22) and BB82. The second PCR reaction used oligos BB199 (5'ACAAGATTTGGGCTCTCTGTCCCCTGTC-CTGCAGGC-3') (SEQ.ID.NO.23) and BB89. The products from these PCR reactions were gel-purified, mixed and subjected to a third PCR reaction using oligos BB82 and BB89. The approximate 1300 by PCR product was gel-purified, digested with and Bsr GI and Sac II, and cloned into similarly cut pBBT180 that had been treated with calf intestinal phosphatase. A clone with the correct insert was identified by DNA sequencing and named pBBT356.

An EPO-IgG4-Fc direct fusion was created by PCR using plasmid pBBT181 as the DNA template. One PCR reaction used oligos BB200 (5'-AGGACAGGGGACAGAGAGTC-CAAATAT GGTCCCCCA-3') (SEQ.ID.NO.24) and BB82. The second PCR reaction used oligos BB201 (5'-AC-CATATTTGGACTCTCTGTCCCCTGTCCTGCAGGC-3') (SEQ.ID.NO.25) and BB89. The products from these PCR reactions were gel-purified, mixed and subjected to a third PCR reaction using oligos BB82 and BB89. The approximate 1300 by PCR product was gel-purified, digested with and Bsr GI and Sac II, and cloned into similarly cut pBBT181 that had been treated with calf intestinal phosphatase. A clone with the correct insert was identified by DNA sequencing and named pBBT357. A clone with a correct EPO sequence, but a mutation in the IgG4-Fc region (Phe-25 changed to Ser) was named pBBT 273.

COS cells were transfected with pBBT273 and the EPO-IgG4-Fc fusion protein purified as described in Example 2. The purified protein, which consisted primarily of a disulfide-linked dimer (>90%), stimulated proliferation of UT7/epo cells with an EC$_{50}$ of 2 ng/ml. The bioassay was performed as described in Example 3.

An EPO (des-Arg-166)-IgG1-Fc direct fusion can be created as described above for the EPO-IgG1-Fc direct fusion except that oligonucleotide EPODFE (5'-TGCAGGA-CAGGGGACGAGCCCAAAT CTTGTGACAAA-3') (SEQ.ID.NO.26) can be substituted for BB198 and EPODFF (5'-ACAAGATTIGGGCTCGTCCCCTGTCCTG-CAGGCCTC-3') (SEQ.ID.NO.27) can be substituted for BB199. Similarly, EPO(des-Arg-166)-IgG4-Fc direct fusions can be constructed as described above for EPO-IgG4-Fc fusions except that EPODFG (5'-TGCAGGACAGGG-GACGAGTCCAAATAT GGTCCCCCA-3') (SEQ.ID.NO.28) can be substituted for BB200 and EPODFH (5'-ACCATATTTGGACTCGTCCCCTGTCCTG-CAGGCCTC-3') (SEQ.ID.NO.29) can be substituted for BB201.

1. B. G-CSF Direct Fusions

A G-CSF-IgG1-Fc direct fusion was created by PCR using plasmid pBBT174 as the DNA template. One PCR reaction used oligos BB202 (5'-CACCITGCCCAGCCCGAGC-CCAAA TCTFGTGACAAA-3') (SEQ.ID.NO.30) and BB82. The second PCR reaction used oligos BB203 (5'-ACAAGATTTGGGCTCGGGCTGGGCAAG GTGGCG-TAG-3') (SEQ.ID.NO.31) and BB91. The products from these PCR reactions were gel-purified, mixed and subjected to a third PCR reaction using oligos BB82 and BB91. The approximate 1300 by PCR product was gel-purified, digested with PflMI and Sac II, and the ~400 by PflMI/Sac II fragment gel-purified. This fragment was cloned into similarly cut pBBT174 that had been treated with calf intestinal phosphatase. A clone with the correct insert was identified by DNA sequencing and named pBBT299.

A G-CSF-IgG4-Fc direct fusion was created by PCR using plasmid pBBT175 as the DNA template. One PCR reaction used oligos BB204 (5'-CACCTTGCCCAGCCCGAGTC-CAAATATGGT CCCCCA-3') (SEQ.ID.NO.32) and BB82. The second PCR reaction used oligos BB205 (5'-AC-CATATTTGGACTCGGGCTGGGCAAG GTGGCGTAG-3') (SEQ.ID.NO.33) and BB91. The products from these PCR reactions were gel-purified, mixed and subjected to a third PCR reaction using oligos BB82 and BB91. The approximate 1300 by PCR product was gel-purified, digested with and PflMI and Sac II, and the ~400 by PflMI/Sac II fragment gel-purified. This fragment was cloned into similarly cut pBBT175 that had been treated with calf intestinal phosphatase. A clone with the correct insert was identified by DNA sequencing and named pBBT300.

COS cells were transfected with pBBT299 and pBBT300 and the G-CSF-IgG1-Fc and G-CSF-IgG4-Fc direct fusion proteins purified as described in Example 2. The purified proteins, which consisted primarily (>90%) of disulfide-linked dimers, stimulated proliferation of NFS60 cells with an $EC_{50}$ of 50-60 pg/ml (G-CSF-IgG1-Fc direct fusion) and 43-50 pg/ml (G-CSF-IgG4-Fc direct fusion). The bioassay was performed as described in Example 3.

2. GF-IgG Fusion Proteins Containing Two or Four Amino Acid Linkers

To construct a di-peptide [ser-gly] linker, one can PCR the IgG1-Fc sequence with a 5' oligonucleotide that adds the 5' extension CGCTCCGGA to the hinge coding sequence. The TCCGGA hexanucleotide is a cleavage site for the restriction endonuclease Bsp EI and encodes amino acids ser-gly. This PCR fragment can be digested with Bsp EI and Sac II and the ~240 by fragment cloned into similarly cut pCDN3.1(+)::EPO-IgG1-Fc and pcDNA3.1(+)::G-CSF-IgG1-Fc. The unique Bsp EI site in each of these plasmids occurs at the first ser-gly in the linker [ser-gly-gly-ser-gly-gly-ser] (SEQ ID NO:3) so that the resulting recombinants will contain this 2 amino acid, ser-gly, linker. The sequence of the newly inserted ~250 by Bsp EI-Sac II fragment can be verified.

A similar procedure can be used to construct the 4 amino acid [ser-gly-gly-ser] (SEQ ID NO:1) linker. One can PCR the IgG1-Fc sequence with a 5' oligonucleotide that adds the 5' extension CGCGGATCC to the hinge coding sequence. The GGATCC hexanucleotide is a cleavage site for the restriction endonuclease Bam HI and encodes amino acids gly-ser. This PCR fragment can be digested with Bam HI and Sac H and the ~240 by fragment cloned into similarly cut pCDN3.1(+)::EPO-IgG1-Fc and pcDNA3.1(+)::G-CSF-IgG1-Fc. The unique Bam HI site in each of these plasmids occurs at the first gly-ser in the linker [ser-gly-gly-ser-gly-gly-ser] (SEQ ID NO:3) so the recombinants will contain the 4 amino acid (ser-gly-gly-ser) (SEQ ID NO:1) linker. The sequence of the inserted ~250 by Bam HI-Sac II piece can be verified.

An IgG1-Fc domain that can be used to construct fusion proteins containing a two amino acid SerGly linker between the growth factor/cytokine domain and the IgG1-Fc domain was created by PCR. The PCR reaction used primers BB 194 (5'-CGCGAATTCCGGAGAGCCCAAATCTT GTGACAAA3') (SEQ.ID.NO.34) and BB 82. The DNA template was pBBT195. The PCR products were put through a PCR clean-up kit (Qiagen, Inc.) and digested with EcoRI and SacII. The restriction digest was put through a PCR clean-up kit and cloned into similarly cut pBC SK(+) (Stratagene, Inc.) DNA that had been treated with calf intestinal phosphatase. The ligations were used to transform E. coli JM 109. Transformants were selected on LB agar plates containing 50 µg/ml chloramphenicol. A clone with the correct sequence was identified by DNA sequencing and named pBBT242.

An IgG1-Fc domain that can be used to construct fusion proteins containing the four amino acid linker, Ser-Gly-Gly-Ser (SEQ.ID.NO.1), between the growth factor/cytokine domain and the IgG1-Fc domain was created by PCR. The PCR reaction used primers BB 195 (5'-CGCGGATCC GAGCCCAAATCTTGTGACAAA-3') (SEQ.ID.NO.35) and BB 82. The DNA template was pBBT195. The PCR products were put through a PCR clean-up kit (Qiagen, Inc.) and digested with BamHI and Sac II. The restriction digest was put through a PCR clean-up kit and cloned into similarly cut pBC SK(+) DNA that had been treated with calf intestinal phosphatase. The ligations were used to transform E. coli JM109. Transformants were selected on LB agar plates containing 50 µg/ml chloramphenicol. A clone with the correct sequence was identified by DNA sequencing and named pBBT243.

An IgG4-Fc domain that can be used to construct fusion proteins containing the two amino acid linker, SerGly, between the growth factor/cytokine domain and the IgG4-Fc domain was created by PCR. The PCR reaction used primers BB 196 (5'-CGCGAATTCCGGAGAGTCCAAATATGG TCCCCCA-3') (SEQ.ID.NO.36) and BB 82. The DNA template was pBBT196. The PCR products were put through a PCR clean-up kit (Qiagen, Inc.) and digested with EcoRI and SacII. The restriction digest was put through a PCR clean-up kit and cloned into similarly cut pBC(SK+) DNA that had been treated with calf intestinal phosphatase. The ligations were used to transform E. coli JM109. Transformants were selected on LB agar plates containing 50 µg/ml chloramphenicol. A clone with the correct sequence was identified by DNA sequencing and named pBBT244.

An IgG4-Fc domain that can be used to construct fusion proteins containing the four amino acid linker, ser-gly-gly-ser, between the growth factor/cytokine domain and the IgG4-Fc domain was created by PCR. The PCR reaction used primers BB 197 ((5'-CGCGGATCCGAGTCCAAATATGGT CCCCCA-3') (SEQ.ID.NO.37) and BB 82. The DNA template was pBBT196. The PCR products were put through a PCR clean-up kit (Qiagen, Inc.) and digested with BamHI and Sac II. The restriction digest was put through a PCR clean-up kit and cloned into similarly cut pBC (SK+) DNA that had been treated with calf intestinal phosphatase. The ligations were used to transform E. coli JM109. Transformants were selected on LB agar plates containing 50 µg/ml chloramphenicol. A clone with the correct sequence was identified by DNA sequencing and named pBBT245.

The modified IgG domains described above were used to construct EPO-IgG and G-CSF-IgG fusion proteins containing four amino acid linkers. Plasmids pBBT174 and pBBT180 were digested with BamHI and SacII and treated with calf intestinal phosphatase. The ~6 kb vector bands were gel-purified and ligated with the ~800 by IgG insert from pBBT243, which had been gel-purified following digestion of pBBT243 DNA with BamHI and SacII. Similarly, plasmids pBBT175 and pBBT181 were digested with BamHI and Sad and treated with calf intestinal phosphatase. The ~6 kb vector bands were gel-purified and ligated with the ~800 by IgG insert from pBBT245, which had been gel-purified following digestion of pBBT245 DNA with BamHI and SacII. The ligations were used to transform E. coli DH5α and transformants selected on LB agar plates containing 100 µg/ml ampicillin. Clones containing the correct sequences were identified by restriction mapping and DNA sequencing. The EPO-IgG1-Fc and EPO-IgG4-Fc fusions containing the 4 amino acid linker were named pBBT279 and pBBT280, respectively. The G-CSF-IgG1-Fc and G-CSF-IgG4-Fc fusions containing the 4 amino acid linker were named pBBT277 and pBBT278, respectively.

The modified IgG domains described above can be used to construct EPO-IgG and G-CSF-IgG fusion proteins containing two amino acid linkers. Plasmids pBBT174 and pBBT180 can be digested with BspEI and SacII and treated with calf intestinal phosphatase. The ~6 kb vector bands can be gel-purified and ligated with the ~800 by IgG insert from pBBT242, which had been gel-purified following digestion of pBBT242 DNA with BspEI and Sac II. Similarly, plasmids pBBT175 and pBBT181 can be digested with BspEI and Sac II and treated with calf intestinal phosphatase. The ~6 kb vector bands can be gel-purified and ligated with the ~800 by IgG insert from pBBT244, which has been gel-purified following digestion of pBBT244 DNA with Bsp EI and Sac II. The ligations can be used to transform *E. coli* DH5α and transformants selected on LB agar plates containing 100 µg/ml ampicillin.

The recombinant fusion proteins can be used to transfect COS cells and be purified as described in Example 2. In vitro and in vivo bioactivities of these fusion proteins can be determined as described in the Examples 3 and 8.

Example 5

Methods to Improve Bioactivities of IgG-$C_H$ Fusion Proteins

All of the IgG-$C_H$ fusion proteins appeared to aggregate during purification and the specific activities of the fused growth factors were reduced ~2-3-fold as compared to the analogous IgG-Fc fusions. Aggregation may be due to hydrophobic interactions involving the CH1 domain that normally interfaces with the light chain. Coexpression of Ig light chains with the GF-IgG-$C_H$ fusions can prevent aggregation. We describe three ways to compress Ig light chains and Ig heavy chains below. The experiments described below use IgG-Fc, IgG-$C_H$, EPO and G-CSF as examples, however, similar procedures can be used for other GF or IgG domains, and domains for other IgG subtypes and domains from IgM, IgA, IgD and IgE antibodies. The DNA sequences of human kappa and lambda light chains are known (Reiter et al., 1980). cDNA sequences encoding the human kappa and/or lambda light chain constant (CL) regions can be obtained by PCR amplification from the human leukocyte single-stranded cDNA (Clontech) or human genomic DNA (Clontech). The DNA sequences of the cloned CL domains can be confirmed prior to use in the experiments described below. The modified fusion proteins can be expressed, purified and their specific activities determined in in vitro bioassays as described in Examples 2 and 3.

1. Co-expression of the light chain constant region. A Kozak sequence (Kozak, 1991) and a secretion signal can be added to the 5' end of the light chain constant region to enhance translational initiation and direct the secretion of the light chain constant region. A translational stop codon can be added to the 3' end of the sequence. Appropriate cloning sites can be added to the 5' and 3' ends to allow cloning into the mammalian cell expression vector pREP4 (Invitrogen) under control of the RSV promoter and preceding the SV40 derived polyA addition site. This construct can be used to cotransfect COS cells along with pcDNA3.1(+) derivatives that express, for example, EPO-IgG-$C_H$ and G-CSF-IgG-$C_H$. Alternatively, both light and heavy chains can be expressed from a single plasmid construct. In this case, the light chain sequence and the flanking promoter and polyA sites from pREP4 can be excised with appropriate restriction enzymes and cloned into pcDNA3.1(+). The EPO-IgG-$C_H$ and G-CSF-IgG-$C_H$ coding sequences could then cloned into the pcDNA3.1(+) polylinker under control of the CMV promoter.

DNA encoding the constant region of the human Kappa light chain (IgKC) was amplified from human genomic DNA as described below in Section 2 of this Example. This sequence was modified by PCR to create a construct suitable for expression of the light chain constant region. A Kozak sequence (Kozak, 1991) and the human Growth Hormone secretion signal were added to the 5' end of the light chain constant region. These modifications were made via two sequential PCR reactions. In the first the cloned and sequenced pcDNA3.1(+)::fusIgKC DNA was used as template. The primers were BB169 (5>GCTTTTGGCCTGCTC-MCCMCCC TGGCTTCAAGAGGGCAGTGCCACTGIG-GCTGCACCATCT>3) (SEQ.ID.NO.38) and BB150 BB150 (5>CGCTCTAGACTA ACACTCTCCCCTGTTGAA>3) (SEQ.ID.NO.39). Forward primer BB169 anneals to the 5' end of the light chain constant region and adds sequence encoding 15 amino acids of the hGH leader sequence. Reverse primer BB150 anneals to the 3' end of the coding sequence for the constant region of the human Kappa light chain and includes a translational stop codon followed by an Xba I site. The product of this PCR reaction was gel-purified and used as template in a second PCR reaction with primers BB168 (5>CGCAAGCTTGCCACCATGGCTACAGGC TCCCGGACGTCCCTGCTCCTGGTTTTG-GCCTGCTCTGC>3)(SEQ.ID.NO.40) and BB150. Forward primer BB168 adds the remainder of the hGH leader sequence as well as a Kozak sequence and contains a Hin dIII site for cloning purposes. Reverse primer BB150 is described above. The product of this PCR reach n was digested with Hin dIII and Xba I and cloned into vector pcDNA3.1(+) that had been digested with Hin dIII and Xba I and treated with alkaline phosphatase. The DNA sequence was verified for one such clone.

2. Co-expression of GF-light chain constant region fusion proteins. An alternative mode of light chain expression would be to modify the 5' end to add a portion of a flexible peptide linker sequence fused to the amino-terminus of the CL coding sequence and add a translational stop codon to the 3' end of the sequence. Appropriate cloning sites can be added as well to the 5' and 3' ends to allow cloning as an in frame fusion to the EPO and G-CSF genes cloned in the plasmids pcDNA3.1 (+)::EPOfus and pcDNA3.1(+)::G-CSFfus. This plasmid can be cotransfected into COS cells with plasmids that express, for example, EPO-IgG1-$C_H$ and G-CSF-IgG1-$C_H$. In this instance both heavy and light chains will contain growth factor fusions. The light and heavy chains also could be expressed from a single pcDNA3.1 (+) construct as described above. EPO and G-CSF also can be expressed as direct fusions with Ig-$C_L$ using procedures similar to those described elsewhere in the Examples.

DNA encoding the constant region of the human Kappa light chain (IgKC) was amplified from human genomic DNA (CLONTECH, Inc., Palo alto, CA) by PCR using primers BB149 (5>CGCGGATCCGGTGGCTCAACTGTGGCTG-CACCATCTGT>3)(SEQ.ID.NO.41) and BB150 (5>CGCTCTAGACTA ACACTCTCCCCTGTTGAA>3) (SEQ.ID.NO.42). Forward primer BB149 anneals to the 5' end of the coding sequence for the constant region of the human Kappa light chain and includes a portion of the peptide linker (gly-ser-gly-gly-ser) (SEQ.ID.NO.2) containing a Bam HI site at the 5' end. Reverse primer BB150 anneals to the 3' end of the coding sequence for the constant region of the human Kappa light chain and includes a translational stop codon followed by an Xba I site. The resulting ~330 by PCR product was digested with Bam HI and Xba I, gel purified and cloned into vector pcDNA3.1 (+) that had been digested with Bam HI and Xba I, alkaline phosphatase treated, and gel purified. One clone was sequenced and found to match the published human IgKC genomic DNA sequence (Hieter et al., 1980). The ~330 Bam HI-Xba I fragment was subsequently excised from this plasmid, termed pcDNA3.1(+):: fusIgKC, and cloned into pBBT190, pBBT191, and PBBT192 (described in Example 10 below) resulting in fusion of the IgKC domain to IFN-α, IFN-β, and IFN-γ respectively. Similar procedures can be used to construct other growth factor/cytokine-IgKC fusion proteins.

3. Light chain-heavy chain fusions. A third mode of "co-expression" would be to modify the 5' and 3' ends of the CL coding sequence to incorporate portions of a flexible peptide linker at both ends. By also incorporating appropriate cloning sites (e.g. Bsp EI and Bam HI) such a construct can be inserted into the Bsp EI and Bam HI sites within the flexible peptide linkers of the EPO-IgG-$C_H$ and G-CSF-IgG-$C_H$ fusions in pcDNA3.1 (+). The resulting constructs would encode, for example, single polypeptide [EPO]-[CL]-[IgG-$C_H$] and [G-CSF]-[CL]-[IgG-$C_H$] fusions. The fusion of the carboxy-terminus of the light chain constant region to the amino-terminus of the heavy chain CH1 domain would be analogous to single chain Fv polypeptides. Flexible peptide linkers of the (ser-gly-gly) motif on the order 14 to 20 residues in length have been used to fuse the carboxy-terminus of the light chain variable region to the amino-terminus of the heavy chain variable domain (Stewart at al., 1995) and could be used to join the CL domain to the IgG-$C_H$ domain.

Example 6

GF-IgG Fusion Proteins with Reduced Complement Binding and Fc Receptor Binding Properties Certain GF-IgG1 fusion proteins may be toxic or lack efficacy in the animal models due to activation of complement or immune processes related to Fc receptor binding. For this reason, GF-IgG4 fusion proteins may be preferred because IgG4 is less efficient at complement activation and Fc receptor binding than is IgG1 (Roit et al., 1989). The EPO- and G-CSF-IgG4-Fc fusion proteins are as potent or nearly as potent as the IgG1-Fc fusion proteins in in vitro bioassays. Alternatively, one can perform in vitro mutagenesis experiments, as detailed below, to change specific amino acids in the IgG domains known to be responsible for complement activation and Fc receptor binding. The modified fusion proteins can be expressed, purified and their specific activities determined in in vitro bioassays as described in Examples 2 and 3.

A. Complement Binding. Amino acids in IgGs that play a role in complement activation have been localized to the IgG CH2 domain. Specifically, amino acids Glu318, Lys320, Lys322, Ala330 and Pro331 in human IgG1 have been implicated as contributing to complement activation (Isaacs et al., 1998). Substitution of Glu318, Lys320 and Lys322 in IgG1 with alanine residues results in IgG proteins possessing reduced ability to activate complement (Isaacs et al., 1998). The amino acid sequence of IgG4 is identical to IgG1 in this region, yet IgG4 does not activate complement. As an alternative to using IgG4, one can change Glu318, Lys320 and Lys 322 (alone or in combination) of IgGs that have these residues to alanine residues or other amino acids that reduce complement activation using the PCR-based mutagenesis strategies described in Example 1.

B. Fc Receptor Binding. Human IgG subclasses differ in their ability to bind Fc receptors and stimulate antibody-dependent cell-mediated cytotoxicity (ADCC). IgG1, IgG3 and IgG4 are best at stimulating ADCC, whereas IgG2 has significantly reduced ability to stimulate ADCC (Roit et al., 1989). ADCC occurs through a mechanism that involves binding of the antibody to Fc receptors on immune cells. Amino acids responsible for Fc receptor have been localized to the CH2 domain of the IgG molecule. Specifically, amino acids 233-235 have been implicated in Fc receptor binding. Human IgG1 has the amino acid sequence GluLeuLeu in this region, whereas IgG2, which does not bind Fc receptors, has the sequence ProAlaVal. IgG4 has the sequence GluPheLeu in this region and is 10-fold less efficient at binding Fc receptors than IgG1. Substitution of the IgG2 sequence ProAlaVal for GluLeuLeu at positions 233-235 in IgG1 for IgG4 results in IgG1 and IgG4 antibodies with significantly reduced capacity for Fc receptor binding and ADCC (Isaacs et al., 1998). One can introduce some or all of these amino acid changes into the GF-IgG fusion protein constructs using the PCR-based mutagenesis strategy described in Example 1. Alternatively one can construct modified GF-IgG fusion proteins in which glycosylation of asparagine 297 in the IgG1 CH2 domain (or the equivalent asparagine residue in the other IgG subclasses) is prevented. Aglycosylated IgG1 antibodies display significantly reduced binding to Fc receptors and ability to lyse target cells as compared to glycosylated IgG1 antibodies (Isaacs et al., 1998). One can construct aglycosylated versions of the GF-IgG fusion proteins by changing asparagine-297 to glutamine or another amino acid, or by changing threonine-299, which is part of the glycosylation recognition sequence (Asparagine-X-Serine/Threonine), to alanine or to an amino acid other than serine. The amino acid in the X position of the glycosylation recognition sequence, i.e, amino acid 298, also could be changed to proline to prevent glycosylation of asparagine 297 in the IgG CH2 domain.

Example 7

Pharmacokinetic Experiments with GF-IgG Fusion Proteins

Pharmacokinetic experiments can be performed to demonstrate that the GF-IgG fusion proteins have longer circulating half-lives than the corresponding non-fused proteins. Both intravenous and subcutaneous pharmacokinetic data can be obtained. Terminal pharmacokinetic parameters can be calculated from the intravenous delivery data.

For the intravenous delivery studies, rats (~350 g) can receive an intravenous bolus injection (0.1 mg/kg) of the IgG1-Fc fusion protein (EPO or G-CSF) or the corresponding non-fused protein (EPO or G-CSF) and circulating levels of the proteins measured over the course of 144 h. Three rats can be used for each protein sample. Blood samples can be drawn at 0, 0.08, 0.5, 1.5, 4, 8, 12, 24, 48, 72, 96, 120, and 144 h following intravenous administration. Serum levels of the test proteins can be quantitated using commercially available EPO and G-CSF ELISA kits (R & D Systems). Serial dilutions of each blood sample can be analyzed initially in the in vitro bioassays to identify dilutions that will fall within the linear range of the ELISAs. (0.025 to 1.6 ng/ml for EPO and 0.04 to 2.5 ng/ml for G-CSF). Titration experiments can be performed to determine the relative sensitivities of the ELISAs for detecting the IgG1-Fc fusion proteins and the corresponding non-fused proteins. The subcutaneous delivery studies can follow the same protocol as the intravenous studies except for the route of delivery. Serum levels of the test proteins can be quantitated by ELISA as described above.

Example 8

Animal Efficacy Models

In vivo efficacy of the EPO-IgG1-Fc and G-CSF-IgG1-Fc fusion proteins can be demonstrated in normal rats and mice.

These studies can use a variety of doses and dosing schedules to identify the proper doses and dosing schedules. Efficacy of the EPO-IgG and G-CSF-IgG fusion proteins also can be demonstrated in appropriate disease models—anemia for EPO-IgG1-Fc and neutropenia for G-CSF-IgG1-Fc. The pharmacokinetic experiments will provide guidance in deciding dosing schedules for the IgG1 fusion proteins to be used for the animal studies. From published results with other IgG-Fc fusion proteins (Richter et al., 1999; Zeng et al., 1995) the EPO-IgG and G-CSF-IgG fusion proteins can be effective when administered every other day or every third day and possibly less often, e.g. a single injection. The dosing schedules may have to be modified depending upon the results of the pharmacokinetic studies and initial animal efficacy results. The dose of protein administered per injection to the rodents also may have to be modified based upon the results of the pharmacokinetic experiments and initial animal efficacy results A. EPO Animal Efficacy Models—Normal Rats 1. Single Injection:

Groups of three male Sprague Dawley rats, weighing ~320 g each, received a single intravenous injection (lateral tail vein) of wild type recombinant EPO containing the amino acid sequence ser-gly-gly-ser-gly-gly-ser-asp-tyr-lys-asp-asp-asp-asp-lys (SEQ.ID.NO.43) at its carboxy end (rEPO-FLAG), or EPO-IgG1-Fc at a dose of 100 µg/kg. The rEPO-FLAG was expressed by transfection of COS-1 cells and purified by affinity chromatography using an anti-FLAG monoclonal antibody. Protein concentrations of rEPO-FLAG and EPO-IgG1-Fc were determined using a Bradford dye binding assay and bovine serum albumin as the standard. At selected time points blood samples (0.3 to 0.4 ml) were drawn from the rats into EDTA anti-coagulant tubes. Aliquots of the blood samples were analyzed for a complete blood cell (CBC) count. The remainder of the blood sample was centrifuged and the plasma frozen at ~80° C. Blood samples were drawn at 0.25, 2, 4, 10, 24, 48, 72, 96, 120, 144, 168 and 192 h post-injection. A 0 h baseline sample was obtained ~24 h prior to injection of the test compounds. Table 4 shows the mean blood hematocrits (+/−SE) for the different test groups at 0 hour and at 192 h post-injection. The group receiving EPO-IgG1-Fc showed a significant increase in hematocrit levels at 192 h compared to 0 hour ($p<0.05$). The group receiving rEPO-FLAG did not show a significant increase in hematocrit levels between the 0 and 192 hour time points.

TABLE 4

| Group | Hematocrit (%) | |
| --- | --- | --- |
|  | 0 hour | 192 hour |
| rEPO-FLAG | 42.9 +/− 0.82 | 44.4 +/− 1.007 |
| EPO-IgG1-Fc | 44.7 +/− 0.296 | [a]48.0 +/− 0.95 |

[a]$p < 0.05$ versus 0 hour time point.

Similar studies can be performed using lower or higher doses (0.001 to 10 mg/kg) of the proteins. Similar studies also can be performed using the subcutaneous route of administration of the proteins.

2. Daily, Every Other Day or Every Third Day dosing Schedules

Sprague-Dawley rats (~200 g) can be purchased from a commercial supplier such as Charles River (Wilmington, Mass.). Previous studies have shown that administration of 100-1000 IU/kg (approximately 800 ng-8 µg/kg) of rEPO once per day (160 ng-1.6 µg SID/200 g rat) by subcutaneous injection gives a significant increase in hematocrit and erythropoiesis in rodents (Matsumoto et al., 1990; Vaziri et al., 1994; Baldwin et al., 1998; Sytkowski et al., 1998). Groups of 5 rats can receive subcutaneous injections of rEPO, rEPO-FLAG, EPO-IgG1-Fc or placebo (vehicle solution) at specified intervals (daily, every other day or every third day) for five to nine days. A dose equivalent to a molar ratio of EPO (400 ng-4 µg/200 g rat of the EPO-IgG1-Fc fusion protein) can be tested. Higher or lower doses also can be tested. A wide range of EPO-IgG1-Fc doses (over 500-fold variation) can be tested in these initial experiments to increase the likelihood that one of the doses will be effective. It is possible that administration of too much EPO-IgG1-Fc will impede erythropoiesis due to toxicity. Control rats can receive vehicle solution only. Additional control groups can receive daily injections of rEPO (160 ng-1.6 µg/200 g rat for 5-9 days) and 160 ng-1.6 µg rEPO using the same dosing regimen as EPO-IgG1-Fc. One to two days after the final injection the animals can be sacrificed and blood samples collected for hematocrit and complete blood cell count (CBC) analysis. Hematopoietic tissues (liver and spleen) can be collected, weighed and fixed in formalin for histopathologic analyses to look for evidence of increased erythropoiesis. Bone marrow can be removed from various long bones and the sternum for unit particle preps and histopathologic analysis to look for evidence of increased erythropoiesis. Comparisons between groups can be made using a Students T test for single comparisons and one-way analysis of variance for multiple comparisons. $P<0.05$ can be considered significant.

Daily injections of rEPO can stimulate increases in hematocrit and erythropoiesis in the rats, whereas less frequent administration of the same dose of rEPO can not, or do so to a lesser extent. Dose-dependent increases in these parameters can be observed in the EPO-IgG-Fc-treated animals. Greater increases in these parameters may be observed in the EPO-IgG1-Fc-treated animals than in animals treated with EPO using the less frequent dosing schedules. Significantly less EPO-IgG1-Fc may be required to achieve the same increases in these parameters obtained with daily injections of EPO.

Additional experiments with less frequent dosing, e.g., a single injection, could be performed.

B. EPO Efficacy Experiment—Anemic Rat Model

Cisplatin-induced anemia is a well-characterized rodent model of chemotherapy-induced anemia and has direct relevance to the human clinical setting. rEPO reverses the anemia in this model when administered at daily doses of 100-1,000 Units/kg (Matsumoto et al., 1990; Vaziri et al., 1994; Baldwin et al., 1998). EPO-IgG-Fc also will be effective at reversing anemia in this model using once per day, every other day or every third day dosing schedules. The dosing schedule for EPO-IgG-Fc to be used in this experiment could be the one that worked best in the normal rat experiments. Sprague-Dawley rats (~200 g) can be treated on day 0 with an intraperitoneal injection of Cisplatin (3.5 mg/kg) to induce anemia and randomized to various treatment groups. Rats can receive daily, every other day or every third day injections of EPO-IgG-Fc, rEPO or saline for up to 9 days at a dose of 2 µg-20 µg/kg. One control group of rats can receive daily subcutaneous injections of rEPO (100-1,000 Units/kg). Another control group can not receive the initial Cisplatin injection but can receive injections of saline using the same dosing schedule as the other test proteins. On day 9 the rats can be sacrificed and blood and tissue samples obtained for comprehensive CBC and histopathology analyses. Ten to one hundred fold higher or lower doses of the EPO-IgG1-Fc fusion proteins also could be tested.

C G-CSF Animal Efficacy Models

In vivo efficacy of the G-CSF-IgG fusion proteins (C17 or C17S versions) can be measured in normal or neutropenic rodents such as mice or rats by demonstrating that the proteins stimulate increases in circulating neutrophil levels and granulopoiesis compared to vehicle-treated animals. G-CSF stimulates neutrophil levels in normal and neutropenic rodents at a dose of 100 µg/kg (Kubota et al., 1990; Kang et al., 1995). Mice or rats can be used for these experiments. One can extrapolate pharmacokinetic data from the rat to the mouse because protein clearance is proportional to body weight (Mahmood, 1998). One can demonstrate efficacy of G-CSF-IgG1-Fc in normal animals using daily, every other day or every third day dosing schedules. Efficacy also can be demonstrated following a single injection. Effectiveness of G-CSF-IgG1-Fc in a mouse neutropenia model also can be demonstrated using daily, every other day or every third day dosing schedules.

C. 1. Efficacy in Normal Rats Following a Single Injection

Groups of three male Sprague Dawley rats, weighing ~320 g each, received a single intravenous injection (lateral tail vein) of wild type recombinant G-CSF (prepared by Bolder BioTechnology), Neupogen® (a recombinant G-CSF sold by Amgen, Inc.) or G-CSF-IgG1-Fc, each at a dose of 100 µg/kg. Protein concentrations were determined using a Bradford dye binding assay using bovine serum albumin as the standard. At selected time points blood samples (0.3 to 0.4 ml) were drawn from the rats into EDTA anti-coagulant tubes. Aliquots of the blood samples were analyzed for a complete blood cell (CBC) count. The remainder of the blood sample was centrifuged and the plasma frozen at −80° C. Blood samples were drawn at 0.25, 1.5, 4, 8, 12, 16, 24, 48, 72, 96, 120 and 144 h post-injection. A 0 h baseline sample was obtained ~24 h prior to injection of the test compounds. Tables 5, 6 and 7 show the mean blood neutrophil, total white blood cell counts and blood monocyte counts for the different test groups over time. All three test compounds stimulated an increase in peripheral white blood cells and neutrophils over baseline values. White blood cell and neutrophil counts for the test groups receiving wild type recombinant G-CSF and Neupogen® peaked ~24 h post-injection and returned to baseline values by ~48 h. In contrast, white blood cell and neutrophil counts for the rats receiving G-CSF-IgG1-Fc peaked ~48 h post-injection and did not return to baseline values until ~96 h post-injection. Peak white blood cell and neutrophil levels observed in the rats receiving G-CSF-IgG1 were significantly higher than for the groups receiving wild type recombinant G-CSF or Neupogen® ($p<0.05$). The data indicate that G-CSF-IgG1 is capable of stimulating an increase in circulating neutrophil and white blood cells, and that the absolute increase in peripheral white blood cell counts and neutrophils is greater and longer lasting than that seen with recombinant wild type G-CSF or Neupogen®, even when using a lower molar dose of the fusion protein. G-CSF-IgG1-Fc also stimulated a significant increase in blood monocyte levels over time (Table 7). Similar experiments can be performed to demonstrate efficacy of other G-CSF-IgG and G-CSF (C17S)-IgG fusion proteins (Fc or $C_H$ versions). Similar studies also can be performed using the subcutaneous route for administration of the proteins.

TABLE 5

Effects of G-CSF, Neupogen® and G-CSF-IgG1-Fc on Neutrophil Blood Cell Counts Following Single Intravenous Administration of the Proteins (100 µg/kg)

| Time | Neutrophils Mean +/− SE (cells/µl blood) | | |
|---|---|---|---|
| (Hr) | G-CSF[a] | Neupogen | G-CSF-IgG1-Fc |
| 0 | 1,147 +/− 167 | 1,906 +/− 564 | 2,951 +/− 342 |
| 4 | 6,752 +/− 923 | 4,504 +/− 549 | [b]4,484 +/− 328 |
| 8 | 8,437 +/− 546 | 5,525 +/− 894 | [b]7,309 +/− 890 |
| 12 | 10,744 +/− 549 | 11,891 +/− 1,545 | [b]9,796 +/− 1,649 |
| 24 | 11,035 +/− 788 | 11,148 +/− 977 | [b]13,655 +/− 2,367 |
| 48 | 2,355 +/− 218 | 2,610 +/− 245 | [b,c]14,554 +/− 1,683 |
| 72 | 2,113 +/− 438 | 3,077 +/− 590 | [b,c]6,235 +/− 797 |
| 96 | 2,086 +/− 496 | 2,675 +/− 673 | 3,292 +/− 309 |
| 120 | 2,179 +/− 373 | 2,063 +/− 469 | 3,115 +/− 342 |

[a]Wild type G-CSF prepared by Bolder BioTechnology, Inc.
[b]$p < 0.05$ versus 0 hour neutrophil levels
[c]$p < 0.05$ versus G-CSF and Neupogen at same time point

TABLE 6

Effects of G-CSF, Neupogen® and G-CSF-IgG1-Fc on White Blood Cell Counts Following Single Intravenous Administration of the Proteins (100 µg/kg)

| Time | White Blood Cells Mean +/− SE (cells/µl blood) | | |
|---|---|---|---|
| (Hr) | G-CSF[a] | Neupogen | G-CSF-IgG1-Fc |
| 0 | 11,100 +/− 252 | 11,100 +/− 829 | 14,000 +/− 669 |
| 4 | 16,000 +/− 1,059 | 13,600 +/− 570 | 13,600 +/− 186 |
| 8 | 15,200 +/− 371 | 14,900 +/− 260 | 15,300 +/− 1,670 |
| 12 | 18,400 +/− 240 | 20,100 +/− 674 | 19,400 +/− 2,058 |
| 24 | 23,900 +/− 1,110 | 25,500 +/− 1,734 | [b]29,300 +/− 2,894 |
| 48 | 14,700 +/− 426 | 15,300 +/− 1,715 | [b,c]33,100 +/− 2,099 |
| 72 | 15,300 +/− 426 | 14,800 +/− 764 | [b,c]21,200 +/− 2,228 |
| 96 | 14,200 +/− 1,000 | 14,700 +/− 689 | 15,400 +/− 133 |
| 120 | 11,000 +/− 2,651 | 11,300 +/− 1,477 | 12,900 +/− 2,052 |

[a]Wild type G-CSF prepared by Bolder BioTechnology, Inc.
[b]$p < 0.05$ versus 0 hour white blood cell levels
[c]$p < 0.05$ versus G-CSF and Neupogen at same time point

TABLE 7

Effects of G-CSF, Neupogen and G-CSF-IgG1-Fc on Blood Monocyte Cell Counts Following Single Intravenous Administration of the Proteins (100 µg/kg)

| Time | Monocytes Mean +/− SE (cells/µl blood) | | |
|---|---|---|---|
| (Hr) | G-CSF[a] | Neupogen | G-CSF-IgG1-Fc |
| 0 | 622 +/− 255 | 675 +/− 163 | 804 +/− 208 |
| 4 | 1,837 +/− 60 | 1,320 +/− 215 | 1,364 +/− 296 |
| 8 | 1,519 +/− 168 | 1,044 +/− 79 | 1,025 +/− 234 |
| 12 | 1,166 +/− 51 | 1,482 +/− 315 | 999 +/− 273 |
| 24 | 1,283 +/− 140 | 1,092 +/− 5 | 1,463 +/− 145 |
| 48 | 638 +/− 68 | 825 +/− 147 | 3,167 +/− 111 |
| 72 | 820 +/− 293 | 1,079 +/− 80 | 2,416 +/− 323 |
| 96 | 893 +/− 363 | 1,175 +/− 147 | 1,118 +/− 57 |
| 120 | 786 +/− 56 | 557 +/− 64 | 1,208 +/− 294 |

[a]Wild type G-CSF prepared by Bolder BioTechnology, Inc.

Plasma G-CSF and G-CSF-IgG protein levels can be quantitated using commercially available G-CSF ELISA kits (R & D Systems, Inc.). Titration experiments can be performed to determine the relative sensitivity of the ELISA for detecting wild type G-CSF and G-CSF-IgG fusion proteins. Similar studies can be performed using the subcutaneous route of administration of the proteins.

C. 2. G-CSF-IgG Fusion Protein Efficacy in Normal Mice

For demonstrating efficacy in normal mice, groups of 5 mice (weighing ~20 g each) can receive subcutaneous injections of G-CSF, Neupogen, G-CSF-IgG fusion proteins or placebo (vehicle solution) at specified intervals for up to five days. Normal mice such as ICR mice can be purchased from a commercial vendor such as Jackson Laboratories, Charles River or Harland Sprague Dawley. On day 6 the animals can be sacrificed and blood samples collected for complete blood cell count (CBC) analysis. Hematopoietic tissues (liver and spleen) can be collected, weighed and fixed in formalin for histopathologic analyses to look for evidence of increased granulopoiesis. Bone marrow can be removed from various long bones and the sternum for unit particle preps and histopathologic analysis to look for evidence of increased granulopoiesis. Comparisons between groups can be made using a Students T test for single comparisons and one-way analysis of variance for multiple comparisons. $P<0.05$ can be considered significant. The G-CSF-IgG fusion proteins can stimulate greater increases in circulating neutrophil levels and granulopoiesis in the mice compared to the vehicle-treated mice. Efficacy of the G-CSF-IgG fusion proteins can be tested when administered once on day 1, once per day on days 1-5, every other day on days 1, 3 and 5, or every third day on days 1 and 4. In initial experiments, different groups f mice (weighing ~20 g each) can receive subcutaneous injections of 0.008 to 20 μg per injection of the G-CSF-IgG fusion proteins. Control mice can receive vehicle solution only. Additional control groups can receive wild type G-CSF or Neupogen (2 μg/every day for 5 days) and 2 μg wild type G-CSF using the same dosing regimen as the G-CSF-IgG fusion proteins.

Daily injections of rG-CSF can stimulate increases in circulating neutrophils and granulopoieis in the mice, whereas less frequent administration of the same dose of rG-CSF can not, or can do so to a lesser extent. Dose-dependent increases in these parameters can be observed in the G-CSF-IgG1-Fc-treated animals. Greater increases in these parameters may be observed in the G-CSF-IgG1-Fc-treated animals than in animals treated with rG-CSF using the less frequent dosing schedules. Significantly less G-CSF-IgG1-Fc may give the same increases in these parameters obtained with daily injections of rG-CSF.

3. G-CSF-IgG Fusion Protein Efficacy in Neutropenic Mice: Efficacy of G-CSF-IgG1-Fc also can be demonstrated in neutropenic animals. Neutropenia can be induced by treatment with cyclophosphamide (CPA; 100 mg/kg), which is a commonly used chemotherapeutic agent that is myelosuppressive and relevant to the human clinical setting. G-CSF accelerates recovery of normal neutrophil levels in cyclophosphamide-treated animals (Kubota et al., 1990; Kang et al., 1995). Mice (~20 g) can receive an intraperitoneal injection of cyclophosphamide on day 0 to induce neutropenia. The animals can be divided into different groups of 5 animals each, which will receive subcutaneous injections of G-CSF, G-CSF-IgG1-Fc or placebo for up to five days post-CPA treatment. One control group can not receive cyclophosphamide but can receive placebo injections. The exact dosing schedule to be used can be determined by the results of the pharmacokinetic experiments and normal mouse efficacy studies described above. Experiments can be performed using every day, every other day or every third day dosing schedules over the course of five days. Doses of G-CSF-IgG1-Fc to be tested can be 0.008-20 μg/injection. On day six the animals can be sacrificed and blood and tissue samples analyzed as described above. Alternatively, five mice per group can be sacrificed on days 0-10 and blood and tissue samples analyzed as described for the normal mouse experiments above. The G-CSF-IgG fusion proteins can stimulate an accelerated increase in circulating neutrophil levels and granulopoiesis in the mice compared to the vehicle-injected, CPA-injected control group.

C. GH-IgG Fusion Protein Efficacy

In vivo efficacy of the GH-IgG fusion proteins can be tested in hypophysectomized (HYPOX) rats. This is a well-characterized model of GH deficiency (Cox et al., 1994; Clark et al., 1996). GH stimulates body weight gain and bone and cartilage growth in HYPOX rats (Cox et al., 1994; Clark et al., 1996). Hypophysectomized Sprague-Dawley rats can be purchased from a commercial supplier such as Charles River (Wilmington, Mass.). Typically, rats are hypophysectomized between 40 and 50 days of age and weigh approximately 100-120 g. Groups of 5-8 rats can receive subcutaneous injections of rhGH, GH-IgG or placebo (vehicle solution) at specified intervals and weight gain measured daily over a 10 day period. Rats can be weighed daily at the same time per day to minimize possible variables associated with feeding. In addition to overall weight gain, bone growth (tibial epiphysis width) can be measured. At time of sacrifice, the right and left proximal tibial epiphyses can be removed and fixed in formalin. The fixed tibias can be split at the proximal end in a sagittal plane, stained with silver nitrate and exposed to a strong light (Greenspan et al., 1949). The width of the cartilaginous epiphyseal plate can be measured using a stereomicroscope equipped with a micrometer eyepiece. Ten measurements can be made for each epiphysis and the means +/−SEM for the combined values for the left and right tibias can be calculated. Comparisons between groups can be made using a Students T test for single comparisons and one-way analysis of variance for multiple comparisons. $P<0.05$ can be considered significant.

Efficacy of the GH-IgG fusion proteins can be tested by administering the proteins to the rats daily, every other day, every third day, every fourth day or following a single injection. Five μg of hGH administered twice a day (10 μg/day) by subcutaneous injection gives a strong growth response in the HYPOX rat model (Cox et al., 1994; Clark et al., 1996). In initial experiments different groups of rats can receive subcutaneous injections of various doses of GH-IgG ranging from 0.2 to 200 μg/injection/rat. Control rats can receive vehicle solution only. Additional control groups can receive rhGH (5 μg BID) and 10 μg hGH using the same dosing regimen as the GH-IgG fusion proteins. Administration of the GH-IgG fusion proteins to the HYPOX rats can result in an increase in body weight gain and tibial epyphisis width growth compared to the vehicle-treated group.

Efficacy of the GH-IgG fusion proteins also can be tested in rodent models of cachexia. Dexamethasone (DEX) can be administered to the rats to induce weight loss. Groups of normal Sprague-Dawley rats (200-225 g) can receive daily subcutaneous injections of dexamethasone (200 μg/rat; approximately 1 mg/kg). This amount of dexamethasone can induce a loss of approximately 5-6 g over an 8 d period. Vehicle or varying doses of the GH-IgG can be administered to the rats once, daily, every other day, every third day or every fourth day in different experiments. Different groups of rats can receive subcutaneous injections of 0.2 to 400 μg of the GH-IgG fusion proteins/injection/rat. Additional controls can include a group of rats that will receive no DEX or injections, a group of rats that receives DEX and rhGH (5 mg BID or 10 μg SID) and a group of rats that receives DEX and rhGH (10 μg daily, every other day, every third day, or every fourth day, depending upon the experiment, i.e., frequency that the GH- IgG fusion proteins are administered). Animals can be weighed daily. Food and water consumption can be monitored daily. At time of sacrifice, internal organs can be weighed. Statistical analyses can be performed as described for the HYPOX rat studies. Animals treated with the GH-IgG fusion proteins can lose less weight than the vehicle-treated animals.

Example 9

Further Purification of IgG fusion Protein Dimers

The final purification scheme for the growth factor/cytokine-IgG fusion proteins could include additional column chromatography steps in addition to affinity chromatography to remove protein contaminants and aggregates and to prepare purer preparations of fusion protein tetramers, dimers and monomers. Purer preparations of the Ig fusion proteins can improve their specific activities in in vitro bioassays. For use as human therapeutics it will be preferable to obtain preparations of growth factor/cytokine-IgG monomers substantially free from fusion protein dimers, and preparations of IgG fusion protein dimers substantially free from fusion protein monomers. Growth factor/cytokine-IgG dimers can be separated from IgG fusion protein monomers using a variety of column chromatography procedures known to those with skill in the art. Chromatography procedures also can be used to purify Ig fusion proteins from aggregates and other contaminating proteins. Examples of such chromatography procedures include ion-exchange, size exclusion, hydrophobic interaction, reversed phase, metal chelation, affinity columns, lectin affinity, hydroxy apatite and immobilized dye affinity chromatography. Other useful separation procedures known to those skilled in the art include salt precipitation, solvent precipitation/extraction and polyethylene glycol precipitation. Endotoxin levels in the purified proteins can be tested using commercially available kits to ensure that they are not pyrogenic.

The EPO-IgG4-Fc direct fusion described in Example 4 (encoded by pBBT273) was purified by Protein A affinity chromatography as described in Example 2. The purified protein was further purified by size exclusion chromatography using a Superdex 200 HR 10/30 column. The buffer was 20 mM NaPO4, pH 7.0, 150 mM NaCl. The column volume was 24 ml. The column was eluted with 1.5 column volumes of buffer at a flow rate of 0.5 ml/minute. Fractions of 0.5 ml were collected. A single major protein peak was observed, which eluted with an apparent molecular weight of 204 kDa. The column was calibrated using protein standards purchased from Sigma Chemical Company (catalogue #MW-GF-200). SDS-PAGE analysis under reducing and non-reducing conditions indicated that the major protein peak consisted primarily of disulfide-linked EPO-IgG4-Fc dimers (at least 90%, and probably >95% by non-reducing SDS-PAGE). Large molecular weight contaminants (apparent molecular weights >200 kDa by non-reducing SDS-PAGE) and low molecular weight contaminants (apparent molecular weights <50 kDa by non-reducing SDS-PAGE) were largely removed by this column step.

Similar experiments were performed with the EPO-IgG1-Fc fusion protein encoded by pBBT180, the G-CSF-IgG1-Fc fusion protein encoded by pBBT174 and the G-CSF-IgG4-Fc fusion protein encoded by pBBT175. These proteins were purified by Protein A affinity chromatography as described in Example 2 and then further purified by size-exclusion chromatography as described above. The EPO-IgG1-Fc fusion protein eluted from the sizing column with an apparent molecular weight of 219 kDa and consisted primarily of EPO-IgG1-Fc dimers (>95% by non-reducing SDS-PAGE). The G-CSF-IgG1-Fc fusion protein eluted with an apparent molecular weight of 148 kDa and consisted primarily of G-CSF-IgG1-Fc dimers (>95% by non-reducing SDS-PAGE). The G-CSF-IgG4-Fc fusion protein eluted with an apparent molecular weight of 135 kDa and consisted primarily of G-CSF-IgG4-Fc dimers (at least 90%, and probably >95% by non-reducing SDS-PAGE). Large molecular weight contaminants (apparent molecular weights >200 kDa by non-reducing SDS-PAGE) and low molecular weight contaminants (apparent molecular weights <50 kDa by non-reducing SDS-PAGE) were largely removed by this column step.

Example 10

The procedures described in the preceding examples can, with minor modifications, be used to created IgG fusions with other proteins. Examples of other IgG fusion proteins that would find therapeutic uses in humans include IgG fusions of other members of the GH supergene family, including interferons alpha, beta and gamma, IL-11, TPO, GM-CSF, Stem cell factor and flt3 ligand. DNAs encoding these proteins can be cloned as described below and fused to the various IgG domains described in Example 1. The recombinant fusion proteins can be expressed and purified as described in Example 2 and 9. The purified fusion proteins can be tested in appropriate in vitro bioassays to determine their specific activities. DNA sequences, amino acid sequences and appropriate in vitro and in vivo bioassays for these proteins are well known in the art and are described in Aggarwal and Gutterman (1992; 1996), Aggarwal (1998), and Silvennoimem and Ihle (1996). Bioassays for these proteins also are provided in catalogues of commercial suppliers of these proteins such as R&D Systems, Inc, Endogen, Inc., and Gibco BRL.

1. Cloning human alpha interferon. Alpha interferon is produced by leukocytes and has antiviral, anti-tumor and immunomodulatory effects. There are at least 20 distinct alpha interferon genes that encode proteins that share 70% or greater amino acid identity. Amino acid sequences of the known alpha interferon species is given in Blatt et al., 1996). A "consensus" interferon that incorporates the most common amino acids into a single polypeptide chain has been described (Blatt at al, 1996). A hybrid alpha interferon protein may be produced by splicing different parts of alpha interferon proteins into a single protein (Horisberger and Di Marco, 1995). The following example describes construction of an alpha 2 interferon IgG fusion protein. Similar procedures can be used to create IgG fusions of other alpha interferon proteins.

DNA encoding human alpha interferon (IFN-α2) was amplified by PCR from human genomic DNA (CLONTECH). PCR reactions were carried out with BB93 (5>CGC-GAATTCGGATATGT AAATAGATACACAGTG>3 SEQ.ID.NO.44) and BB94 (5>CGCAAGCTTAAAA-GATTTAAATCGTGTCATGGI>3) (SEQ.ID.NO.45). BB93 anneals to genomic sequences ~300 by upstream (i.e. 5' to) of the IFN-alpha2 coding sequence and contains an Eco RI site for cloning purposes. BB94 anneals to genomic sequences ~100 by downstream (i.e. 3' to) of the IFN-alpha2 coding sequence and contains a Hind III site for cloning purposes. The PCR reaction employed 1×PCR reaction buffer (Promega Corp., Madison Wis.), 1.5 mM $MgCl_2$, 0.2 mM dNTPs, 0.2 µM of each oligonucleotide primer, 0.33 µg of genomic DNA and 0.4 units of Taq polymerase (Promega) in a 33 µl reaction. The reaction consisted of 96° C. for 3 minutes followed by 35 cycles of: [95° C. for 60 sec., 58° C. for 75 sec., 72° C. for 90 sec.] followed by chilling the sample to 6° C. Reactions were carried out in a "Robocycler" thermal cycler (Stratagene Inc., San Diego, Calif.). The resulting ~1 kb PCR product was digested with Eco RI and Hind III and cloned into similarly digested, and alkaline phosphatased, pcDNA3.1(+) (Invitrogen, San Diego, Calif.). A clone having the correct DNA sequence for IFN-α2 (Henco at al, 1985) was identified and designated pBBT160.

In order to construct and express gene fusions of IFN-α2 with IgG coding sequences the IFN-α2 gene was modified at the 5' and 3' ends using PCR based mutagenesis. pBBT160 plasmid DNA was used as template for PCR with forward primer BB108 (5' CGCAAGCTTGCCACCATGGCCT-TGACCTTT GCTTTA-3'; SEQ ID NO:46) and reverse primer BB109 (5'-CGCGGATCCTCCGGATTCCTTACT-TCTTAAACTTTC-3'; SEQ ID NO:47). Primer BB108 anneals to the 5' end of the coding sequence for the IFN-α2 secretion signal and the reverse primer, BB109, anneals to the 3' end of the IFN-α2 coding sequence. The resulting PCR product was digested with Hind III and Bam HI, gel purified and cloned into pcDNA3.1(+) vector that had been digested with Hind III and Bam HI, alkaline phosphatase treated, and gel purified. A clone with the correct DNA sequence (Henco et al., 1985) was designated pcDNA3.1(+)::IFNAfus or pBBT190.

2. Cloning human beta interferon. Beta interferon is produced by fibroblasts and exhibits antiviral, antitumor and immunomodulatory effects. Beta interferon is the product of a single gene. DNA encoding human beta interferon (IFN-β) was amplified by PCR from human genomic DNA (CLONTECH). PCR reactions were carried out with forward primer BB110 (5'-CGCAAGCTTGCCACCATGACCAACAAGT-GTCTCCTC-3') (SEQ.ID.NO.48) and reverse primer BB111 (5'-CGCGGATCCTCCGGAGTTTCGGAGG-TAACCTGTAAG-3') (SEQ.ID.NO.49). Primer BB110 anneals to the 5' end of the coding sequence for the IFN-β secretion signal and the reverse primer, BB111, anneals to the 3' end of the IFN-β coding sequence. The resulting PCR product was digested with Hind III and Bam HI, gel purified and cloned into pcDNA3.1(+) vector that had been digested with Hind III and Bam HI, alkaline phosphatase treated, and gel purified. A clone with the correct DNA sequence (Derynck et al., 1980) was designated pcDNA3.1(+)::IFNB-fus or pBBT191.

3. Cloning human gamma interferon. Gamma interferon is produced by activated T cells and exhibits anti-viral, antitumor and immunomodulatory effects. A cDNA encoding human gamma interferon (IFN-γ) was amplified by PCR from total RNA isolated from the human Jurkat T cell line (available from the American Type Culture Collection, Rockville, Md.). The cells were grown in RPMI media supplemented with 10% FBS, 50 units/ml penicillin and 50 μg/ml streptomycin. The cells were activated in vitro for 6 hours with 1 μg/ml PHA-L (Sigma chemical Company, catalogue L-4144) and 50 ng/ml PMA (phorbol 12-myristate 13-acetate, Sigma Chemical Company, catalogue #P-1585) to induce IFN-γ expression prior to RNA isolation (Weiss et al., 1984; Wiskocil et al., 1985). RNA was isolated from the cells using an RNeasy Mini RNA isolation kit purchased from Qiagen, Inc. (Santa Clarita, Calif.) following the manufacturer's directions. Approximately 104 μg of total RNA was isolated from $2.4 \times 10^7$ cells. First strand synthesis of single-stranded cDNA was accomplished using a 1st Strand cDNA Synthesis Kit for RT-PCR (AMV) from Boehringer Mannheim Corp (Indianapolis, Ind.) and random hexamers were used as the primer. Subsequent PCR reactions using the products of the first strand synthesis as template were carried out with forward primer BB112 (5'-CGCAAGCTTGCCACCATGAAATATA-CAAGTTATATC-3') (SEQ.ID.NO.50) and reverse primer BB113 (5'-CGCGGATCCTCCGGACTGGGATGCTCT-TCGACCTTG-3') (SEQ.ID.NO.51). Primer BB112 anneals to the 5' end of the coding sequence for the IFN-γ secretion signal and the reverse primer, BB113, anneals to the 3' end of the IFN-γ coding sequence. The resulting PCR product was digested with Hind III and Bam HI, gel purified and cloned into pcDNA3.1(+) vector that had been digested with Hind III and Bam HI, alkaline phosphatase treated, and gel purified. A clone with the correct DNA sequence (Gray et al., 1982) was designated pcDNA3.1(+)::IFNGfus or pBBT192.

4. Construction of Interferon-IgG fusions. The IgG1-Fc coding sequence was fused to the carboxyterminus of IFN-α2, IFN-β, and IFN-γ. The ~790 by Bam HI-Xba I fragment was excised from plasmid pBBT167 [described above in Example 1] and cloned into pBBT190, pBBT191 and pBBT192 which had been digested with Bam HI and Xba I, and treated with alkaline phosphatase. Similarly, IgG4-Fc coding sequence also was fused to IFN-α2, IFN-β, and IFN-γ. The ~790 by Bam HI-Xba I fragment of plasmid pBBT158 [described above in Example 1] was excised, gel-purified and cloned into pBBT190, pBBT191 and pBBT192 which had been digested with Bam HI and Xba I, and treated with alkaline phosphatase. The IgG1-$C_H$ coding sequence was fused to the carboxyterminus of IFN-α2, IFN-β, and IFN-γ. The ~1080 by Bam HI-Xba I fragment of plasmid pBBT166 [described above in Example 1] was excised and cloned into pBBT190, pBBT191 and pBBT192 which had been digested with Bam HI and Xba I, and treated with alkaline phosphatase. The structures of the resulting recombinant plasmids were verified by restriction endonuclease digestions and agarose gel electrophoresis. These plasmids and the IFN-IgG fusion proteins that they encode are listed in Table 8.

TABLE 8

| Interferon - IgG Fusion Proteins | |
|---|---|
| Expression Plasmid | IFN Fusion Protein |
| pBBT193 | IFN-α2-IgG1-Fc |
| pBBT194 | IFN-α2-IgG4-Fc |
| pBBT220 | IFN-α2-IgG1-$C_H$ |
| pBBT195 | IFN-β-IgG1-Fc |
| pBBT196 | IFN-β-IgG4-Fc |
| pBBT221 | IFN-β-IgG1-$C_H$ |
| pBBT209 | IFN-γ-IgG1-Fc |
| pBBT210 | IFN-γ-IgG4-Fc |
| pBBT222 | IFN-γ-IgG1-$C_H$ |

5. Bioactivities of Interferon-IgG Fusion Proteins.

5.A. In Vitro Bioactivities

In vitro biological assays for interferons include antiviral assays and cell proliferation inhibition assays. Proliferation of the human Daudi cell line (American Type Culture Collection, Rockville, Md.) is inhibited by alpha, beta and gamma interferon and can be used to assay these proteins (Horoszewicz et al., 1979; Evinger and Pestka, 1981). Daudi cells are maintained in RPMI 1640 media supplemented with 10% FBS, 50 units/ml penicillin and 50 μg/ml streptomycin. Bioassays are performed in this media using the procedures described above except that the number of cells added to each well of a 96 well plate can be $5-20 \times 10^3$ and the plates incubated at 37° C. for 3 to 4 days. The Daudi cells can be at early saturation density ($1-2 \times 10^6$ cells/ml) before use in the assays for optimum effectiveness of the interferon. Serial dilutions of recombinant alpha, beta and gamma interferon (Endogen; R&D Systems; GibcoBRL, US Biological) can be analyzed in parallel. Recombinant alpha interferon has an $IC_{50}$ (the concentration of protein required to inhibit proliferation by 50%) of approximately 5-30 pg/ml.

Bioactivities of alpha, beta and gamma interferons also can be measured using viral plaque inhibition assays. These assays measure the ability of the interferon protein to protect cells from viral infection. Methods for performing these assays are described in Ozes et al., (1992) and Lewis (1987; 1995). Human HeLa or WISH cells (available from the American Type Cuture Collection) can be plated in 96-well plates ($3\times10^4$ cells/well) and grown to near confluency at 37° C. The cells can be washed and treated for 24 hour with serial 2-3-fold dilutions of each IFN-IgG fusion protein preparation. Vesicular stomatitis virus (VSV) or encephalomyocarditis virus (EMCV) can then be added at a multiplicity of infection of 0.1 and the plates incubated for a further 24-48 hours at 37° C. Additional controls can include samples without virus. When 90% or more of the cells have been killed in the virus-treated, no IFN control wells (determined by visual inspection of the wells), the cell monolayer can be stained with crystal violet (0.5% in 20% methanol) and absorbance of the wells read using a microplate reader. Alternatively, 20 μl of MTS/PMS mixture (CellTiter 96 AQueous One Solution, Promega Corporation, Madison, Wis.) can be added to the cell monolayers and absorbance the wells read at 490 nm after 1-4 hours later as described in Example 3. $EC_{50}$ values (the amount of protein required to inhibit the cytopathic effect of the virus by 50%) can be used to compare the relative potencies of the fusion proteins and non-fused wild type proteins. Wild type IFN proteins protect cells from the cytopathic effects of VSV and EMCV and have specific activities of approximately $1\times10^7$ to $2\times10^8$ units/mg in this assay, depending upon the IFN species (Ozes et al., 1992).

The IFN-α-IgG and IFN-β-IgG fusion proteins listed in Table 8 were expressed in COS cells and purified as described in Examples 1 and 2. Non-reducing SDS-PAGE analysis showed that the IFN-α-IgG1-Fc and IFN-α-IgG1-$C_H$ fusion proteins consisted predominantly of disulfide-linked dimers; however small am tints (<10%) of monomeric fusion protein was observed in all of the samples by non-reducing SDS-PAGE. The IFN-α-IgG1-$C_H$ fusion protein also contained a significant amount of disulfide-linked aggregates, which failed to enter the gel. The IFN-α-IgG4-Fc fusion protein also was predominantly dimeric; more monomer was present in this sample than in the IFN-α-IgG1-Fc samples. The IFN-β-IgG1-Fc and IFN-β-IgG1-$C_H$ fusion proteins also were largely dimeric, with small amounts of monomeric fusion protein present in each sample. In contrast, the majority of the purified IFN-β-IgG4-Fc fusion protein was monomeric; the remainder was dimeric. Significant amounts of disulfide-linked aggregates were present in all of the purified IFN-β-IgG fusion proteins.

The purified IFN-α-IgG and IFN-β-IgG fusion proteins were assayed using the Daudi cell growth inhibition assay described above. All of the IFN-α-IgG and IFN-β-IgG fusion proteins were biologically active. $IC_{50}$ values for each protein were calculated and are shown in Table 9. Control recombinant IFN-α and IFN-β were purchased from Endogen, Inc. (Woburn, Mass.) and US Biological (Swampscott, Mass.), respectively.

TABLE 9

Bioactivities of IFN-α-IgG and IFN-β-IgG Fusion Proteins

| Clone | Protein | $IC_{50}$ Range (ng/ml)[1] | Mean $IC_{50}$ (ng/ml) |
|---|---|---|---|
| — | rhIFN-α | 0.015, 0.010 | 0.013 |
| PBBT193 | IFN-α2-IgG1-Fc | 1.8, 2.5 | 2.1 |
| PBBT194 | IFN-α2-IgG4-Fc | 2.5, 3.5 | 3.0 |
| PBBT220 | IFN-α2-IgG1-$C_H$ | 3.5 | 3.5 |
| — | rhIFN-β | 0.18, 0.3 | 0.24 |
| PBBT195 | IFN-β-IgG1-Fc | 175, 200 | 188 |
| PBBT196 | IFN-β-IgG4-Fc | 15, 15 | 15 |
| PBBT221 | IFN-β-IgG1-$C_H$ | 90 | 90 |

[1]Data from individual assays

IFN-gamma-IgG fusion proteins can be expressed in COS cells and purified by Protein A affinity chromatography as described in Example 2. Since IFN-gamma is sensitive to low pH, the fusion protein can be eluted from the affinity column using elution conditions that do not include low pH. One such method would be to elute the gamma interferon-IgG fusion protein with the Gentle Ag/Ab elution buffers available from Pierce Chemical Company (catalogue #21013 and 21014), followed by desalting of the protein on a desalting column.

5. B. In Vitro Activity of IFN-α-IgKC

Plasmid DNA encoding the IFN-α-IgKC fusion protein described in Example 5 was transfected into COS cells and conditioned media collected after three days. Serial dilutions of the conditioned media were tested in the Daudi cell growth inhibition assay. Concentrations of the fusion protein were measured using an IFN-α2 ELISA kit purchased from Endogen, Inc. The conditioned media inhibited proliferation of the Daudi cells. The $IC_{50}$ for the IFN-α-IgKC fusion was estimated to be approximately 20 pg/ml (~0.69 pM). The control non-fused IFN-αprotein inhibited Daudi cell proliferation with an $IC_{50}$ of 6.5 pg/ml (~0.33 pM) in these experiments.

5. C. In Vivo Activity of IFN-IgG Fusion Proteins

IFN-α biological activity is relatively species-specific, which limits the range of preclinical animal models that can be studied. One model that can be used to measure in vivo efficacy of IFN-α-IgG fusion proteins is inhibition of human tumor xenograft growth in athymic nude mice. Human IFN-α2 is not active on mouse cells and inhibition of human tumor xenograft growth in nude mice occurs through a direct antiproliferative effect on the human tumor cells. IFN-α2 inhibits growth of a variety of primary human tumor xenografts and human tumor cell lines in athymic mice (Balkwill et al., 1985; Balkwill, 1986; Johns et al., 1992; Lindner and Borden, 1997). The primary endpoint for the studies can be tumor volume in treated mice. Administration of the IFN-α-IgG fusion proteins will inhibit tumor growth (as measured by tumor volume) in the mice relative to vehicle-treated animals. Athymic nude mice can be purchased from a commercial vendor such as Charles River. Each mouse can be injected with $2\times10^6$ NIH-OVCAR-3 or MCF-7 tumor cells (these cell lines are available from the American Type Culture collection) on day 0 and randomly assigned to test groups, consisting of ten mice each. An appropriate number of cells from another IFN-α-responsive tumor type can be substituted for the NIH-OVCAR-3 or MCF-7 cells. Tumor volumes can be determined at 4 day intervals by measuring the length and width of the tumors with calipers, as described by Linder and Borden (1997). At time of sacrifice, the tumors can be excised and weighed. Mean tumor volumes +/−SEM for each test group can be calculated for each sampling point. Comparisons between groups can be made using a Students T test for single comparisons and one-way analysis of variance for multiple comparisons. Five μg of IFN-α2 administered once per day by subcutaneous injection inhibits growth of NIH-OVCAR-3 cells and MCF-7 cells in athymic mice by 80% after 6 weeks (Lindner and Borden, 1997). Either cell line can be used for these studies. The NIH-OVCAR-3 line (available from the ATCC) does not require estrogen for growth, as do the MCF-7 cells. Xenograft experiments with MCF-7 cells require that the mice be oophorectomized and implanted with estrogen pellets (Lindner and Borden, 1997). In initial experiments, different groups of mice can receive subcutaneous injections of 1 or 5 μg per injection of rIFN-α2, or 0.1 to 100 μg per injection IFN-α-IgG fusion proteins using every day, every other day or every third day dosing schedules. Dosing can begin on day 2 following injection of the tumor cells into the mice. Control mice can receive vehicle solution only. In the every other day and every third day dosing experiments, an additional positive control group can receive daily subcutaneous injections of 5 μg rIFN-α2.

In vivo efficacy of the IFN-β-IgG fusion proteins can be demonstrated in the same tumor xenograft model using similar doses and dosing schedules.

6. IL-11-IgG Fusion Proteins

6.A. Cloning IL-11. IL-11 stimulates development of megakaryocyte precursors of platelets. A cDNA encoding human IL-11 can be amplified by PCR from RNA isolated from human cell lines that express IL-11 such as the human bladder carcinoma cell line 5637 and the HL60 and U937 leukemia cell lines (available from the American Type Culture Collection). PCR reactions can be carried out with forward primer IL-11F (5'-CGCAAGCTTGCCACCATGAACTGT-GTTTGCCGCCTG-3') (SEQ.ID.NO.52) and reverse primer IL-11R (5'-CGCGGATCCTCCGGACAGCCGAGICIT-CAGCAGCAG-3') (SEQ.ID.NO.53). Primer IL-11F anneals to the 5' end of the coding sequence for the IL-11 secretion signal and the reverse primer, IL-11R, anneals to the 3' end of the IL-11 coding sequence. The resulting PCR product can be digested with Hind III and Bam HI, gel purified and cloned into pcDNA3.1(+) vector that has been digested with Hind III and Bam HI, alkaline phosphatase treated, and gel purified. Several clones can be sequenced to identify one with the correct DNA sequence.

Alternatively, the IL-11 coding sequence was amplified by PCR as two segments which were then subsequently spliced together to generate the full length clone by the technique of "overlap extension" as described above in Example 1, section C4 and by Horton et al. (1993). One segment, encoding amino acids 1 through 147, was amplified by PCR from single-stranded cDNA derived from total RNA extracted from the human bladder carcinoma cell line 5637 as detailed in Section 2 B. above. A PCR reaction using the products of the first strand synthesis as template was carried out with forward primer BB265 (5>CGCAAGCTTGCCACCATGAACTG TGTTTGCCGCCTG>3)(SEQ.ID.NO.54) and reverse primer BB273 (5>GCGGGACATCAGGAG CTGCAGC-CGGCGCAG>3)(SEQ.ID.NO.55). Primer BB265 anneals to the 5' end of the coding sequence for the IL-11 secretory signal sequence and the reverse primer, BB273, anneals to sequence encoding amino acids 138-147 and spans the junction of exons 4 and 5 (McKinley et al., 1992). The ~450 by product of this reaction was gel-purified and used in subsequent splicing reactions. The second segment, containing DNA sequences encoding amino acids 142 through 197, was amplified by PCR from human genomic DNA (STRAT-AGENE). A PCR reaction using human genomic DNA as template was carried out with forward primer BB272 (5>CAGCTCCTGATGTCCCGCC TGGCCCTG>3)(SEQ.ID.NO.56) and reverse primer BB274 (5>AGTCTTCAG-CAGCAGCAGTCCCC TCAC>3) (SEQ.ID.NO.57). BB272 anneals to sequence encoding amino acids 142-150 and spans the junction of exons 4 and 5. BB274 anneals to sequence encoding amino acids 189-197. The ~170 bp product of this reaction was gel-purified and used in subsequent splicing reactions.

The gel purified ~450 by and ~170 by products were spliced together in a PCR reaction which included the ~450 by and ~170 by products as template and forward primer BB265 (described above) and reverse primer BB275 (5>CGCGGATCCTCC GGACAGCCGAGTCTTCAG-CAGCAG>3)(SEQ.ID.NO.58). BB275 anneals to the DNA sequence encoding amino acids 191-199. The ~620 by product of this reaction was gel-purified, digested with Hin dIII and Bam HI and cloned into pcDNA3.1(+) vector that had been digested with Hind III and Bam HI, alkaline phosphatase treated, and gel purified. A clone with the correct DNA sequence was designated pcDNA3.1(+)::IL-11fus or pBBT298.

6.B. Construction of IL-11-IgG fusions. The IgG1-Fc coding sequence was fused to the carboxyterminus of IL-11. The ~790 by Bam HI-Xba I fragment was excised from plasmid pBBT174 [described above in Example 2, see Table 1] and cloned into pBBT298 which had been digested with Bam HI and Xba I, and treated with alkaline phosphatase. Similarly, IgG4-Fc coding sequence also was fused to the carboxyterminus of IL-11. The ~790 by Bam HI-Xba I fragment of plasmid pBBT175 [described above in Example 2, see Table 1] was excised, gel purified and cloned into pBBT298 which had been digested with Bam HI and Xba I, and treated with alkaline phosphatase. The IgG1-$C_H$ and IgG4-$C_H$ coding sequences also were fused to the carboxyterminus of IL-11. The IgG1-$C_H$ and IgG4-$C_H$ coding sequences were excised as ~1080 by Bam HI-Xba I fragments from plasmids pBBT173 and pBBT184 [described above in Example 2, see Table 1] respectively, and cloned into pBBT298 which had been digested with Bam HI and Xba I, and treated with alkaline phosphatase. The structures of all the resulting recombinant plasmids were verified by restriction endonuclease digestions and agarose gel electrophoresis. These plasmids and the IL-11-IgG fusion proteins they encode are listed in Table 10.

TABLE 10

| IL-11 - IgG Fusion Proteins | |
| --- | --- |
| Expression Plasmid | IL-11-Fusion Protein |
| pBBT336 | IL-11-IgG1-Fc |
| pBBT337 | IL-11-IgG4-Fc |
| pBBT338 | IL-11-IgG1-$C_H$ |
| pBBT339 | IL-11-IgG4-$C_H$ |

An IL-11-IgG1-Fc direct fusion can be created by PCR using plasmid pBBT336 as the DNA template. One PCR reaction can use oligos IL11DFA (5' CTGAAGACTCG-GCTGGA GCCCAAATCTTGTGACAAA-3') (SEQ.ID.NO.59) and BB82. The second PCR reaction can use oligos IL11DFB (5' ACAAGATTTGGGCTCCAGC-CGAGTCTTCAGCAGCAG-3')(SEQ.ID.NO.60) and BB272. The products from these PCR reactions can be gel-purified, mixed and subjected to a third PCR reaction using oligos BB82 and BB272. The approximate 800 by PCR product can be gel-purified, digested with and Sgr AI III and Sac II, and cloned into similarly cut pBBT336 that had been treated with calf intestinal phosphatase. A clone with the correct insert can be identified by DNA sequencing.

An IL11-IgG4-Fc direct fusion can be created by PCR using plasmid pBBT337 as the DNA template. One PCR reaction can use oligos IL11DFC (5-CTGAAGACTCG-GCTGGAGTC CAAATATGGTCCCCCA-3') (SEQ.ID.NO.61) and BB82. The second PCR reaction can use oligos IL11DFD (5'-ACCATATTTGACTCCAGC-CGAGTCTTCAGCAGCAG-3') (SEQ.ID.NO.62) and BB272. The products from these PCR reactions can be gel-purified, mixed and subjected to a third PCR reaction using oligos BB82 and BB272. The approximate 800 by PCR product can be gel-purified, digested with and Sgr AI and Sac II, and cloned into similarly cut pBBT337 that has been treated with calf intestinal phosphatase. A clone with the correct insert can be identified by DNA sequencing.

The B9-11 cell line (Lu et al., 1994), the T11 cell line (R & D Systems) or another IL-11-dependent cell line can be used t measure bioactivities f the IL-11-IgG fusion proteins. An IL-11-dependent cell line can be created by culturing the B9 cell line (available from the German Collection of Microorganisms and Cell Cultures, Braunschweig, Germany) in RPMI 1640 media containing 10% FBS, 50 units/ml penicillin and 50 µg/ml streptomycin and 50-100 ng/ml of IL-11 for several days to several months, followed by limiting dilution cloning of the cells to select for individual lines.

6.C. In Vivo Efficacy of IL-11-IgG Fusion Proteins

The IL-11-IgG fusion proteins will stimulate increases in circulating platelets and megakaryopoiesis in normal mice or rats, similar to what is seen for hIL-11 and bTPO (Lok et al., 1994; Kaushansky et al., 1994; Neben et al., 1993; Yonemura et al., 1993). Efficacy of the IL-11-IgG fusion proteins can be tested in normal animals using every other day, every third day or single injection dosing schedules. Effectiveness of the IL-11-IgG fusion proteins also can be demonstrated in rodent chemotherapy-induced thrombocytopenia models (Hangoc et al., 1993; Leonard et al., 1994), using every other day, every third day or single injection dosing schedules.

Groups of mice or rats can receive subcutaneous injections of rhIL-11, IL-11-IgG fusion protein or placebo (vehicle solution) at specified intervals (daily, every other day, every third day) for up to seven days. A wide range of IL-11-IgG fusion protein doses can be tested in these initial experiments to increase the likelihood that one of the doses will be effective. The dose range of the IL-11-IgG fusion proteins to be tested can range from 0.002× to 25× the optimum dose of IL-11 previously determined for these animal models. It is possible that administration of too much of the fusion proteins will impede megakarypoiesis due to toxicity. Control animals can receive vehicle solution only. Additional control groups can receive daily subcutaneous injections of rhIL-1. On day 7 the animals can be sacrificed and blood samples collected for complete blood cell count analysis. Hematopoietic tissues (liver and spleen) can be collected, weighed and fixed in formalin for histopathologic analyses to look for evidence of increased megakaryopoiesis. Bone marrow can be removed from various long bones and the sternum for unit particle preps and histopathologic analysis to look for evidence of increased megakaryopoiesis. Comparisons between groups can be made using a Students T test for single comparisons and one-way analysis of variance for multiple comparisons. P<0.05 will be considered significant. The IL-11-IgG fusion proteins will stimulate increases in circulating platelets and megakaryopoiesis in the animals.

7. TPO-IgG fusion Proteins

7. A. Cloning TPO. Thrombopoietin (TPO) stimulates development of megakaryocyte precursors of platelets. A cDNA encoding human TPO was amplified by PCR from single-stranded cDNA prepared from human adult and fetal liver (CLONTECH, Inc.). Single-stranded cDNA prepared from fetal or adult kidney (CLONTECH) also can be used to amplify TPO. PCR reactions were carried out with forward primer BB343 (5'-CGCAAGCTTGCCACCATGGAGCT-GACTGAATTGCTC-3') (SEQ.ID.NO.63) and reverse primer BB344 (5'-CGCGGATCCTCCGGACCCTTCC TGAGACAGATTCTG-3') (SEQ.ID.NO.64). Primer BB343 anneals to the 5' end of the coding sequence for the TPO secretion signal and the reverse primer, BB344, anneals to the 3' end of the TPO coding sequence.

The sequence encoding TPO contains an internal Bam HI site and this site was used to clone the ~1000 by TPO coding sequence as two segments; an amino-terminal Hind III-Bam HI fragment of ~400 by and a carboxy-terminal Bam HI fragment of ~600 bp. Each of these fragments was first cloned and sequenced and subsequently ligated together through the internal Bam HI site to generate the complete TPO coding sequence. The ~1,000 by PCR product was digested with Hin dIII and Bam HI to generate a Hin dIII-Bam HI fragment of ~400 by and a Bam HI fragment of ~600. These fragments were gel-purified and cloned into pcDNA3.1(+) vector that had been digested with Hind III and Bam HI, or only Bam HI, respectively, alkaline phosphatase treated, and gel purified. Clones with the correct DNA sequences (Foster et al., 1994; Sohma et al., 1994) for each fragment were identified. The 600 by Bam HI fragment was then excised from the sequence-verified clone and cloned into Bam HI-cut, alkaline phosphatase-treated and gel-purified pcDNA3.1(+) derivative containing the sequence verified 400 by Hin dIII-Bam HI fragment. The resulting clones were analyzed by restriction endonuclease digestion and PCR to identify those that carried the 600 by Bam HI fragment cloned in the proper orientation i.e., so that the coding sequence for TPO is properly reconstituted. One properly oriented clone was designated pcDNA3.1(+)::TPOfus, or pBBT355, and used in further constructions.

7. B. Construction of TPO-IgG fusions. Fusions of IgG coding sequences to the carboxy-terminus of TPO were constructed using procedures analogous to those used to construct the IL-1'-IgG fusions with the exception that restriction endonuclease Bsp EI was used in place of Bam HI because the coding sequence for TPO contains a Bam HI site. The sequence employed to encode the ser-gly-gly-ser-gly-gly-ser (SEQ.ID.NO.3) linker peptide in all of the constructs described in Examples 1, 2 and 10 contains a single Bsp EI recognition site (TCCGGA) and this site does not occur within the pcDNA3.1(+) vector or the IgG1-Fc, IgG4-Fc, IgG1-$C_H$, and IgG4-$C_H$ coding sequences.

The IgG1-Fc coding sequence was fused to the carboxy-terminus of TPO. The ~790 by Bsp EI-Xba I fragment was excised from plasmid pBBT174 [described above in Example 2, see Table 1] and cloned into pBBT355 which had been digested with Bsp EI and Xba I, and treated with alkaline phosphatase. Similarly, IgG4-Fc coding sequence also was fused to the carboxyterminus of TPO. The ~790 by Bsp EI-Xba I fragment of plasmid pBBT175 [described above in Example 2, see Table 1] was excised, gel-purified and cloned into pBBT355 which had been digested with Bsp EI and Xba I, and treated with alkaline phosphatase. The IgG1-$C_H$ and IgG4-$C_H$ coding sequences also were fused to the carboxy-terminus of TPO. The IgG1-$C_H$ and IgG4-$C_H$ coding sequences were excised as ~1080 by Bsp EI-Xba I fragments from plasmids pBBT173 and pBBT184 [described above in Example 2, see Table 1] respectively, and cloned into pBBT355 which had been digested with Bsp EI and Xba I, and treated with alkaline phosphatase. The structures of all the resulting recombinant plasmids were verified by restriction endonuclease digestions and agarose gel electrophoresis. Table 11 lists these plasmids and the TPO-IgG fusion proteins they encode.

TABLE 11

TPO - IgG Fusion Proteins

| Expression Plasmid | TPO Fusion Protein |
|---|---|
| pBBT340 | TPO-IgG1-Fc |
| pBBT341 | TPO-IgG4-Fc |
| pBBT342 | TPO-IgG1-$C_H$ |
| pBBT343 | TPO-IgG4-$C_H$ |

The amino-terminal domain of TPO, consisting of amino acids 1-153 of the mature TPO protein has been shown to be sufficient for megakaryopoiesis (Bartley et al., 1994, de Sauvage et al., 1994). This domain could be subcloned by PCR from the TPO coding sequence in pBBT355 (described above) and fused to immunoglobulin sequences. The PCR reaction would be carried out using forward primer BB343 (described above) and reverse primer TPO153rev (5>CGC GGA TCC TCC GGA CCT GAC GCA GAG GGT GGA CCC>3)(SEQ.ID.NO.65). Primer TPO153rev anneals to the TPO sequence encoding amino acids 147 through 153 and adds a portion of the flexible linker containing a Bam HI site. The template for this reaction would be pBBT355 DNA. The resulting PCR product of 600 by would be digested with Bam HI and the resulting ~105 by Bam HI fragment would be gel purified, cloned in pUC18 and sequenced. A clone having the correct sequence would then be used as a source of plasmid DNA from which the ~105 by Bam HI fragment would be gel purified. This fragment would be used to replace the ~600 by Bam HI fragment present in pBBT340, pBBT341, pBBT342 and pBBT343 (which are all described above). This will result in construction of fusion proteins consisting of amino acids 1-153 of TPO fused via the ser-gly-gly-ser-gly-gly-ser linker to IgG1-Fc, IgG4-Fc, IgG1-$C_H$, and IgG4-$C_H$ respectively.

A TPO-IgG1-Fc direct fusion can be created by PCR using plasmid pBBT340 as the DNA template. One PCR reaction can use oligos TPODFA (5' CTGTCTCAGGAAGGGGAG CCCAAATCTTGTGACAAA-3') (SEQ.ID.NO.66) and BB82. The second PCR reaction can use oligos TPODFB (5' ACAAGATTTGGGCTCCCCTTCCTGAGA-CAGATTCTG-3) (SEQ.ID.NO.67) and BB91. The products from these PCR reactions can be gel-purified, mixed and subjected to a third PCR reaction using oligos BB82 and BB91. The approximate 1700 by PCR product can be gel-purified, digested with and Rind III and Sac II, and cloned into similarly cut pBBT340 that had been treated with calf intestinal phosphatase. A clone with the correct insert can be identified by DNA sequencing.

A TPO-IgG4-Fc direct fusion can be created by PCR using plasmid pBBT341 as the DNA template. One PCR reaction can use oligos TPODFC (5-CTGTCTCAGGAAGGG-GAGTCCAAA TATGGTCCCCCA-3') (SEQ.ID.NO.68) and BB82. The second PCR reaction can use oligos TPODFD (5'-ACCATATTTGGACTCCCCTTCCTGAGA-CAGATTCTG-3'SEQ.ID.NO.69) and BB91. The products from these PCR reactions can be gel-purified, mixed and subjected to a third PCR reaction using oligos BB82 and BB91. The approximate 2000 by PCR product can be gel-purified, digested with and Hind III and Sac II, and cloned into similarly cut pBBT341 that has been treated with calf intestinal phosphatase. A clone with the correct insert can be identified by DNA sequencing.

Similar methods could be used to construct analogous direct fusions encoding only amino acids 1-153 of TPO fused to IgG-Fc domains.

The cell line M-O7e (Avanzi et al., 1988; available from the German Collection of Microorganisms and Cell Cultures, Braunschweig, Germany) can be used to measure TPO-IgG fusion protein bioactivity.

7.C. In Vivo Efficacy of TPO-IgG Fusion Proteins

The TPO-IgG fusion proteins will stimulate increases in circulating platelets and megakaryopoiesis in normal mice or rats, similar to what is seen for hIL-11 and hTPO (Lok et al., 1994; Kaushansky et al., 1994; Neben et al., 1993; Yonemura et al., 1993; Kaszubska et al., 2000). Efficacy of the TPO-IgG fusion proteins can be tested in normal animals using every other day, every third day or single injection dosing schedules. Effectiveness of the TPO-IgG fusion proteins also can be demonstrated in rodent chemotherapy-induced thrombocytopenia models (Hanggoc et al., 1993; Leonard et al., 1994), using every other day, every third day or single injection dosing schedules.

Groups of mice or rats can receive subcutaneous injections of rhTPO, TPO-IgG fusion protein or placebo (vehicle solution) at specified intervals (daily, every other day, every third day) for up to seven days. A wide range of TPO-IgG fusion protein doses can be used in these initial experiments to increase the likelihood that one of the doses will be effective. The dose range of the TPO-IgG fusion proteins to be tested can range from 0.002× to 25× the optimum dose of TPO previously determined for these animal models. It is possible that administration of too much of the fusion proteins will impede megakaryopoiesis due to toxicity. Control animals can receive vehicle solution only. Additional control groups can receive daily subcutaneous injections of rhTPO. On day 7 the animals can be sacrificed and blood samples collected for complete blood cell count analysis. Hematopoietic tissues (liver and spleen) can be collected, weighed and fixed in formalin for histopathologic analyses to look for evidence of increased megakaryopoiesis. Bone marrow can be removed from various long bones and the sternum for unit particle preps and histopathologic analysis to look for evidence of increased megakaryopoiesis. Comparisons between groups can be made using a Students T test for single comparisons and one-way analysis of variance for multiple comparisons. $P<0.05$ will be considered significant. The TPO-IgG fusion proteins will stimulate increases in circulating platelets and megakaryopoiesis in the animals.

8. GM-CSF-IgG Fusion Proteins

8.A. Cloning GM-CSF: A cDNA encoding human Granulocyte Macrophage Colony Stimulating Factor (GM-CSF) was amplified by PCR from total RNA prepared from the human bladder carcinoma cell line 5637 as detailed in Section 2 B. above. A PCR reaction using the products of the first strand synthesis as template was carried out with forward primer BB263 (5>CGCAAGCTTGCCACCATGTGGCTGCA-GAGC CTGCTG>3) (SEQ.ID.NO.70) and reverse primer BB264 (5>CGCGGATCCTCCGGACTCCTGGACTGGCT CCCAGCA>3)(SEQ.ID.NO.71). Primer BB263 anneals to the 5' end of the coding sequence for the GM-CSF secretion signal and the reverse primer, BB264, anneals to the 3' end of the GM-CSF coding sequence. The resulting ~450 by PCR product was digested with Hind III and Bam HI, gel purified and cloned into pcDNA3.1(+) vector that had been digested with Hind III and Bam HI, alkaline phosphatase treated, and gel purified. A clone with the correct DNA sequence (Cantrell et al., 1985) was designated pcDNA3.1(÷)::GM-CSFfus or pBBT267.

Alternatively, a cDNA encoding human GM-CSF can be amplified by PCR from RNA isolated from a cell line that expresses GM-CSF such as the human T cell line HUT 102 (available from American Type Culture Collection) or from human peripheral blood lymphocytes or the human Jurkat T cell line that had been activated with 20 µg/ml concanavalin A (Sigma Chemical Company) and 40 ng/ml phorbol myristate acetate (PMA, Sigma Chemical Company). PCR reactions can be carried out with forward primer BB263 and reverse primer BB264. The resulting ~450 by PCR product can be digested with Hind III and Bam HI, gel purified and cloned into pcDNA3.1(+) vector that has been digested with Hind III and Bam HI, alkaline phosphatase treated, and gel purified. Several clones can be sequenced to identify one with the correct DNA sequence.

8. B. Construction of GM-CSF-IgG (GF-IgG) fusions. The IgG1-Fc coding sequence can be fused to the carboxy-terminus of GM-CSF. The ~790 by Bam HI-Xba I fragment excised from plasmid pBBT174 [described above in Example 2, see Table 1] can be cloned into pBBT267 that has been digested with Bam HI and Xba I, and treated with alkaline phosphatase. Similarly, IgG4-Fc coding sequence also can be fused to the carboxy-terminus of GM-CSF. The ~790 by Bam HI-Xba I fragment excised from plasmid pBBT175 [described above in Example 2, see Table 1] can be cloned into pBBT267 that has been digested with Bam HI and Xba I, and treated with alkaline phosphatase. The IgG1-$C_H$ and IgG4-$C_H$ coding sequences also can be fused to the carboxy-terminus of GM-CSF. The IgG1-$C_H$ and IgG4-$C_H$ coding sequences were excised as ~1080 by Bam HI-Xba I fragments from plasmids pBBT173 and pBBT184 [described above in Example 2, see Table 1] respectively, and can be cloned into pBBT267 that has been digested with Bam HI and Xba I, and treated with alkaline phosphatase. The structures of all the resulting recombinant plasmids can be verified by restriction endonuclease digestions and agarose gel electrophoresis. Bioactivity of the GM-CSF-IgG fusion proteins can be measured using the TF-1 cell line (available from the American Type Culture Collection).

A GM-CSF-IgG1-Fc direct fusion can be created by PCR using plasmid pcDNA3.1::GM-CSF-IgG1-Fc as the DNA template. One PCR reaction can use oligos GMCSFDFA (5' GAGCCAGTCCAGGAGGAGCCCAAATCT-TGTGACAAA-3'; SEQ ID NO:72) and BB82 (SEQ ID NO:14). The second PCR reaction can use oligos GMCS-FDFB (5' ACAAGATTTGGGCTCCTCCTGGACTG-GCTCCCAGCA-3; SEQ ID NO:73) and BB91 (SEQ ID NO:11). The products from these PCR reactions can be gel-purified, mixed and subjected to a third PCR reaction using oligos BB82 and BB91. The approximate 1150 by PCR product can be gel-purified, digested with and Hind III and Sac II, the resulting ~675 by Hind III/Sac II fragment gel-purified and cloned into similarly cut plasmid pcDNA3.1::GM-CSF-IgG1-Fc that had been treated with calf intestinal phosphatase. A clone with the correct insert can be identified by DNA sequencing.

A GM-CSF-IgG4-Fc direct fusion can be created by PCR using plasmid pcDNA3.1::GM-CSF-IgG4-Fc as the DNA template. One PCR reaction can use oligos GMCSFDFC (5'-GAGCCAGTCCAGGAGGAGTCCAAATATG-GTCCCCCA-3') (SEQ.ID.NO.74) and BB82. The second PCR reaction can use oligos GMCSFDFD (5'-AC-CATATTTGGACTCCTCCTGGACTGGCTCCCAGCA-3') (SEQ.ID.NO.75) and BB91. The products from these PCR reactions can be gel-purified, mixed and subjected to a third PCR reaction using oligos BB82 and BB91. The approximate 1150 by PCR product can be gel-purified, digested with and Hind III and Sac II, the ~675 by Hind III/Sac II fragment gel-purified and cloned into similarly cut plasmid pcDNA3.1::GM-CSF-IgG4-Fc that has been treated with calf intestinal phosphatase. A clone with the correct insert can be identified by DNA sequencing.

Bioactivity of the GM-CSF-IgG fusion proteins can be measured using the TF-1 cell line (available from the American Type Culture Collection).

8. C. In Vivo efficacy of GM-CSF-IgG Fusion Proteins

GM-CSF stimulates granulopoiesis and an increase in circulating neutrophil levels in normal and neutropenic humans and animals. Efficacy of the human GM-CSF-IgG fusion proteins can be determined in non-human primates (Donahue et al., 1986a, 1986b; Mayer et al., 1987a, 1987b) and dogs (Schuening et al., 1989; Mayer et al., 1990), where injection of the protein can stimulate an increase in circulating neutrophil levels over time. Alternatively, analogous IgG fusion proteins to those described here can be made using mouse GM-CSF (Gough et al., 1984; 1985; Kajigaya et al., 1986; Cantrell et al., 1985) and the proteins expressed and purified as described for the human GM-CSF cysteine muteins. In vitro bioactivities of the proteins can be measured using the murine NFS60 or DA-3 cells lines. Efficacy of the mouse GM-CSF-IgG fusion proteins can be measured in mice made neutropenic by injection of cyclophosphamide at a dose of 200 mg/kg (Mayer et al., 1991; Gamba-Vitalo et al., 1991) using once per day, every other day or every third day dosing schedules for the murine GM-CSF-IgG fusion proteins. Doses of the GM-CSF IgG fusion proteins ranging from 0.5 µg/kg to 650 µg/kg per injection can be tested.

9. Stem Cell Factor-IgG Fusion Proteins

9. A. Cloning Stem Cell Factor (SCF): SCF regulates development of hematopoietic progenitor cells. A cDNA encoding human SCF can be amplified by RT-PCR using RNA isolated an from HepG2, 5637 or HT-1080 cell lines (Martin et al., 1990; the HepG2 and 5637 cell lines are available from the ATCC, Rockville, Md.). PCR reactions can be carried out with forward primer SCF-F (5'-CGCAAGCTTGCCACC <u>ATGAAGAAGACACAAACT</u>-3') (SEQ.ID.NO.76) and reverse primer SCF-R (5'-CGCGGATCCTCCGGA <u>GTGTAGGCTGGAGTCTCCAGG</u>-3') (SEQ.ID.NO.77). SCF DNA sequences in the primers are underlined. Primer SCF-F anneals to the 5' end of the coding sequence for the SCF secretion signal and the reverse primer, SCF-R, anneals to the 3' end of the SCF coding sequence, beginning at the junction of the extracellular and transmembrane domains. Other reverse PCR primers can be used to create truncated forms of the SCF extracellular domain, in particular a form that terminates following Ala-174 of the mature protein, by substituting appropriate nucleotides for the SCF DNA sequence listed in SCF-R. The resulting PCR product can be digested with Hind III and Bam HI, gel purified and cloned into pcDNA3.1(+) vector that has been digested with Hind III and Bam HI, alkaline phosphatase treated, and gel purified. Several clones can be sequenced to identify one with the correct DNA sequence. IgG1-Fc, IgG4-Fc, IgG1-$C_H$, IgG4-$C_H$ and kappa light chain constant regions can be fused to the carboxy-terminus of the extracellular domain of SCF as described in Examples 1 and 5. The cell line TF-1 (Kitamura, 1989; available from the American Type Culture Collection, Rockville, Md.) can be used to measure bioactivity of SCF-IgG fusion proteins.

Direct fusions of the extracellular domain of SCF to various IgG domains can be constructed using procedures similar to those described in Example 4 for constructing EPO-IgG and G-CSF-IgG direct fusions. A SCF-IgG1-Fc direct fusion can be created by PCR using plasmid pcDNA3.1::SCF-IgG1-Fc7AA as the DNA template. One PCR reaction can use oligos SCFDFF (5'-GACTCCAGCCTACACGAGC-CCAAATCTTGTGACAAA-3'). (SEQ.ID.NO.78) and BB82. The second PCR reaction used oligos SCFDFR (5'-ACAAGATTTGGGCTCGTGTAGGCTG-GAGTCTCCAGG-3'; SEQ.ID.NO.79) and BB91. The products from these PCR reactions can be gel-purified, mixed and subjected to a third PCR reaction using oligos BB82 and BB91. The PCR product can be gel-purified, digested with and Hind III and Sac II, and cloned into similarly cut pcDNA3.1:: SCF-IgG1-Fc7AA that had been treated with calf intestinal phosphatase. A clone with the correct insert can be identified by DNA sequencing.

A SCF-IgG4-Fc direct fusion can be created by PCR using plasmid pcDNA3.1:: SCF-IgG4-Fc7AA as the DNA template. One PCR reaction can use oligos SCFDFC (5'-GACTCCAGCCTACACGAGTCCAAATATG-GTCCCCCA-3') (SEQ.ID.NO.80) and BB82. The second PCR reaction can use oligos SCFDFD (5'-ACCATATTTG-GACTCGTGTAGGCTGGAGTCTCCAGG-3') (SEQ.ID.NO.81) and BB91. The products from these PCR reactions can be gel-purified, mixed and subjected to a third PCR reaction using oligos BB82 and BB91. The PCR product can be gel-purified, digested with and Hind III and Sac II, and cloned into similarly cut pcDNA3.1::SCF-IgG4-Fc7AA that has been treated with calf intestinal phosphatase. A clone with the correct insert can be identified by DNA sequencing.

10. Flt-3L-IgG fusion Proteins: Flt-3L (Lyman et al., 1993; Hannum et al., 1994) is a membrane bound cytokine that regulates development of hematopoietic stem cells. A cDNA encoding human Flt-3L can be amplified by PCR from single-stranded cDNA prepared from adult or fetal liver, kidney, heart, lung, or skeletal muscle, which is available from commercial sources such as CLONTECH and Stratagene, Inc. PCR reactions can be carried out with forward primer fltF (5'-CGCAAGCTTGCCACCATGACAGTGCTG-GCGCCAGCC-3') (SEQ.ID.NO.82) and reverse primer fltR (5'-CGCGGATCCTCCGGAAGGGGGCT-GCGGGGCTGTCGG-3') (SEQ.ID.NO.83). Flt-3L DNA sequences in the primers are underlined. Primer fltF anneals to the 5' end of the coding sequence for the Flt-3L secretion signal and the reverse primer, fltR, anneals to the 3' end of the Flt3 coding sequence, beginning at the junction of the extracellular and transmembrane domains. Other reverse PCR primers can be used to create truncated forms of the Flt-3L extracellular domain by substituting appropriate nucleotides for the Flt-3L DNA sequence listed in primer fltR. The resulting PCR product can be digested with Hind III and Bam HI, gel purified and cloned into pcDNA3.1(+) vector that has been digested with Hind III and Bam HI, alkaline phosphatase treated, and gel purified. Several clones can be sequenced to identify one with the correct DNA sequence. IgG1-Fc, IgG4-Fc, IgG1-$C_H$, IgG4-$C_H$ and kappa light chain constant regions can be fused to the carboxy-terminus of the extracellular domain of Flt-3L as described in Examples 1 and 5. Ba/F3 cells transfected with the human Flt-3 receptor (Lyman et al., 1993; Hannum et al., 1994) can be can be used to measure bioactivity of Flt-3L-IgG fusion proteins. Ba/F3 cells are available from the German Collection of Microorganisms and Cell Cultures (Braunschweig, Germany).

Direct fusions of the extracellular domain of Flt-3L to various IgG domains can be constructed using procedures similar to those described in Example 4 for constructing EPO-IgG and G-CSF-IgG direct fusions. A Flt-3L-IgG1-Fc direct fusion can be created by PCR using the pcDNA3.1:: Flt-3L-IgG1 plasmid described above as the DNA template. One PCR reaction can use oligos FltDFA (5'-GCCCCG-CAGCCCCCTGAGCCCAAATCTTGTGACAAA-3'(SE-Q.ID.NO.84) and BB82. The second PCR reaction can use oligos Flt3DFB (5'-ACAAGATTTGGGCTCAGGGGGCT-GCGGGGCTGTCGG-3') (SEQ.ID.NO.85) and BB91. The products from these PCR reactions can be gel-purified, mixed and subjected to a third PCR reaction using oligos BB82 and BB91. The PCR product can be gel-purified, digested with and Hind III and Sac II, and cloned into similarly cut pcDNA3.1::SCF-IgG1-Fc7AA that had been treated with calf intestinal phosphatase. A clone with the correct insert can identified by DNA sequencing.

A Flt-3L-IgG4-Fc direct fusion can be created by PCR using plasmid pcDNA3.1::Flt3-IgG4-Fc7AA as the DNA template. One PCR reaction can use oligos FltDFC (5'-GC-CCCGCAGCCCCCTGAGTCCAAATATGGTCCCCCA-3') (SEQ.ID.NO.86) and BB82. The second PCR reaction can use oligos FltDFD (5'-ACCATATTTGGACT-CAGGGGGCTGCGGGGCTGTCGG-3') (SEQ.ID.NO.87) and BB91. The products from these PCR reactions can be gel-purified, mixed and subjected to a third PCR reaction using oligos BB82 and BB91. The PCR product can be gel-purified, digested with Hind III and Sac II, and cloned into similarly cut pcDNA3.1::SCF-IgG4-Fc7AA that has been treated with calf intestinal phosphatase. A clone with the correct insert can be identified by DNA sequencing.

Example 11

Multimeric Cytokine and Growth Factor Fusion Proteins

Bioactive fusion proteins also can be created by constructing multimeric fusion proteins of the growth factors and cytokines mentioned in this application. These multimeric fusion proteins can be constructed as described for the IgG fusion proteins except that a second growth factor/cytokine protein can be substituted for the IgG domain. The two growth factors/cytokines can be joined together with or without linker amino acids between the two growth factors/cytokines. Suitable peptide linkers include those described in Examples 1 and 4. The fusion proteins can be homodimeric, heterodimeric, homomultimeric (comprising three or more copies of the same growth factor/cytokine) or heteromultimeric (comprising two or more different growth factors/cytokines). The most carboxy-terminal cytokine/growth factor domain can be modified using procedures such as PCR to delete the protein's natural signal sequence and add, if desired, a short peptide linker sequence preceding the first amino acid of the mature protein sequence. The linker sequence could include a restriction enzyme site to facilitate joining to the amino-terminal cytokine/growth factor domain. In multimeric fusion proteins the cytokine/growth factor domains not at the amino- or carboxy-terminus of the protein can be modified to delete the natural signal sequence and termination codon and add, if desired, peptide linkers to the amino- and carboxy-termini of the protein. The fusion proteins can expressed in COS cells following transfection, purified and tested in appropriate in vitro bioassays. The fusion proteins also can be expressed in stably transformed eukaryotic cells such as mammalian cells, as described in Example 12.

Example 12

Expression of IgG Fusion Proteins and Multimeric Growth Factors/Cytokines in Stably Transformed Eukaryotic Cells The IgG Fusion proteins and multimeric cytokines/growth factors described in the preceding Examples also can be expressed in stably transformed eukaryotic cells such as insect cells or mammalian cells using well established procedures. The IgG fusion proteins and multimeric cytokines/growth factors are then purified from the conditioned media. Stably transfected CHO cell lines are widely used for high-level expression of recombinant proteins (Geisse et al. 1996; Trill et al. 1995). In CHO cells, high level expression of chromosomally integrated heterologous genes can be achieved by gene amplification. Typically the gene of interest is linked to a marker gene for which amplification is selectable. A variety of genes which provide selections for amplification have been described (Kaufman 1990) but murine dihydrofolate reductase (dhfr) is frequently employed. Amplification of this gene confers resistance to the folate analog methotrexate (MTX) and the level of resistance increases with dhfr gene copy number (Alt et al., 1978). Utility of MTX selection is enhanced by the availability of CHO cell lines that are deficient in dhfr (Urlaub and Chasin, 1980).

One skilled in the art can construct expression vectors for the IgG fusion proteins or multimeric cytokines/growth factors that incorporate the murine dhfr gene into the commercially available pcDNA3.1 expression vector (Invitrogen), which includes the neomycin phosphotransferase (NPT) gene that confers resistance to G418. The murine dhfr expression vector pdhfr2.9 is available from the American Type Culture Collection (catalogue No. 37165). This dhfr gene is selectable in dhfr$^-$ CHO cell lines and can be amplified by standard selections for MDC resistance (Crouse et al 1983). The dhfr coding sequence can be excised from pdhfr2.9 as a ~900 by Bell fragment and cloned into the unique Bam HI site of the polylinker of the expression vector pREP4 (Invitrogen). This construct will position the gene downstream of the strong RSV promoter, which is known to function in CHO cells (Trill et al, 1995) and upstream of a polyadenylation site derived from SV40. This dhfr expression cassette can then be excised from pREP4 as a Sal I fragment since Sal I sites closely flank the promoter and polyA addition site. Using oligonucleotide linkers this Sal I fragment can be cloned into the unique Bgl II site of pcDNA3.1, creating pcDNA3.1(+):: dhfr$^+$. DNA encoding the IgG fusion protein or multimeric cytokine/growth factor can subsequently be cloned into the polylinker region of this pcDNA3.1 (+) derivative under the control of the CMV promoter. For example, the EPO-IgG1-Fc or G-CSF-IgG1-Fc genes could be excised from plasmids pBBT180 and pBBT174, respectively as Hind III-Xba I fragments and cloned into Hind III-Xba I-cut pcDNA3.1(+):: dhfr$^+$. Other unique restriction enzyme sites can be used if these restriction enzyme sites are present in the genes of interest. Alternatively, co-transfection of pcDNA3.1(+):: dhfr$^+$ and pcDNA3.1 derivatives expressing the IgG fusion proteins or multimeric cytokines/growth factors could be employed to obtain dhfr$^+$ CHO cell lines expressing the protein of interest (Kaufmann, 1990).

Endotoxin free plasmid DNAs are preferred for transfecting mammalian cells such as COS or dhfr$^-$ CHO cells. Dhfr$^-$ CHO cell lines can be obtained from a number of sources such as Dr. L. Chasin at Columbia University (CHO K1 DUKX B11) or from the American Type Culture Collection (CHO duk$^-$, ATCC No. CRL-9096). The cells can be cultured in F12/DMEM medium supplemented with 10% FBS, glutamine, glycine, hypoxanthine, and thymidine (Lucas et al., 1996). Transfections can be carried out by electroporation or by using transfection reagents well known to those of skill in the art such as LipofectAMINE (Gibco BRL), using the vendor protocols and/or those described in the literature (Kaufman, 1990). One can select for dhfr$^+$ transfectants in F12/DMEM supplemented with 7% dialyzed FCS and lacking glutamine, glycine, hypoxanthine, and thymidine (Lucas et al., 1996). Alternatively one can select for G418 resistance (encoded by the NPT gene of pcDNA3.1) and subsequently screen transfectants for the dhfr$^+$ phenotype. Dhfr$^+$ clones can be expanded in selection medium and culture supernatants screened for expression of the IgG fusion proteins or multimeric cytokines/growth factors using commercially available ELISA kits specific for the growth factor or cytokine (available from R & D Systems, Endogen, Inc. and Diagnostic Systems Laboratories) or by Western blot using appropriate antisera (available from R&D Systems, Endogen, Inc. and Diagnostic Systems Laboratories). Clones expressing the IgG fusion proteins or multimeric cytokines/growth factors can then be pooled and subjected to multiple rounds of selection for MTX resistance at increasing drug concentration as described by Kaufman (1990). After each round of MTX selection, individual clones Can be tested for expression of the IgG fusion proteins or multimeric cytokines/growth factors. These procedures are well described in the literature and have been used to express a variety of heterologous protein in CHO cells (reviewed in Kaufmann, 1990).

The IgG fusion proteins can be purified from the conditioned medium of CHO cells. After removal of the CHO cells by centrifugation, the IgG fusion proteins can be purified from the supernatant by Protein A affinity column chromatography using protocols similar to those described in Example 2, followed by additional chromatography steps as needed. Dimeric IgG-Fc and IgG-$C_H$ fusions can be purified further by size-exclusion chromatography to remove monomers and aggregates. Additional column chromatography steps could include Blue Sepharose, hydroxyapatite, reversed phase, hydrophobic interaction, and ion-exchange chromatography. These techniques are well known to those of skill in the art.

Multimeric cytokines/growth factors and cytokine/growth factor-light chain constant region fusions also can be purified from the conditioned medium of CHO cells. After removal of the CHO cells by centrifugation, the multimeric cytokines/growth factors and cytokine/growth factor-light chain constant region fusions can be purified from the supernatant by column chromatography using techniques well known to those of skill in the art. These column chromatography steps could include Blue Sepharose, hydroxyapatite, reversed phase, hydrophobic interaction, size exclusion and ion-exchange chromatography. The proteins also can be purified by affinity chromatography using monoclonal antibodies specific for the cytokine/growth factor or light chain constant region.

REFERENCES

Aggarwal, B. B. (1998) Human Cytokines. Handbook for Basic and Clinical Research. Volume III. Blackwell Science, Malden, Mass.

Aggarwal, B. B. and Gutterman, J. U. (1992) Human Cytokines. Handbook for Basic and Clinical Research. Volume I. Blackwell Science, Malden, Mass.

Aggarwal, B. B. and Gutterman, J. U. (1996) Human Cytokines. Handbook for Basic and Clinical Research. Volume II. Blackwell Science, Malden, Mass.

Alt, F. W., Kellems, R. E., Bertino, J. R., and Schimke, R. T. (1978) J. Biol. Chem. 253:1357-1370.

Avanzi, G. C., Lista, P., Giovinazzo, B., Miniero, R., Saglio, G., Benetton, G., Coda, R., Cattoretti, G. and Pegorara, L. (1988) Br. J. Haematology 69: 359-356.

Baldwin, M. D., Thou, X. J., Ing, T. S. and Vaziri, N. D. (1998) ASAIO J. 44: 44-47.

Balkwill, F. R., Goldstein, L. and Stebbing, N. (1985) Int. J. Cancer 35: 613-617.

Balkwill, F. R. (1986) Methods Enzymology 119: 649-657.

Bartley, T. D., Bogenberger, J., Hunt, P., Li, Y.-S., et al. (1994) Cell 77: 1117-1124.

Bazan, F. (1990) Immunology Today 11: 350-354.

Bazan, J. F. (1991) Cell 65: 9-10.

Bazan, J. F. (1992) Science 257: 410-411.

Blatt, L. M., Davis, J. M., Klein, S. B. and Taylor, M. W. (1996) J. Interferon and Cytokine Research 16: 489-499.

Boissel, J.-P., Lee, W.-R., Presnell, S. R., Cohen, F. E. and Bunn, H. F. (1993). J. Biol. Chem. 268: 15983-15993.

Cantrell, M. A., Anderson, D. and Cerretti, D. P (1985) Proc. Natl. Acad. Sci. USA 82: 6250-6254.

Capon, D. J., Chamow, S. C., Mordenti, J., Marsters, S. A., Gregory, T., Mitsuya, H., Byrn, R. A., Lucas, C., Wurm, F. M., Groopman, J. E., Broder, S. and Smith, D. H. (1989) Nature 337: 525-531.

Chamow, S. M. and Ashkenazi, A. (1996) Trends in Biotech. 14: 52-60.

Chen, T. T., Ta, M.-H. and Levy, R. (1994) J. Immunology 153: 4775-4787.

Clark, R., Olson, K., Fuh, G., Marian, M., Mortensen, D., Teshima, G., Chang, S., Chu, H., Mukku, V., Canova-Davis, E., Somers, T., Cronin, M., Winkler, M. and Wells, J. A. (1996) J. Biol. Chem. 271: 21969-21977.

Cox, G. N. and McDermott, M. J. (1994) WO 9412219.

Cox, G. N., McDermott, M. J., Merkel, E., Stroh, C. A., Ko, S. C., Squires, C. H., Gleason, T. M. and Russell, D. (1994) Endocrinology 135: 1913-1920.

Crouse, G. F., McEwan, R. N., and Pearson, M. L. (1983) Mol. Cell. Biol. 3:257-266.

Dangl, J. L., Wensel, T. G., Morrison, S. L., Stryer, L., Herzenberg, L. A. and Oi, V. T. (1988) EMBO J. 7: 1989-1994.

DeNoto, F. M., Moore, D. D. and Goodman, H. M. (1981) Nucleic Acids Research 9: 3719-3730.

Derynnck, R., Content, J., DeClercq, E., Volckaert, G., Tavernier, J. DeVos, R. and Fiers, W. (1980) Nature 285: 542-547.

de Sauvage, F. J., Hass, P. E., Spencer, S. D., Malloy, B. E. et al. (1994) Nature 369: 589-596.

Dikov, M. M., Reich, M. B., Dworkin, L., Thomas, J. W., and Miller, G. G. (1998) J. Biol. Chem. 273: 15811-15817.

Donahue, R. E., Wang E. A., Stone, D. K., Kamen, R., Wong, G. G., Sehgal, P. K., Nathan, D. G. and Clark, S. C. (1986a) Nature 321:872-5

Donahue, R. E., Wang, E. A., Kaufaman, R. J., Foutch, L., Leary, A. C. and Witek-Giannetti, J. S. (1986b) Cold Spring Harbor Symp. Quant. Biol. 51: 685-692.

Elliot, S. G. and Byrne, T. E. (1995) European Patent Application #94112732.6

Ellison, J., Buxbaum, J. and Hood, L. (1991) DNA 1: 11-18.

Ellison, J. W., Berson, B. J. and Hood, L. E. (1982) Nucleic Acids Research 10: 4071-4079.

Evinger, M. and Pestka, S. (1981) Methods Enzymology 79: 362-368.

Foster, D. C., Sprecher, C. A., Grant, F. J., Kramer, J. M et al. (1994) Proc. Natl. Acad. Sci. USA 91: 13023-13027.

Gamba-Vitalo, C., DiGiovanna, M. P., and Sartorelli, A. C. (1991) Blood Cells 17:193-205.

Geisse, S., Gram, H., Kleuser, B. and Kocher, H. P. (1996) Prot. Express. Purif. 8:271-282.

Gillies, S. D., Young, D., Lo, K.-M. and Roberts, S. (1993) Bioconjugate Chem. 4: 230-235.

Gray, P. W., Leung, D. W., Pennica, D., Yelverton, E., Najarian, R., Simonsen, C. C., Derynxk, R., Sherwood, P. J., Wallace, D. M., Berger, S. I., Levinson, A. D. and Goeddel, D. V. (1982) Nature 295: 503-508.

Greenspan, F. S., Li., C. H., Simpson, M. E. and Evans, H. M. (1949) Endocrinology 45:455-463.

Gough, N. M., Metcalf, D., Gough, J., Grail, D. and Dunn, A. R. (1985) EMBO J. 4: 645-53.

Gough, N. M., Gough, J., Metcalf, D., Kelso, A., Grail, D., Nicola, N. A., Burgess, A. W. and Dunn, A. R. (1984) Nature 309:763-7.

Hangcoc, G., Yin, T., Cooper, S., Schendel, P., Yang, Y.-C. and Broxmeyer, H. E. (1993) Blood 81: 965-972.

Hannum, C., Culpepper, J., Campbell, D., McClanahan, T., Zurawski, S. et al. (1994) Nature 368: 643-648

Hanzazono, Y., Hosoi, T., Kuwaki, T., Matsuki, S., Miyazono, K., Miyagawa, K., and Takaku, F. (1990) Exp. Hematol. 18: 1097-1103.

Henco, K., Brosius, J., Fujisawa, A., Fujisawa, Haynes, J. R., Hochstadt, J., Kovacic, T., Pasek, M., Schambock, A., Schmid, J., Todokoro, K., Walchli, M., Nagata, S. and Weissman, C. (1985) J. Mol. Biol. 185: 227-260.

Hieter, P. Max, E. Seidman, J. Maizel, J and Leder, P. (1980) Cell 22: 197-207.

Horisberger, M. A. and Di Marco, S. (1995) Pharmac. Ther. 66: 507-534.

Horoszewicz, J. S., Leong, S. S. and Carter, W. A. (1979) Science 206: 1091-1093.

Horton, R. M. (1993) in "Methods in Molecular Biology", White, B. A., ed. (Humana Press, Totawa, N.J.) 15:214-250.

Innis, M. A., Gelfand, D. H, Sninsky, J. J. and White, T. J. eds. (1990) "PCR Protocols: A Guide to Methods and Applications" (Academic Press, San Diego, Calif.).

Isaacs, J. D., Greenwood, J. and Waldmann, H. (1998) J. Immunol. 161:3862-3869.

Johns, T. G., Mackay, I. R., Canister, K. A., Hartzog, P. J., Devenish, R. J. and Linnane, A. W. (1992) J. Natl. Cancer Institute 84: 1185-1190.

Kajigaya, S., Suda, T., Suda, J., Saito, M., Miura, Y., Iizuka, M., Kobayashi, S., Minato, N. and Sudo, T. (1986) J Exp Med 164:1102-13.

Kang, S.-H., Na, K.-H., Park, J.-H., Park, C.-I., Lee, S.-Y. and Lee, Y.-I. (1995) Biotechnology Letters 17: 687-692.

Kaufman, R. J. (1990) Meth. Enzymol. 185:537-566.

Kasbzubska, W., Zhang, H., Patterson, R. L., Suhar, T. S. et al., (2000) Protein Expression and Purification 18: 213-220.

Kaushansky, K., Lok, S., Holly, R. D. et al., (1994) Nature 369: 568-571.

Knauf, M. J., Bell, D. P., Hirtzer, P., Luo, Z.-P., Young, J. D., and Katres, N. V. (1988) J. Biol. Chem. 263:15064-15070.

Kozak, M. (1991) J. Biol. Chem. 266: 19867-19870.

Kubota, N., Orita, T., Hattori, K., Oh-eda, M., Ochi, N. and Yamazaki, T. (1990) J. Biochem. 107: 486-492.

Kuga, T., Komatsu, Y., Yamazaki, M., De4kine, S., Miyaji, H., Nishi, T., Sato, M., Yokoo, Y., Asano, M., Okabe, M., Morimoto, M. and Itoh, S. (1989) Bioch. Biophys. Res. Comm. 159: 103-111.

Landolphi, N. F. (1991) J. immunology 146: 915-919.

Landolfi, N. F. (1994) U.S. Pat. No. 5,349,053.

LaRochelle, W. J., Dirsch, O. R., Finch, P. W., Cheon, H.-G., May, M., Marchese, C., Pierce, J. H. and Aaronson, S. A. (1995) J. Cell Biol. 129: 357-366.

Leonard, J. P., Quinto, C. M., Kozitza, M. K., Neben, T. Y. and Goldman, S. J. (1994) Blood 83: 1499-1506.

Lewis, J. A. (1987) Chapter 6. Lymphokines and Interferons: A Practical approach. Eds: Clemens, M. J., Morris, A. G. and Gearing, A. J. H., IRL Press Ltd., Oxford, England.

Lewis, J. A. (1995) Chapter 9: Antiviral activity of cytokines. pp. 129-141.

Lin, F.-K., Suggs, S., Lin, C.-H., Browne, J. K., Smalling, R., Egrie, J. C., Chen, K. K., Fox, G. M., Martin, F., Stabinsky, Z., Badrawi, S. M., Lai, P.-H. and Goldwasser, E. (1985) Proc. Natl. Acad. Sci. USA 82: 7580-7584.

Lindner, D. J. and Borden, E. C. (1997) J. Interferon and Cytokine Research 17:681-693.

Linsley, P. S., Brady, W., Grosmaire, L., Aruffo, A., Damle, N. K. and Ledbetter, J. A. (1991a) J. Exp. Med. 173: 721-730.

Linsley, P. S., Brady, W., Umes, M., Grosmaire, L. S., Damle, N. K. and Ledbetter, J. A. (1991b) J. Exp. Med. 174:561-569.

Lok, S., Kaushansky, K., Holly, R. D., et al. (1994) Nature 369: 565-568.

Lu, H. S., Clogston, C. L., Narhi, L. O., Merewether, L. A., Pearl, W. R. and Boone, T. C. (1992) J. Biol. Chem. 267: 8770-8777.

Lu, Z.-Y., zhang, X.-G., Gu, Z.-J., Yazukawa, K., Amiot, M., Etrillard, M., Bataille, R. and Klein, B. (1994) J. Immunol. Methods 173:19026.

Lucas, B. K., Giere, L. M., DeMarco, M. A., Shen, A., Chisolm, V., and Crowley, C. W. (1996) Nucleic Acids Res. 24:1774-1779.

Lyman, S. D., James, L., Vanden Bos, T., de Vries, P. et al. (1993) Cell 1157-1167.

Mahmood, I. (1998) Life Sciences 63:2365-2371.

Mark, D. F., Lu, S. D., Creasey, A. A., Yamamoto, R. and Lin, L. S. (1984) Proc. Natl. Acad. Sci. 81: 5662-5666.

Martial, J. A., Hallewell, R. A., Baxter, J. D. and Goodman, H. M. (1979) Science 205: 602-607.

Martin, F. H., Suggs, S. V., Langley, K. E., Lu, H. S., Ting, J., Okino, K. H., Morris, F. C., McNiece, I. K., Jacobsen, F. W., Mendiaz, E. A., Birkett, N. C. et al., (1990) Cell 63: 203-211.

Matsumoto, T., Endoh, K., Kamisango, K., Akamatsu, K., Koizumi, K., Higuchi, M., Imai, N., Misui, H. and Kawaguchi, T. (1990) Br. J. Haematol. 75: 463-468.

Mayer, P., Lam, C., Obenaus, H., Liehl, E., and Besemer, J. (1987a) Ann N Y Acad Sci 511:17-29.

Mayer, P., Lam, C., Obenaus, H., Liehl, E., and Besemer, J. (1987b) Blood 70:206-13.

Mayer, P., Schutz, E., Lam, C., Kricek, F., and Liehl, E. (1991) J.-Infect. Dis. 163:584-590.

Mayer, P., Werner, F., Lam, C., and Besemer, J. (1990) Exp. Hematol. 18:1026-1033.

McKinley, D., Wu, Q., Yang-Feng, T. and Yang, Y.-C. (1992) Genomics 13: 814-819.

Mohler, K. M., Torrance, D. S., Smith, C. A., Goodwin, R. G., Stremler, K. E., Fung, V. P., Madani, H. and Widmer, M. B. (1993) J. Immunology 151: 1548-1561.

Morenti, J., Chen, S. A. Moore, J. A., Frerraiolo, B. L. and Green J. D. (1991) Pharm Res. 8:1351-1359.

Morton, P. A., Fu., X.-T., Stewart, J. A., Giacoletto, K. S., White, S. L., Leysath, S. E., Evans, R. J., Shieh, J.-J. and Karr, R. W. (1996) J. Immunology 156: 1047-1054.

Mott, H. R. and Campbell, I. D. (1995) Current Opinion in Structural Biology 5: 114-121.

Nagata, S. (1994) in Cytokines and Their Receptors, N.A. Nicola ed., Oxford University Press, Oxford, pp. 158-160.

Nagata, S., Tsuchiya, M., Asano, S., Kziro, Y., Yamazaki, T., Yamamoto, O., Hirata, Y., Kubota, N., Oh-eda, M., Nomura, H. and Ono, M. (1986a) Nature 319: 415-418.

Nagata, S., Tsuchiya, M., Asano, S., Yamamoto, O., Hirata, Y., Kubota, N., Oh-eda, M., Nomura, H. and Yamazaki, T. (1986b) EMBO J. 5: 575-581.

Neben, T. Y., Loebelenz, J., Hayes, L., McCarthy, K., Stoudmire, J., Schaub, R. and Goldman, S. J. (1993) Blood 81:901-908.

Oi, V. T., Vuong, T. M., Hardy, R., Reidler, J., Dangl, J., Herzenberg, L. A. and Stryer, L. (1984) Nature 307: 136-140.

Okabe, M., Asano, M., Kuga, T., Komatsu, Y., Yamazaki, M., Yokoo, Y., Itoh, S., Morimoto, M and Oka, T. (1990) Blood 75: 1788-1793.

Ozes, O. S., Reiter, Z., Klein, S., Blatt, L. M. and Taylor, M. W. (1992) J. Interferon Research 12: 55-59.

Qiu, H., Belanger, A., Yoon, H.-W. P. and Bunn, H. F. (1998) J. Biol. Chem. 273: 11179-11176.

Richter, W. F., Gallati, H., Schiller, C. (1999) Drug Metabolism and Disposition 27: 21-25

Roitt, I., Brostoff, J. and Male, D. eds. (1989) "Immunology" (Gower Medical Publishing, London, U.K.; New York, N.Y.)

Roskam, W. G. and Rougeon, F. (1979) Nucleic Acids Research 7:305-320.

Rowlinson, S. W. Barnard, R., Bastiras, S., Robins, A. J., Brinkworth, R. and Waters, M. J. (1995) J. Biol. Chem. 270: 16833-16839.

Schuening, F. G., Storb, R., Goehle, S., Nash, K., Graham, T. C., Appelbaum, F. R., Hackman, R., Sandmaier, B. M., and Urdal, D. L. (1989) Exp. Hematol. 17:889-894.

Seeburg, P. H. (1982) DNA 1: 239-249.

Shin, S.-U., and Morrison, S. L. (1990) Proc. Natl. Acad. Sci. USA 87: 5322-5326.

Silvennoinen, O. and Ihle, J. N. (1996) Signalling by Hematopoietic Cytokine Receptors, R.G. Landes Company, Austin, Tex.

Sohma, Y., Akahori, H., Seki, N., Hori, T., Ogami, K., Kato, T., Shimada, Y., Kawamura, K. and Miyaki, H. (1994) FEBS Letters 353: 57-61.

Souza, L. M., Boone, T. C., Gabrilove, J., Lai, P. H., Zsebo, K. M., Murdock, D. C., Chazin, Bruszewski, J., Lu, H., Chen, K. K., Barendt, J., Platzer, E., Moore, M. A. S., Mertelsmann, R. and Welte, K. (1986) Science 232: 61-65.

Stewart, J. D., Lee, I., Posner, B. A. and Benkovic, S. J. (1995) Meth. Enzymol. 249:507-519.

Steurer, W., Nickerson, P. W., Steele, A. W., Steiger, J, Meng, X. X. and Strom, T. B. (1995) J. Immunology 155: 1165-1174.
Sytkowski, A. J., Lunn, E. D. Davis, K. L. Feldman, L. and Siekman, S. (1998) PNAS 95:1184-1188.
Trill, J. J., Shatzman, A. R., and Ganguly, S. (1995) Curr. Opin. Biotechnol. 6:553-560.
Urlaub, G. and Chazin, L. A. (1980) Proc. Natl. Acad. Sci. USA 77:4216-4220.
Vaziri, N. D., Zhou, X. J., and Liao, S. Y. (1994) Am. J. Physiol. 266: F360-366.
Wang, G. L. and Semenza, G. L. (1993) Blood: 82: 3610-3615.
Weinstein, Y., Ihle, J. N., Laws, S. and Reddy, E. P. (1986) PNAS 83: 5010-5014.
Weiss, A., Wiskocil, R. L. and Stobo, J. D. (1984) J. Immunology 133: 123-128.
Wisckocil, R., Weiss, A., Imboden, J., Kamin-Lewis, R. a. and Stobo, J. (1985) J. Immunology 134: 1599-1603.
Yonemura, Y., Kawakita, M., Masuda, T., Fujimoto, K., and Talcatsuki, K. (1993) Br. J. Haematol 84: 16-23.
Zeng, X. X., Steele, A. W., Nickerson, P. W., Steurer, W., Steiger, J. and Strom, T. B. (1995) J. Immunology 154: 5590-5600.
Kitamura, T., Tange, T., Terasawa, T., Chiba, S., Kuwaki, T., Miyagawa, K., Piao, Y. F., Miyazono, K., Urabe, A. and Takaku, F. (1989) J. Cell. Physiol. 140:323-334.

While various embodiments of the present invention have been described in detail, it is apparent that modifications and adaptations of those embodiments will occur to those skilled in the art. It is to be expressly understood, however, that such modifications and adaptations are within the scope of the present invention.

The invention claimed is:

1. A fusion protein comprising a full-length human erythropoietin protein joined without an intervening peptide linker to a human immunoglobulin (Ig) domain that does not contain a variable region wherein the Ig domain is selected from the group consisting of full-length IgG-Fc, IgG-$C_H$ and IgG-$C_L$, wherein the fusion protein consists of the natural human erythropoietin amino acid sequence and the natural human immunoglobulin domain amino acid sequence at the junction of the fusion protein.

2. The fusion protein of claim 1, wherein said fusion protein has an $EC_{50}$ of less than 4 ng/ml in an EPO-dependent in vitro bioassay using a human UT7/epo cell line that proliferates in response to EPO.

3. The fusion protein of claim 1, wherein said fusion protein has an $EC_{50}$ within 4 fold of the $EC_{50}$ of non-fused EPO, on a molar basis, in an EPO-dependent in vitro bioassay using a human UT7/epo cell line that proliferates in response to EPO.

4. A pharmaceutical composition comprising the fusion protein of claim 1 in a pharmaceutically acceptable carrier.

5. A composition comprising the fusion protein of claim 1, wherein said fusion protein is dimeric and wherein said composition is essentially free of monomeric fusion protein.

6. A nucleic acid encoding the fusion protein of claim 1.

7. An isolated host cell transfected or transformed with the nucleic acid of claim 6, enabling the host cell to express the fusion protein.

8. The isolated host cell of claim 7, wherein the host cell is a eukaryotic cell.

9. The isolated host cell of claim 8, wherein the eukaryotic cell is a mammalian cell.

10. A method of producing a fusion protein of claim 1, comprising:
   a) transfecting or transforming an isolated host cell with an expression vector comprising a nucleic acid encoding the fusion protein of claim 1;
   b) culturing the host cell under conditions effective to express said fusion protein; and
   c) harvesting the fusion protein expressed by the host cell.

11. A method of purifying the fusion protein of claim 1, comprising:
   a) obtaining a composition comprising the fusion protein; and
   b) isolating the fusion protein from contaminants by column chromatography.

12. The method of claim 11, wherein the fusion protein is isolated from contaminants by size-exclusion chromatography.

13. A fusion protein comprising a full-length human erythropoietin protein joined without an intervening peptide linker to a human immunoglobulin (Ig) domain that does not contain a variable region wherein the Ig domain is selected from the group consisting of full-length IgG-Fc, IgG-$C_H$ and IgG-$C_L$, wherein the fusion protein consists of the natural human erythropoietin amino acid sequence and the natural human immunoglobulin domain amino acid sequence at the junction of the fusion protein, and wherein the fusion protein has an $EC_{50}$ of less than about 10 ng/ml in an EPO-dependent in vitro bioassay using a human UT7/epo cell line that proliferates in response to EPO.

14. A fusion protein comprising a full-length human erythropoietin protein joined without an intervening peptide linker to a human immunoglobulin (Ig) domain that does not contain a variable region wherein the Ig domain is selected from the group consisting of full-length IgG-Fc, IgG-$C_H$ and IgG-$C_L$, wherein the fusion protein consists of the natural human erythropoietin amino acid sequence and the natural human immunoglobulin domain amino acid sequence at the junction of the fusion protein, and wherein the fusion protein has an $EC_{50}$ of less than about 1000 ng/ml in an EPO-dependent in vitro bioassay using a human UT7/epo cell line that proliferates in response to EPO.

15. A method of treating a condition of a deficient hematocrit, comprising administering an effective amount of the fusion protein of claim 1, wherein administration of the fusion protein increases the hematocrit of the patient.

* * * * *

SEQUENCE LISTING

```
<160> NUMBER OF SEQ ID NOS: 87

<210> SEQ ID NO 1
<211> LENGTH: 4
<212> TYPE: PRT
<213> ORGANISM: Artificial sequence
<220> FEATURE:
<221> NAME/KEY: PEPTIDE
<222> LOCATION: (1)..(4)
<223> OTHER INFORMATION: linker

<400> SEQUENCE: 1

Ser Gly Gly Ser
1

<210> SEQ ID NO 2
<211> LENGTH: 5
<212> TYPE: PRT
<213> ORGANISM: Artificial sequence
<220> FEATURE:
<221> NAME/KEY: PEPTIDE
<222> LOCATION: (1)..(5)
<223> OTHER INFORMATION: linker

<400> SEQUENCE: 2

Gly Ser Gly Gly Ser
1               5

<210> SEQ ID NO 3
<211> LENGTH: 7
<212> TYPE: PRT
<213> ORGANISM: Artificial sequence
<220> FEATURE:
<221> NAME/KEY: PEPTIDE
<222> LOCATION: (1)..(7)
<223> OTHER INFORMATION: linker

<400> SEQUENCE: 3

Ser Gly Gly Ser Gly Gly Ser
1               5

<210> SEQ ID NO 4
<211> LENGTH: 35
<212> TYPE: DNA
<213> ORGANISM: Artificial sequence
<220> FEATURE:
<221> NAME/KEY: misc_feature
<222> LOCATION: (1)..(35)
```

<223> OTHER INFORMATION: primer

<400> SEQUENCE: 4
gcaagcttgc caccatggct acaggctccc ggacg                        35

<210> SEQ ID NO 5
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 5
cgcggatcct ccggagaagc cacagctgcc ctccac                       36

<210> SEQ ID NO 6
<211> LENGTH: 31
<212> TYPE: DNA
<213> ORGANISM: Artificial sequence
<220> FEATURE:
<221> NAME/KEY: misc_feature
<222> LOCATION: (1)..(31)
<223> OTHER INFORMATION: primer

<400> SEQUENCE: 6
cccggatcca tgggggtgca cgaatgtcct g                            31

<210> SEQ ID NO 7
<211> LENGTH: 31
<212> TYPE: DNA
<213> ORGANISM: Artificial sequence
<220> FEATURE:
<221> NAME/KEY: misc_feature
<222> LOCATION: (1)..(31)
<223> OTHER INFORMATION: primer

<400> SEQUENCE: 7
cccgaattct atgcccaggt ggacacacct g                            31

<210> SEQ ID NO 8
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 8
cgcaagcttg ccaccatggg ggtgcacgaa tgtcct                       36

<210> SEQ ID NO 9
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 9
cgcggatcct ccggatctgt ccctgtcct gcaggc                        36

<210> SEQ ID NO 10
<211> LENGTH: 39

```
<212> TYPE: DNA
<213> ORGANISM: Artificial sequence
<220> FEATURE:
<221> NAME/KEY: misc_feature
<222> LOCATION: (1)..(39)
<223> OTHER INFORMATION: primer

<400> SEQUENCE: 10
cgcggatcct ccggatctgt ccctgtcct gcaggcctc                              39

<210> SEQ ID NO 11
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 11
cgcaagcttg ccaccatggc tggacctgcc acccag                                36

<210> SEQ ID NO 12
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 12
cgcggatcct ccggagggct gggcaaggtg gcgtag                                36

<210> SEQ ID NO 13
<211> LENGTH: 42
<212> TYPE: DNA
<213> ORGANISM: Artificial sequence
<220> FEATURE:
<221> NAME/KEY: misc_feature
<222> LOCATION: (1)..(42)
<223> OTHER INFORMATION: primer

<400> SEQUENCE: 13
cgcggatccg gtggctcaga gcccaaatct tgtgacaaaa ct                         42

<210> SEQ ID NO 14
<211> LENGTH: 30
<212> TYPE: DNA
<213> ORGANISM: Artificial sequence
<220> FEATURE:
<221> NAME/KEY: misc_feature
<222> LOCATION: (1)..(30)
<223> OTHER INFORMATION: primer

<400> SEQUENCE: 14
cgctctagag gtacgtgcca agcatcctcg                                       30

<210> SEQ ID NO 15
<211> LENGTH: 42
<212> TYPE: DNA
<213> ORGANISM: Artificial sequence
<220> FEATURE:
<221> NAME/KEY: misc_feature
<222> LOCATION: (1)..(42)
<223> OTHER INFORMATION: primer

<400> SEQUENCE: 15
```

-continued cgcggatccg gtggctcaga gtccaaatat ggtcccccat gc    42

<210> SEQ ID NO 16
<211> LENGTH: 38
<212> TYPE: DNA
<213> ORGANISM: Artificial sequence
<220> FEATURE:
<221> NAME/KEY: misc_feature
<222> LOCATION: (1)..(38)
<223> OTHER INFORMATION: primer

<400> SEQUENCE: 16
cgcggatccg gtggctcagc ctccaccaag ggcccatc    38

<210> SEQ ID NO 17
<211> LENGTH: 66
<212> TYPE: DNA
<213> ORGANISM: Artificial sequence
<220> FEATURE:
<221> NAME/KEY: misc_feature
<222> LOCATION: (1)..(66)
<223> OTHER INFORMATION: primer

<400> SEQUENCE: 17
tccaccaagg gcccatccgt cttccccctg gcgccctgct ccaggagcac ctccgagagc    60
acagcc    66

<210> SEQ ID NO 18
<211> LENGTH: 66
<212> TYPE: DNA
<213> ORGANISM: Artificial sequence
<220> FEATURE:
<221> NAME/KEY: misc_feature
<222> LOCATION: (1)..(66)
<223> OTHER INFORMATION: primer

<400> SEQUENCE: 18
tctcttgtcc accttggtgt tgctgggctt gtgatctacg ttgcaggtgt aggtcttcgt    60
gcccaa    66

<210> SEQ ID NO 19
<211> LENGTH: 39
<212> TYPE: DNA
<213> ORGANISM: Artificial sequence
<220> FEATURE:
<221> NAME/KEY: misc_feature
<222> LOCATION: (1)..(39)
<223> OTHER INFORMATION: primer

<400> SEQUENCE: 19
tgggggacca tatttggact caactctctt gtccacctt    39

<210> SEQ ID NO 20
<211> LENGTH: 27
<212> TYPE: DNA
<213> ORGANISM: Artificial sequence
<220> FEATURE:
<221> NAME/KEY: misc_feature
<222> LOCATION: (1)..(27)
<223> OTHER INFORMATION: primer

<400> SEQUENCE: 20
ttcctgctca agtccttaga gcaagtg    27

<210> SEQ ID NO 21
<211> LENGTH: 27

```
<212> TYPE: DNA
<213> ORGANISM: Artificial sequence
<220> FEATURE:
<221> NAME/KEY: misc_feature
<222> LOCATION: (1)..(27)
<223> OTHER INFORMATION: primer

<400> SEQUENCE: 21
cacttgctct aaggacttga gcaggaa                                              27

<210> SEQ ID NO 22
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 22
aggacagggg acagagagcc caaatcttgt gacaaa                                    36

<210> SEQ ID NO 23
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 23
acaagatttg ggctctctgt cccctgtcct gcaggc                                    36

<210> SEQ ID NO 24
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 24
aggacagggg acagagagtc caaatatggt cccca                                     36

<210> SEQ ID NO 25
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 25
accatatttg gactctctgt ccctgtcct gcaggc                                     36

<210> SEQ ID NO 26
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 26
```
tgcaggacag gggacgagcc caaatcttgt gacaaa                    36

<210> SEQ ID NO 27
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 27
acaagatttg ggctcgtccc ctgtcctgca ggcctc                    36

<210> SEQ ID NO 28
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 28
tgcaggacag gggacgagtc caaatatggt cccccca                   36

<210> SEQ ID NO 29
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 29
accatatttg gactcgtccc ctgtcctgca ggcctc                    36

<210> SEQ ID NO 30
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 30
caccttgccc agcccgagcc caaatcttgt gacaaa                    36

<210> SEQ ID NO 31
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 31
acaagatttg ggctcgggct gggcaaggtg gcgtag                    36

<210> SEQ ID NO 32
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 32
caccttgccc agcccgagtc caaatatggt ccccca          36

<210> SEQ ID NO 33
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 33
accatatttg gactcgggct gggcaaggtg gcgtag          36

<210> SEQ ID NO 34
<211> LENGTH: 34
<212> TYPE: DNA
<213> ORGANISM: Artificial sequence
<220> FEATURE:
<221> NAME/KEY: misc_feature
<222> LOCATION: (1)..(34)
<223> OTHER INFORMATION: primer

<400> SEQUENCE: 34
cgcgaattcc ggagagccca atcttgtga caaa          34

<210> SEQ ID NO 35
<211> LENGTH: 30
<212> TYPE: DNA
<213> ORGANISM: Artificial sequence
<220> FEATURE:
<221> NAME/KEY: misc_feature
<222> LOCATION: (1)..(30)
<223> OTHER INFORMATION: primer

<400> SEQUENCE: 35
cgcggatccg agcccaaatc ttgtgacaaa          30

<210> SEQ ID NO 36
<211> LENGTH: 34
<212> TYPE: DNA
<213> ORGANISM: Artificial sequence
<220> FEATURE:
<221> NAME/KEY: misc_feature
<222> LOCATION: (1)..(34)
<223> OTHER INFORMATION: primer

<400> SEQUENCE: 36
cgcgaattcc ggagagtcca aatatggtcc ccca          34

<210> SEQ ID NO 37
<211> LENGTH: 30
<212> TYPE: DNA
<213> ORGANISM: Artificial sequence
<220> FEATURE:
<221> NAME/KEY: misc_feature
<222> LOCATION: (1)..(30)
<223> OTHER INFORMATION: primer

<400> SEQUENCE: 37
cgcggatccg agtccaaata tggtccccca          30

<210> SEQ ID NO 38

```
<211> LENGTH: 63
<212> TYPE: DNA
<213> ORGANISM: Artificial sequence
<220> FEATURE:
<221> NAME/KEY: misc_feature
<222> LOCATION: (1)..(63)
<223> OTHER INFORMATION: primer

<400> SEQUENCE: 38
gcttttggcc tgctctgcct gccctggctt caagagggca gtgccactgt ggctgcacca    60
tct                                                                  63

<210> SEQ ID NO 39
<211> LENGTH: 30
<212> TYPE: DNA
<213> ORGANISM: Artificial sequence
<220> FEATURE:
<221> NAME/KEY: misc_feature
<222> LOCATION: (1)..(30)
<223> OTHER INFORMATION: primer

<400> SEQUENCE: 39
cgctctagac taaacactctc ccctgttgaa                                    30

<210> SEQ ID NO 40
<211> LENGTH: 66
<212> TYPE: DNA
<213> ORGANISM: Artificial sequence
<220> FEATURE:
<221> NAME/KEY: misc_feature
<222> LOCATION: (1)..(66)
<223> OTHER INFORMATION: primer

<400> SEQUENCE: 40
cgcaagcttg ccaccatggc tacaggctcc cggacgtccc tgctcctggc ttttggcctg    60
ctctgc                                                               66

<210> SEQ ID NO 41
<211> LENGTH: 38
<212> TYPE: DNA
<213> ORGANISM: Artificial sequence
<220> FEATURE:
<221> NAME/KEY: misc_feature
<222> LOCATION: (1)..(38)
<223> OTHER INFORMATION: primer

<400> SEQUENCE: 41
cgcggatccg gtggctcaac tgtggctgca ccatctgt                            38

<210> SEQ ID NO 42
<211> LENGTH: 30
<212> TYPE: DNA
<213> ORGANISM: Artificial sequence
<220> FEATURE:
<221> NAME/KEY: misc_feature
<222> LOCATION: (1)..(30)
<223> OTHER INFORMATION: primer

<400> SEQUENCE: 42
cgctctagac taaacactctc ccctgttgaa                                    30

<210> SEQ ID NO 43
<211> LENGTH: 15
<212> TYPE: PRT
<213> ORGANISM: Artificial sequence
<220> FEATURE:
<221> NAME/KEY: PEPTIDE
```

```
<222> LOCATION: (1)..(15)
<223> OTHER INFORMATION: linker

<400> SEQUENCE: 43

Ser Gly Gly Ser Gly Gly Ser Asp Tyr Lys Asp Asp Asp Asp Lys
1               5                   10                  15

<210> SEQ ID NO 44
<211> LENGTH: 33
<212> TYPE: DNA
<213> ORGANISM: Artificial sequence
<220> FEATURE:
<221> NAME/KEY: misc_feature
<222> LOCATION: (1)..(33)
<223> OTHER INFORMATION: primer

<400> SEQUENCE: 44
cgcgaattcg gatatgtaaa tagatacaca gtg                              33

<210> SEQ ID NO 45
<211> LENGTH: 33
<212> TYPE: DNA
<213> ORGANISM: Artificial sequence
<220> FEATURE:
<221> NAME/KEY: misc_feature
<222> LOCATION: (1)..(33)
<223> OTHER INFORMATION: primer

<400> SEQUENCE: 45
cgcaagctta aaagatttaa atcgtgtcat ggt                              33

<210> SEQ ID NO 46
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 46
cgcaagcttg ccaccatggc cttgaccttt gcttta                           36

<210> SEQ ID NO 47
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 47
cgcggatcct ccggattcct tacttcttaa actttc                           36

<210> SEQ ID NO 48
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 48
cgcaagcttg ccaccatgac caacaagtgt ctcctc                           36
```

```
<210> SEQ ID NO 49
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 49
cgcggatcct ccggagtttc ggaggtaacc tgtaag                              36

<210> SEQ ID NO 50
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 50
cgcaagcttg ccaccatgaa atatacaagt tatatc                              36

<210> SEQ ID NO 51
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 51
cgcggatcct ccggactggg atgctcttcg accttg                              36

<210> SEQ ID NO 52
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 52
cgcaagcttg ccaccatgaa ctgtgtttgc cgcctg                              36

<210> SEQ ID NO 53
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 53
cgcggatcct ccggacagcc gagtcttcag cagcag                              36

<210> SEQ ID NO 54
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer
```

<400> SEQUENCE: 54
cgcaagcttg ccaccatgaa ctgtgtttgc cgcctg                              36

<210> SEQ ID NO 55
<211> LENGTH: 30
<212> TYPE: DNA
<213> ORGANISM: Artificial sequence
<220> FEATURE:
<221> NAME/KEY: misc_feature
<222> LOCATION: (1)..(30)
<223> OTHER INFORMATION: primer

<400> SEQUENCE: 55
gcgggacatc aggagctgca gccggcgcag                                     30

<210> SEQ ID NO 56
<211> LENGTH: 27
<212> TYPE: DNA
<213> ORGANISM: Artificial sequence
<220> FEATURE:
<221> NAME/KEY: misc_feature
<222> LOCATION: (1)..(27)
<223> OTHER INFORMATION: primer

<400> SEQUENCE: 56
cagctcctga tgtcccgcct ggccctg                                        27

<210> SEQ ID NO 57
<211> LENGTH: 27
<212> TYPE: DNA
<213> ORGANISM: Artificial sequence
<220> FEATURE:
<221> NAME/KEY: misc_feature
<222> LOCATION: (1)..(27)
<223> OTHER INFORMATION: primer

<400> SEQUENCE: 57
agtcttcagc agcagcagtc ccctcac                                        27

<210> SEQ ID NO 58
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 58
cgcggatcct ccggacagcc gagtcttcag cagcag                              36

<210> SEQ ID NO 59
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 59
ctgaagactc ggctggagcc caaatcttgt gacaaa                              36

<210> SEQ ID NO 60
<211> LENGTH: 36
<212> TYPE: DNA
<213> ORGANISM: Artificial sequence

```
<220> FEATURE:
<221> NAME/KEY: misc_feature
<222> LOCATION: (1)..(36)
<223> OTHER INFORMATION: primer

<400> SEQUENCE: 60
acaagatttg ggctccagcc gagtcttcag cagcag                              36

<210> SEQ ID NO 61
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 61
ctgaagactc ggctggagtc caaatatggt cccccA                              36

<210> SEQ ID NO 62
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 62
accatatttg gactccagcc gagtcttcag cagcag                              36

<210> SEQ ID NO 63
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 63
cgcaagcttg ccaccatgga gctgactgaa ttgctc                              36

<210> SEQ ID NO 64
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 64
cgcggatcct ccggaccctt cctgagacag attctg                              36

<210> SEQ ID NO 65
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 65
cgcggatcct ccggacctga cgcagagggt ggaccc                              36
```

```
<210> SEQ ID NO 66
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 66
ctgtctcagg aagggagcc caaatcttgt gacaaa                           36

<210> SEQ ID NO 67
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 67
acaagatttg ggctccccctt cctgagacag attctg                         36

<210> SEQ ID NO 68
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 68
ctgtctcagg aagggagtc caaatatggt ccccca                           36

<210> SEQ ID NO 69
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 69
accatatttg gactccccctt cctgagacag attctg                         36

<210> SEQ ID NO 70
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 70
cgcaagcttg ccaccatgtg gctgcagagc ctgctg                          36

<210> SEQ ID NO 71
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer
```

<400> SEQUENCE: 71
cgcggatcct ccggactcct ggactggctc ccagca                                    36

<210> SEQ ID NO 72
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 72
gagccagtcc aggaggagcc caaatcttgt gacaaa                                    36

<210> SEQ ID NO 73
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 73
acaagatttg ggctcctcct ggactggctc ccagca                                    36

<210> SEQ ID NO 74
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 74
gagccagtcc aggaggagtc caaatatggt cccccca                                   36

<210> SEQ ID NO 75
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 75
accatatttg gactcctcct ggactggctc ccagca                                    36

<210> SEQ ID NO 76
<211> LENGTH: 33
<212> TYPE: DNA
<213> ORGANISM: Artificial sequence
<220> FEATURE:
<221> NAME/KEY: misc_feature
<222> LOCATION: (1)..(33)
<223> OTHER INFORMATION: primer

<400> SEQUENCE: 76
cgcaagcttg ccaccatgaa gaagacacaa act                                       33

<210> SEQ ID NO 77
<211> LENGTH: 36
<212> TYPE: DNA

```
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 77
cgcggatcct ccggagtgta ggctggagtc tccagg                              36

<210> SEQ ID NO 78
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 78
gactccagcc tacacgagcc caaatcttgt gacaaa                              36

<210> SEQ ID NO 79
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 79
acaagatttg ggctcgtgta ggctggagtc tccagg                              36

<210> SEQ ID NO 80
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 80
gactccagcc tacacgagtc caaatatggt cccca                               36

<210> SEQ ID NO 81
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 81
accatatttg gactcgtgta ggctggagtc tccagg                              36

<210> SEQ ID NO 82
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 82
cgcaagcttg ccaccatgac agtgctggcg ccagcc                              36
```

```
<210> SEQ ID NO 83
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 83
cgcggatcct ccggaagggg gctgcggggc tgtcgg                                36

<210> SEQ ID NO 84
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 84
gccccgcagc ccctgagcc caaatcttgt gacaaa                                 36

<210> SEQ ID NO 85
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 85
acaagatttg ggctcagggg gctgcggggc tgtcgg                                36

<210> SEQ ID NO 86
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 86
gccccgcagc ccctgagtc caaatatggt ccccca                                 36

<210> SEQ ID NO 87
<211> LENGTH: 36
<212> TYPE: DNA
<213> ORGANISM: Artificial sequence
<220> FEATURE:
<221> NAME/KEY: misc_feature
<222> LOCATION: (1)..(36)
<223> OTHER INFORMATION: primer

<400> SEQUENCE: 87
accatatttg gactcagggg gctgcggggc tgtcgg                                36
```